(12) United States Patent
Crawford et al.

(10) Patent No.: US 9,326,985 B2
(45) Date of Patent: May 3, 2016

(54) HETEROARYL PYRIDONE AND AZA-PYRIDONE AMIDE COMPOUNDS

(71) Applicant: Genentech, Inc., South San Francisco, CA (US)

(72) Inventors: James John Crawford, San Francisco, CA (US); Wendy Lee, San Ramon, CA (US); Wendy B. Young, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/322,051

(22) Filed: Jul. 2, 2014

(65) Prior Publication Data

US 2015/0011461 A1    Jan. 8, 2015

Related U.S. Application Data

(60) Provisional application No. 61/842,648, filed on Jul. 3, 2013.

(51) Int. Cl.
| | | |
|---|---|---|
| *A61K 38/00* | (2006.01) | |
| *A61P 11/06* | (2006.01) | |
| *A61K 31/519* | (2006.01) | |
| *A61K 45/06* | (2006.01) | |
| *C07D 401/14* | (2006.01) | |
| *A61K 31/4985* | (2006.01) | |
| *A61K 31/502* | (2006.01) | |
| *A61K 31/5025* | (2006.01) | |
| *C07D 401/10* | (2006.01) | |
| *C07D 471/04* | (2006.01) | |
| *C07D 471/14* | (2006.01) | |
| *C07D 487/04* | (2006.01) | |
| *C07D 495/04* | (2006.01) | |
| *A61K 31/444* | (2006.01) | |
| *A61K 31/4725* | (2006.01) | |

(52) U.S. Cl.
CPC .......... *A61K 31/519* (2013.01); *A61K 31/444* (2013.01); *A61K 31/4725* (2013.01); *A61K 31/4985* (2013.01); *A61K 31/502* (2013.01); *A61K 31/5025* (2013.01); *A61K 45/06* (2013.01); *C07D 401/10* (2013.01); *C07D 401/14* (2013.01); *C07D 471/04* (2013.01); *C07D 471/14* (2013.01); *C07D 487/04* (2013.01); *C07D 495/04* (2013.01)

(58) Field of Classification Search
CPC ........ A61K 38/55; A61K 38/53; A61K 31/33
See application file for complete search history.

(56) References Cited

U.S. PATENT DOCUMENTS

| | | | |
|---|---|---|---|
| 7,683,064 B2 | 3/2010 | Dewdney et al. | |
| 7,838,523 B2 | 11/2010 | Blomgren et al. | |
| 7,884,108 B2 | 2/2011 | Blomgren et al. | |
| 7,902,194 B2 | 3/2011 | Dewdney et al. | |
| 7,906,509 B2 | 3/2011 | Kennedy-Smith et al. | |
| 7,943,618 B2 | 5/2011 | Dewdney et al. | |
| 7,947,835 B2 | 5/2011 | Brittelli et al. | |
| 8,058,446 B2 | 11/2011 | Blomgren et al. | |
| 8,101,770 B2 | 1/2012 | Charrier et al. | |
| 8,124,604 B2 | 2/2012 | Dewdney et al. | |
| 8,299,077 B2 | 10/2012 | Berthel et al. | |
| 8,318,719 B2 | 11/2012 | Dewdney et al. | |
| 8,324,211 B2 | 12/2012 | Dewdney et al. | |
| 8,426,424 B2 | 4/2013 | Blomgren et al. | |
| 8,426,441 B2 | 4/2013 | Dewdney et al. | |
| 8,481,540 B2 | 7/2013 | Berthel et al. | |
| 8,536,166 B2 | 9/2013 | Dewdney et al. | |
| 8,598,174 B2 | 12/2013 | Barbosa et al. | |

(Continued)

FOREIGN PATENT DOCUMENTS

| | | |
|---|---|---|
| WO | 2012/030990 A1 | 3/2012 |
| WO | 2012/031004 A1 | 3/2012 |

OTHER PUBLICATIONS

Di Paolo et al., "Specific Btk inhibition suppresses B cell- and myeloid cell-mediated arthritis" Nat Chem Biol. 7(1):41-50 ( 2011).
ISR for PCT/EP2014/064044.

(Continued)

*Primary Examiner* — James J Alstrum Acevedo
*Assistant Examiner* — Kaipeen Yang
(74) *Attorney, Agent, or Firm* — Mark D. Kafka

(57) ABSTRACT

Heteroaryl pyridone and aza-pyridone amide compounds of Formula I are provided, and various substituents including stereoisomers, tautomers, and pharmaceutically acceptable salts thereof, useful for inhibiting Btk, and for treating cancer and immune disorders such as inflammation mediated by Btk. Methods of using compounds of Formula I for in vitro, in situ, and in vivo diagnosis, and treatment of such disorders in mammalian cells, or associated pathological conditions, are disclosed.

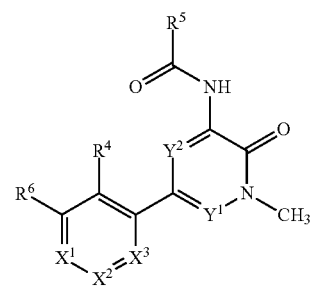

I

21 Claims, 4 Drawing Sheets

(56) References Cited

U.S. PATENT DOCUMENTS

| | | |
|---|---|---|
| 8,618,107 B2 | 12/2013 | Barbosa et al. |
| 8,669,251 B2 | 3/2014 | Crawford et al. |
| 8,716,274 B2 | 5/2014 | Crawford et al. |
| 8,722,676 B2 | 5/2014 | Crawford et al. |
| 8,729,072 B2 | 5/2014 | Crawford et al. |
| 8,729,078 B2 | 5/2014 | Billedeau et al. |
| 8,889,682 B2 | 11/2014 | Brotherton-Pleiss et al. |
| 2008/0125417 A1 | 5/2008 | Currie et al. |
| 2010/0222325 A1* | 9/2010 | Berthel et al. ........... 514/210.21 |

OTHER PUBLICATIONS

Liu et al., "Antiarthritis effect of a novel Bruton's tyrosine kinase (BTK) inhibitor in rat collagen-induced arthritis and mechanism-based pharmacokinetic/pharmacodynamic modeling: relationships between inhibition of BTK phosphorylation and efficacy" J Pharmacol Exp Ther. 338(1):154-63 (2011).

Young et al., "Potent and selective Bruton's tyrosine kinase inhibitors: Discovery of GDC-0834" Bioorganic & Medicinal Chemistry Letters 25:1333-37 (2015).

* cited by examiner

HETEROARYL PYRIDONE AND AZA-PYRIDONE AMIDE COMPOUNDS

CROSS REFERENCE TO RELATED APPLICATIONS

This non-provisional application filed under 37 CFR §1.53 (b), claims the benefit under 35 USC §119(e) of U.S. Provisional Application Ser. No. 61/842,648 filed on 3 Jul. 2013, which is incorporated by reference in entirety.

FIELD OF THE INVENTION

The invention relates generally to compounds for treating disorders mediated by Bruton's Tyrosine Kinase (Btk) including inflammation, immunological, and cancer, and more specifically to compounds which inhibit Btk activity. The invention also relates to methods of using the compounds for in vitro, in situ, and in vivo diagnosis or treatment of mammalian cells, or associated pathological conditions.

BACKGROUND OF THE INVENTION

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival (T. Hunter, *Cell* 1987 50:823-829).

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation. Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to *Staphylococcus*-induced arthritis. A large body of evidence supports the role of B-cells and the humoral immune system in the pathogenesis of autoimmune and/or inflammatory diseases. Protein-based therapeutics (such as Rituxan®, Genentech/Biogen Idec) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production). Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis (Whang et al (2014) Drug Discovery Today in press; Kim et al (2011) Bioorganic & Med. Chem. Letters 21:6258-6263), multiple vasculitides, idiopathic thrombocytopenic purpura (ITP), myasthenia gravis, allergic rhinitis, and asthma (Di Paolo et al (2011) Nature Chem. Biol. 7(1):41-50; Liu (2011) Drug Metab. and Disposition 39(10):1840-1849; Liu et al (2011) Jour. of Pharm. and Exper. Ther. 338(1):154-163; Lou et al (2012) J. Med. Chem. 55(10):4539-4550; Xu D. et al (2012) Jour. Pharm. and Exp. Ther. 341(1):90-103). In addition, Btk has been reported to play a role in apoptosis (Islam and Smith *Immunol. Rev.* 2000 178:49); thus, inhibition of Btk activity can be useful for cancer, as well as the treatment of B-cell lymphoma, leukemia, and other hematological malignancies (U.S. Pat. No. 7,514,444; Feldhahn et al. *J. Exp. Med.* 2005 201:1837). Moreover, given the role of Btk in osteoclast function, the inhibition of Btk activity can be useful for the treatment of bone disorders such as osteoporosis. Specific Btk inhibitors have been reported (U.S. Pat. No. 7,884,108, WO 2010/056875; U.S. Pat. No. 7,405,295; U.S. Pat. No. 7,393,848; WO 2006/053121; U.S. Pat. No. 7,947,835; US 2008/0139557; U.S. Pat. No. 7,838,523; US 2012/0040949; US 2012/0295885; US 2013/0045965; U.S. Pat. No. 7,683,064; U.S. Pat. No. 7,902,194; U.S. Pat. No. 7,906,509; U.S. Pat. No. 8,124,604; US 2008/0125417; US 2011/0118233; WO2011/140488; US 2012/0010191; WO2013/067274; US 2013/0116235; WO2013/067277; US 2013/0116245; WO2013/067260; US 2013/0116262; WO2013/067264; US 2013/0116246.

SUMMARY OF THE INVENTION

The invention relates generally to heteroaryl pyridone and aza-pyridone amide compounds with Bruton's Tyrosine Kinase (Btk) modulating activity having the Formula I structure:

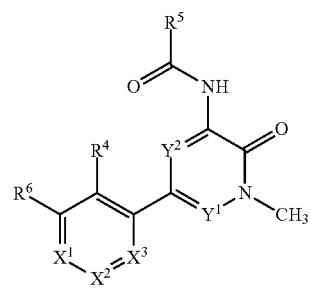

including stereoisomers, tautomers, or pharmaceutically acceptable salts thereof. The various substituents are defined herein.

One aspect of the invention is a pharmaceutical composition comprised of a Formula I compound and a pharmaceutically acceptable carrier, glidant, diluent, or excipient. The pharmaceutical composition may further comprise a second therapeutic agent.

Another aspect of the invention is a process for making a pharmaceutical composition which comprises combining a Formula I compound with a pharmaceutically acceptable carrier.

The invention includes a method of treating a disease or disorder which method comprises administering a therapeutically effective amount of a Formula I compound to a patient with a disease or disorder selected from immune disorders, cancer, cardiovascular disease, viral infection, inflammation, metabolism/endocrine function disorders and neurological disorders, and mediated by Bruton's tyrosine kinase.

The invention includes a kit for treating a condition mediated by Bruton's tyrosine kinase, comprising: a) a first pharmaceutical composition comprising a Formula I compound; and b) instructions for use.

The invention includes a Formula I compound for use as a medicament, and for use in treating a disease or disorder selected from immune disorders, cancer, cardiovascular disease, viral infection, inflammation, metabolism/endocrine function disorders and neurological disorders, and mediated by Bruton's tyrosine kinase.

The invention includes a Formula I compound for use in combination with an additional therapeutic agent in treating a disease or disorder.

The invention includes use of a Formula I compound in the manufacture of a medicament for the treatment of immune disorders, cancer, cardiovascular disease, viral infection, inflammation, metabolism/endocrine function disorders and neurological disorders, and where the medicament mediates Bruton's tyrosine kinase.

The invention includes methods of making a Formula I compound.

BRIEF DESCRIPTION OF THE DRAWINGS

FIG. 1 shows the synthesis of 4,4-dimethylpyrrolidine-2-carboxylic acid 137f from tert-butyl 5-oxopyrrolidine-2-carboxylate 137a.

FIG. 3 shows the synthesis of 6-(difluoromethoxy)-8-fluoro-3,4-dihydroisoquinolin-1(2H)-one 144j from 4-bromo-2-fluorobenzoic acid 144a.

FIG. 4 shows the synthesis of 6-(trifluoromethoxy)-3,4-dihydroisoquinolin-1(2H)-one 158g from 3-(trifluoromethoxy)benzaldehyde 158a.

FIG. 5 shows the synthesis of (2-(6-(tert-butyl)-1-methyl-1H-benzo[d]imidazo-2-yl)-4-chloropyridin-3-yl)methanol 160k and (2-(5-(tert-butyl)-1-methyl-1H-benzo[d]imidazo-2-yl)-4-chloropyridin-3-yl)methanol 160l from 2-bromo-4-chloronicotinaldehyde 160a.

FIG. 6 shows the synthesis of (R)—N-[5-[2-(6-tert-butyl-8-fluoro-1-oxo-phthalazin-2-yl)-3-(hydroxymethyl)-4-pyridyl]-1-methyl-2-oxo-3-pyridyl]-6-methyl-6-azaspiro[2.5]octane-2-carboxamide 165 and (S)—N-[5-[2-(6-tert-butyl-8-fluoro-1-oxo-phthalazin-2-yl)-3-(hydroxymethyl)-4-pyridyl]-1-methyl-2-oxo-3-pyridyl]-6-methyl-6-azaspiro[2.5]octane-2-carboxamide 166 from tert-butyl 4-oxopiperidine-1-carboxylate 165a.

DETAILED DESCRIPTION OF EXEMPLARY EMBODIMENTS

Figure 1:
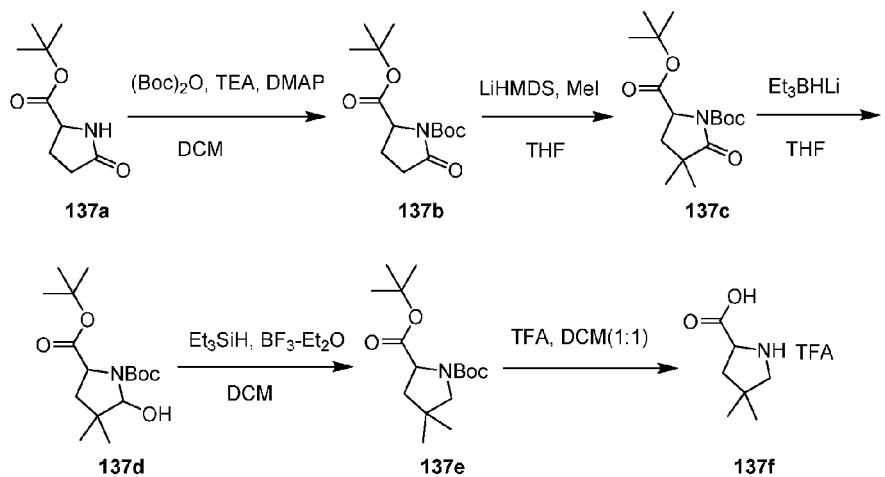

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this application is based on IUPAC systematic nomenclature, unless indicated otherwise.

DEFINITIONS

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C$ ($CH_3$)$_2$CH(CH$_3$)$_2$), 3,3-dimethyl-2-butyl (—CH(CH$_3$)C (CH$_3$)$_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—CH$_2$—), ethylene (—CH$_2$CH$_2$—), propylene (—CH$_2$CH$_2$CH$_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, sp$^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH═CH—), allyl (—CH$_2$CH═CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —CH$_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —CH$_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo [2.2.2]octane and bicyclo[3.2.2]nonane. Spiro carbocyclyl moieties are also included within the scope of this definition. Examples of spiro carbocyclyl moieties include [2.2]pentanyl, [2.3]hexanyl, and [2.4]heptanyl. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo

[4.1.0]heptanyl, azabicyclo[2.2.2]hexanyl, 3H-indolyl quinolizinyl and N-pyridyl ureas. Spiro heterocyclyl moieties are also included within the scope of this definition. Examples of spiro heterocyclyl moieties include azaspiro[2.5]octanyl and azaspiro[2.4]heptanyl. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (NHL, all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: ibrutinib (IMBRUVICA™, APCI-32765, Pharmacyclics Inc./Janssen Biotech Inc.; CAS Reg. No. 936563-96-1, U.S. Pat. No. 7,514,444), idelalisib (formerly CAL-101, GS 1101, GS-1101, Gilead Sciences Inc.; CAS Reg. No. 1146702-54-6), erlotinib (TARCEVA®, Genentech/OSI Pharm.), docetaxel (TAXOTERE®, Sanofi-Aventis), 5-FU (fluorouracil, 5-fluorouracil, CAS Reg. No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCINO), Akti-1/2, HPPD, and rapamycin.

Chemotherapeutic agents include Bcl-2 inhibitors and JAK inhibitors.

More examples of chemotherapeutic agents include: oxaliplatin (ELOXATIN®, Sanofi), bortezomib (VELCADE®, Millennium Pharm.), sutent (SUNITINIB®, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR®, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chlorambucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the Btk inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center (s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemistry is definitively established, such as from x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, aryl-aliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (-log Ki), in which higher values indicate exponentially greater potency.

The term "$IC_{50}$" is the half maximal inhibitory concentration and denotes the concentration of a particular compound required for obtaining 50% inhibition of a biological process in vitro. $IC_{50}$ values can be converted logarithmically to $pIC_{50}$ values (-log $IC_{50}$), in which higher values indicate exponentially greater potency. The $IC_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as $IC_{70}$, $IC_{90}$, etc., may be calculated.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labeled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Heteroaryl Pyridone and Aza-Pyridone Amide Compounds

The present invention provides heteroaryl pyridone and aza-pyridone amide compounds of Formula I, including Formulas Ia-Ii, and pharmaceutical formulations thereof, which are potentially useful in the treatment of diseases, conditions and/or disorders modulated by Btk.

Formula I compounds have the structure:

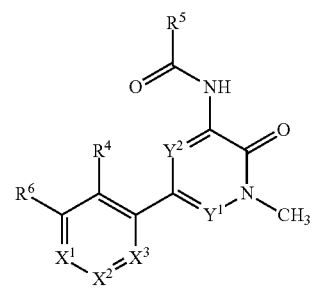

I or stereoisomers, tautomers, or pharmaceutically acceptable salts thereof, wherein:

$X^1$ is $CR^1$ or N;

$X^2$ is $CR^2$ or N;

$X^3$ is $CR^3$ or N;

$R^1$, $R^2$ and $R^3$ are independently selected from H, F, Cl, CN, —$NH_2$, —$NHCH_3$, —$N(CH_3)_2$, —OH, —$OCH_3$, —$OCH_2CH_3$, —$OCH_2CH_2OH$, and $C_1$-$C_3$ alkyl;

$R^4$ is selected from H, F, Cl, CN, —$CH_2OH$, —$CH(CH_3)$OH, —$C(CH_3)_2OH$, —$CH(CF_3)OH$, —$CH_2F$, —$CHF_2$, —$CH_2CHF_2$, —$CF_3$, —$C(O)NH_2$, —$C(O)NHCH_3$, —$C(O)N(CH_3)_2$, —$NH_2$, —$NHCH_3$, —$N(CH_3)_2$, —$NHC(O)CH_3$, —OH, —$OCH_3$, —$OCH_2CH_3$, —$OCH_2CH_2OH$, cyclopropyl, cyclopropylmethyl, 1-hydroxycyclopropyl, imidazolyl, pyrazolyl, 3-hydroxy-oxetan-3-yl, oxetan-3-yl, and azetidin-1-yl;

$R^5$ is $C_3$-$C_{12}$ carbocyclyl, —($C_1$-$C_6$ alkyl)-($C_3$-$C_{12}$ carbocyclyl), $C_2$-$C_{20}$ heterocyclyl, ($C_1$-$C_6$ alkyl)-($C_2$-$C_{20}$ heterocyclyl), $C_1$-$C_6$ alkyl, —NH—($C_1$-$C_6$ alkyl), —($C_1$-$C_6$ alkyl)-($C_1$-$C_{20}$ heteroaryl), $C_1$-$C_{20}$ heteroaryl, $C_6$-$C_{20}$ aryl;

$R^6$ is selected from the structures:
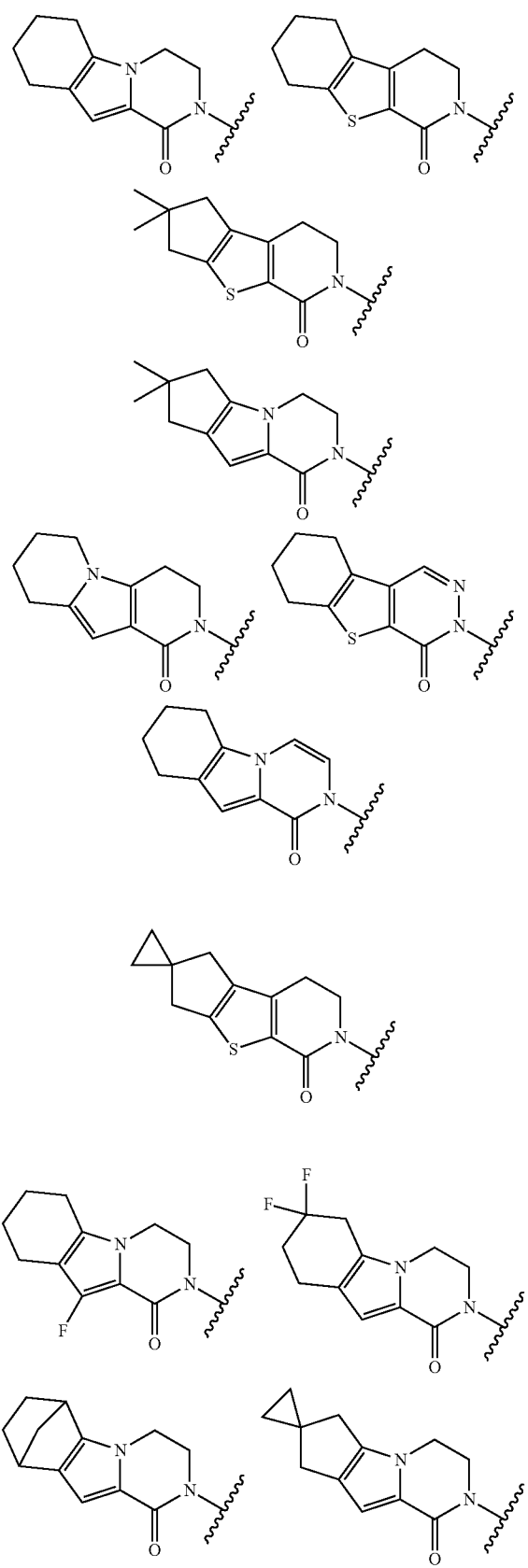
-continued
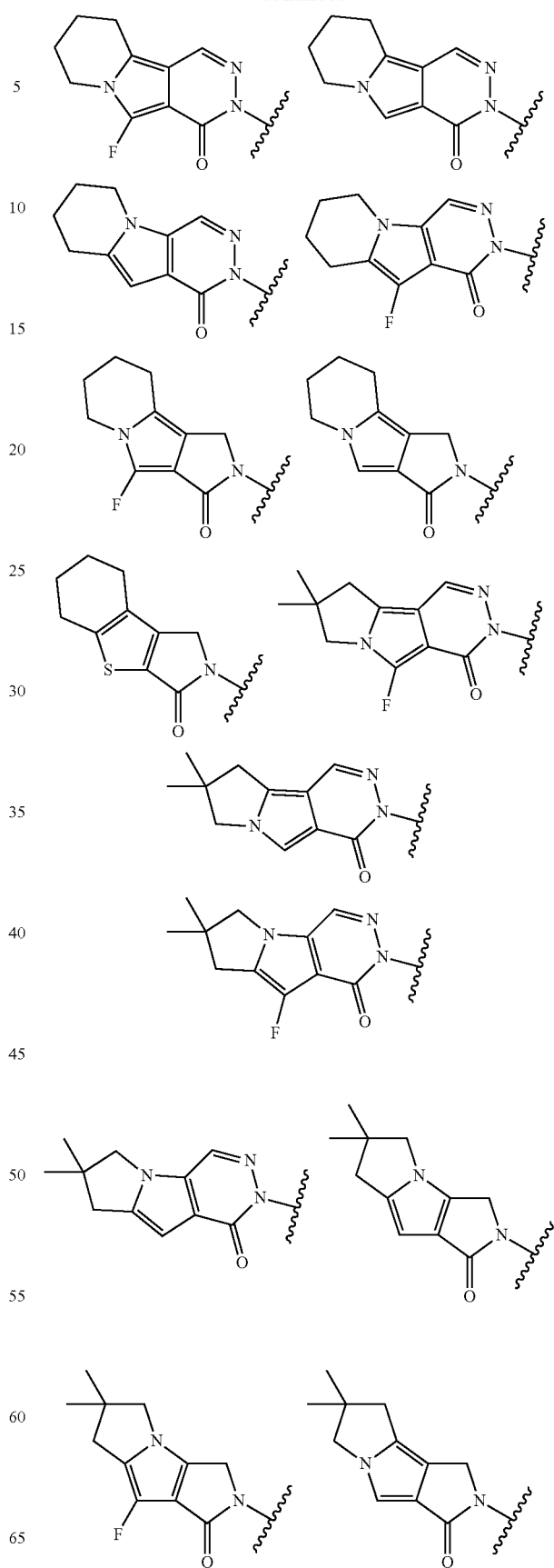

-continued

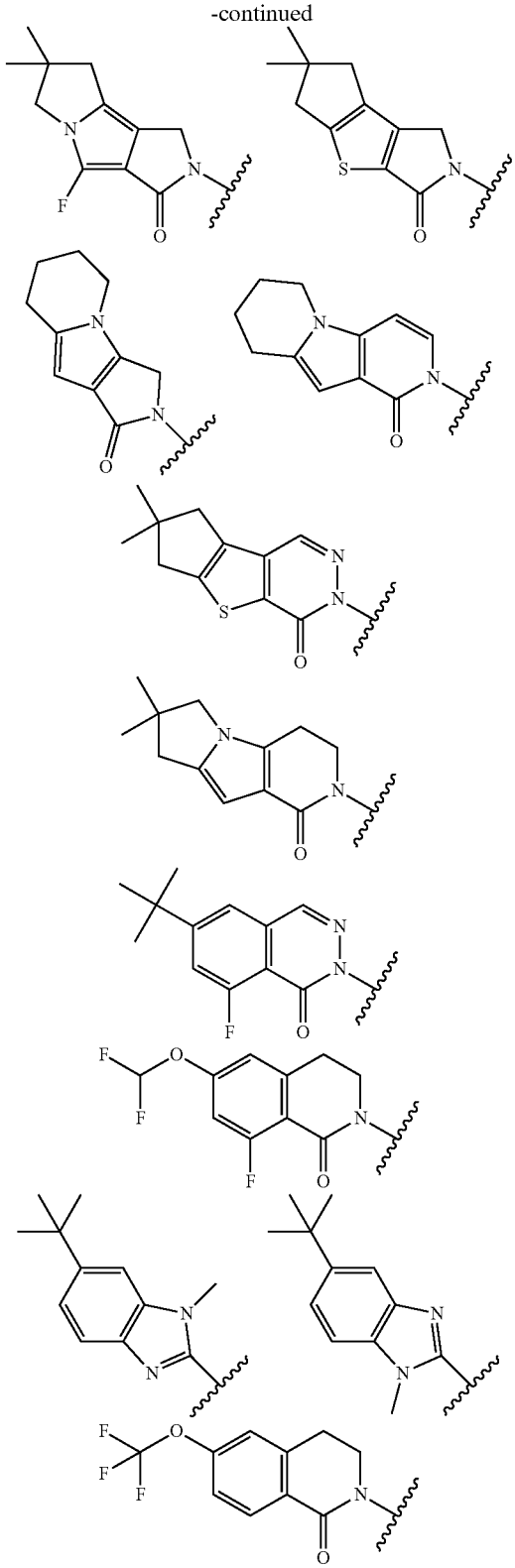

where the wavy line indicates the site of attachment; and $Y^1$ and $Y^2$ are independently selected from CH and N; where alkyl, carbocyclyl, heterocyclyl, aryl, and heteroaryl are optionally substituted with one or more groups independently selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, oxetanyl, azetidinyl, 1-methylazetidin-3-yl)oxy, N-methyl-N-oxetan-3-ylamino, azetidin-1-ylmethyl, pyrrolidin-1-yl, and morpholino.

Exemplary embodiments of Formula I compounds include compounds of Formulas Ia-c:

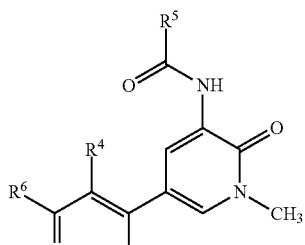

Ia

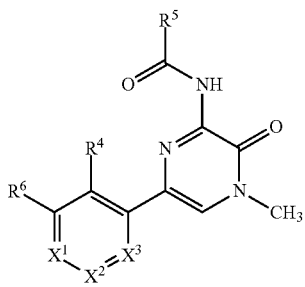

Ib

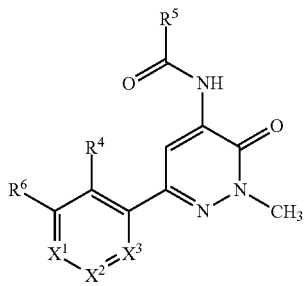

Ic

Exemplary embodiments of Formula I compounds also include compounds of Formulas Id-i:

Id
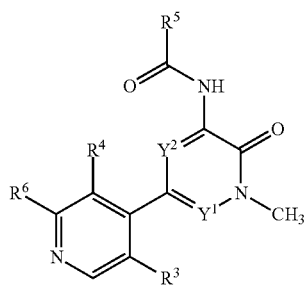

Ie
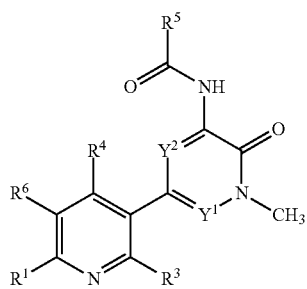

If
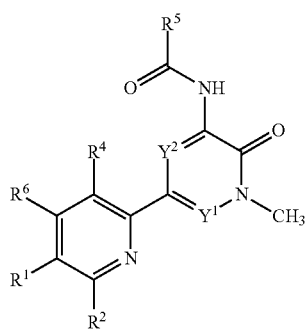

Ig
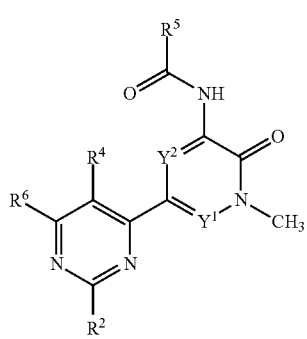

Ih
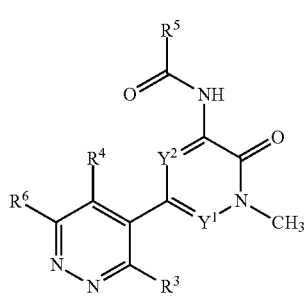

Ii

Exemplary embodiments of Formula I compounds include wherein one or two of $X^1$, $X^2$, and $X^3$ are N.

Exemplary embodiments of Formula I compounds include wherein $X^1$ is N, $X^2$ is N, $X^3$ is N, $X^1$ and $X^3$ are N, $X^1$ and $X^2$ are N, or $X^2$ and $X^3$ are N, as shown in Formulas Ic-Ii.

Exemplary embodiments of Formula I compounds include wherein $X^1$ is $CR^1$, $X^2$ is $CR^2$, and $X^3$ is $CR^3$.

Exemplary embodiments of Formula I compounds include the compounds in Tables 1 and 2.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. In some instances, the stereochemistry has not been determined or has been provisionally assigned.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "IC$_{50}$". Determination of IC$_{50}$ values can be accomplished using conventional techniques known in the art. In general, an IC$_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the IC$_{50}$ value. Analogously, other inhibitory concentrations can be defined through appropriate determinations of activity. For example, in some settings it can be desirable to establish a 90% inhibitory concentration, i.e., IC$_{90}$, etc.

Formula I compounds were tested by a standard biochemical Btk, Kinase Assay (Example 901).

A general procedure for a standard cellular Btk, Kinase Assay that can be used to test Formula I compounds is a Ramos Cell Btk Assay (Example 902).

A standard cellular B-cell proliferation assay can be used to test Formula I compounds with B-cells purified from spleen of Balb/c mice (Example 903).

A standard T cell proliferation assay can be used to test Formula I compounds with T-cells purified from spleen of Balb/c mice (Example 904).

A CD86 Inhibition assay can be conducted on Formula I compounds for the inhibition of B cell activity using total mouse splenocytes purified from spleens of 8-16 week old Balb/c mice (Example 905).

A B-ALL Cell Survival Assay can be conducted on Formula I compounds to measure the number of viable B-ALL cells in culture (Example 906).

A CD69 Whole Blood Assay can be conducted on Formula I compounds to determine the ability of compounds to inhibit the production of CD69 by B lymphocytes in human whole blood activated by crosslinking surface IgM with goat F(ab')2 anti-human IgM (Example 907). CD69 is a type II C-type lectin involved in lymphocyte migration and cytokine secretion. CD69 expression represents one of the earliest available indicators of leukocyte activation and its rapid induction occurs through transcriptional activation (Vazquez et al (2009) Jour. of Immunology Published Oct. 19, 2009, doi: 10.4049/jimmunol.0900839). Concentration-dependent inhibition of antigen receptor stimulation by selective Btk inhibitors induces cell surface expression of the lymphocyte activation marker CD69 (Honigberg et al (2010) Proc. Natl. Acad. Sci. 107(29):13075-13080). Thus, CD69 inhibition by selective Btk inhibitors may be correlated with therapeutic efficacy of certain B-cell disorders. The CD69 Hu Blood FACS IC70 values are displayed for exemplary Formula I compounds in Tables 1 and 2.

Anti-inflammation effects of Formula I compounds can also be tested by a collagen-induced arthritis (CIA) assay in mice or rats (William R O (2004) Methods of Mol. Med. 98:207-216). Collagen-induced arthritis is an animal model of rheumatoid arthritis (RA) that is widely used to address questions of disease pathogenesis and to validate therapeutic targets. Arthritis is normally induced in mice or rats by immunization with autologous or heterologous type II collagen in adjuvant. Susceptibility to collagen-induced arthritis is strongly associated with major histocompatibility complex class II genes, and the development of arthritis is accompanied by a robust T- and B-cell response to type II collagen. The chief pathological features of CIA include a proliferative synovitis with infiltration of polymorphonuclear and mononuclear cells, pannus formation, cartilage degradation, erosion of bone, and fibrosis. As in RA, pro-inflammatory cytokines, such as tumor necrosis factor alpha(TNFalpha) and interleukin (IL)-1beta, are abundantly expressed in the arthritic joints of mice with CIA, and blockade of these molecules results in a reduction of disease severity. Test subjects are injected at the base of the tail with a formulation of a Formula I compound and the onset of arthritis is synchronized (boosted) by systemic administration of collagen in Incomplete Freund's adjuvant. Inflammation of the paws and limb joints is quantified using a scoring system that involves the assessment of the paws.

The cytotoxic or cytostatic activity of Formula I exemplary compounds can be measured by: establishing a proliferating mammalian tumor cell line in a cell culture medium, adding a Formula I compound, culturing the cells for a period from about 6 hours to about 5 days; and measuring cell viability (Example 908). Cell-based in vitro assays are used to measure viability, i.e. proliferation (IC$_{50}$), cytotoxicity (EC$_{50}$), and induction of apoptosis (caspase activation) and may be useful in predicting clinical efficacy against hematological malignancies and solid tumors.

The in vitro potency of the combinations of Formula I compounds with chemotherapeutic agents can be measured by the cell proliferation assay of Example 908; the CellTiter-Glo® Luminescent Cell Viability Assay, commercially available from Promega Corp., Madison, Wis. This homogeneous assay method is based on the recombinant expression of *Coleoptera* luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602, 677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative efficacy of Formula I exemplary compounds and combinations with chemotherapeutic agents are measured by the CellTiter-Glo® Assay (Example 908) against certain hematological tumor cell lines. EC$_{50}$ values are established for the tested compounds and combinations.

Exemplary Formula I compounds in Tables 1 and 2 were made, characterized, and tested for inhibition of Btk according to the methods of this invention, and have the following structures and corresponding names (ChemDraw Ultra, Ver-

TABLE 1

| No. | Structure | IUPAC Name | MW | BTK LC3K (KI) | CD69 Hu Blood FACS (IC50) |
|---|---|---|---|---|---|
| 101 | 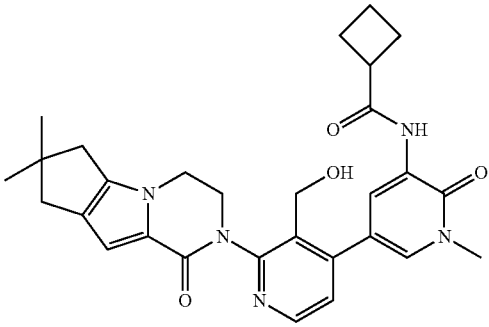 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]cyclobutanecarboxamide | 515.60 | 0.0312 | 4.2+ |
| 102 | 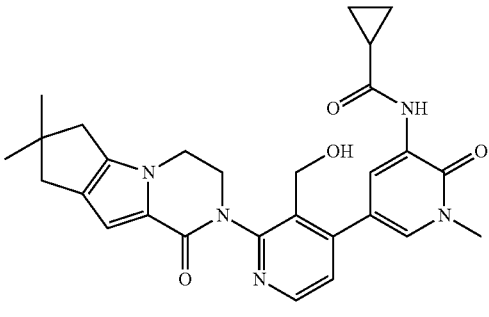 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]cyclopropanecarboxamide | 501.58 | 0.0033 | 0.136 |
| 103 | 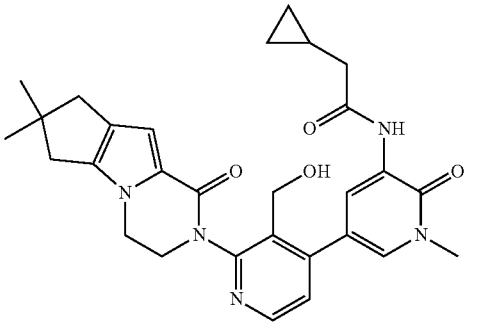 | 2-cyclopropyl-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]acetamide | 515.60 | 0.231 | 4.9 |
| 104 | 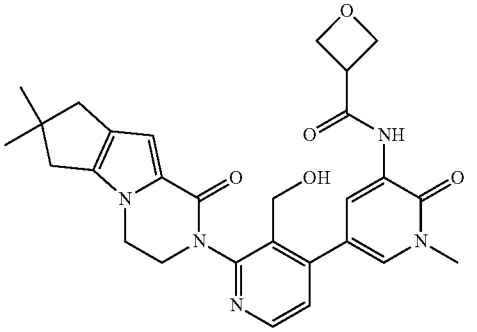 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]oxetane-3-carboxamide | 517.58 | 0.131 | | sion 9.0.1, and ChemBioDraw, Version 11.0, CambridgeSoft Corp., Cambridge Mass.). Where more than one name is associated with a Formula I compound or intermediate, the chemical structure shall define the compound.

TABLE 1-continued

| No. | Structure | IUPAC Name | MW | BTK LC3K (KI) | CD69 Hu Blood FACS (IC50) |
|---|---|---|---|---|---|
| 105 | 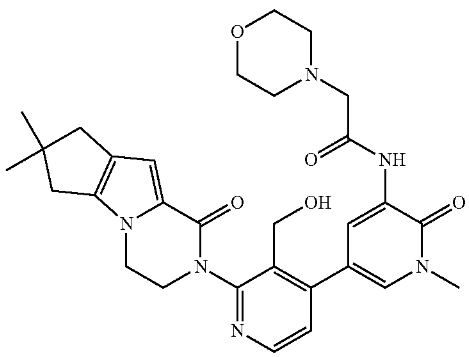 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-morpholino-acetamide | 560.644 | >0.0556 | >5 |
| 106 | 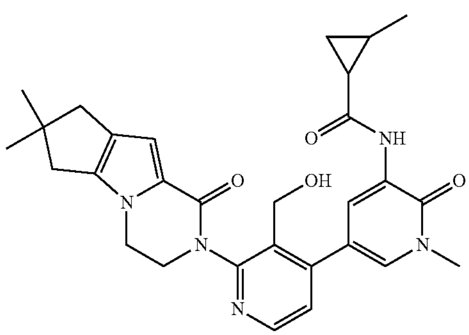 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methyl-cyclopropanecarboxamide | 515.603 | 0.0106 | 0.373 |
| 107 | 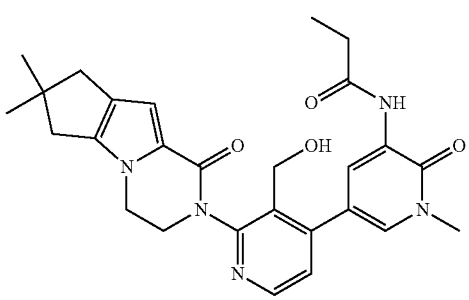 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]propanamide | 489.566 | 0.0517 | 1.6 |
| 108 | 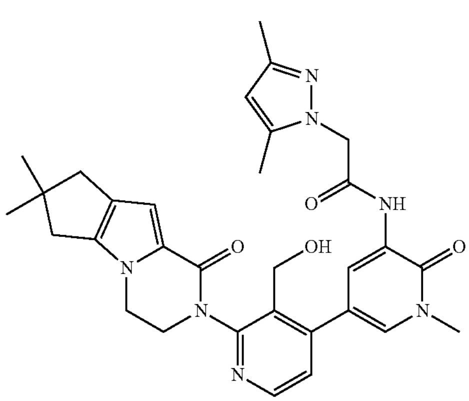 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-(3,5-dimethylpyrazol-1-yl)acetamide | 569.654 | 0.0516 | 2.4 |

TABLE 1-continued

| No. | Structure | IUPAC Name | MW | BTK LC3K (KI) | CD69 Hu Blood FACS (IC50) |
|---|---|---|---|---|---|
| 109 | 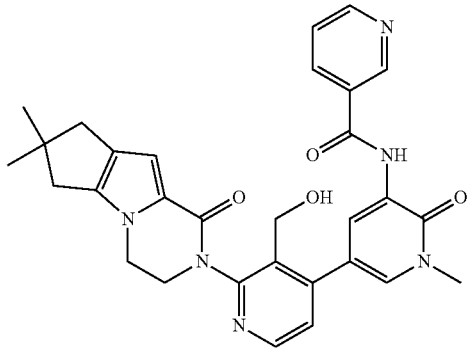 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]pyridine-3-carboxamide | 538.597 | 0.14 | >5.2 |
| 110 | 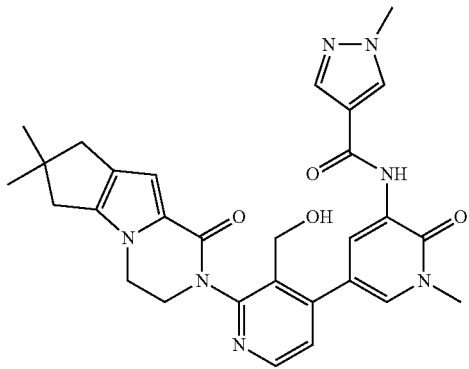 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-1-methyl-pyrazole-4-carboxamide | 541.601 | >0.167 | >2.6 |
| 111 | 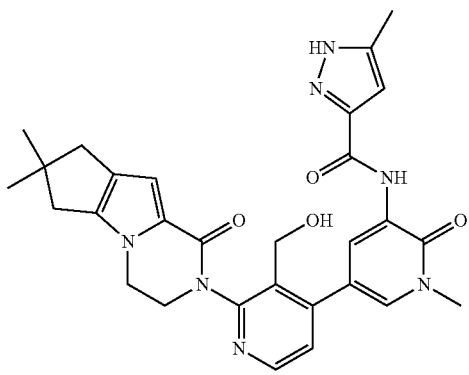 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-5-methyl-1H-pyrazole-3-carboxamide | 541.601 | >0.50 | >5.4 |
| 112 | 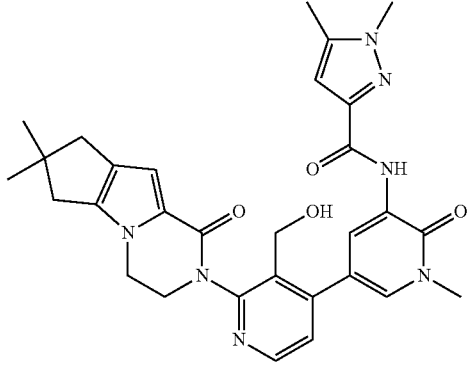 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-1,5-dimethyl-pyrazole-3-carboxamide | 555.628 | >0.50 | >5.8 |

TABLE 1-continued

| No. | Structure | IUPAC Name | MW | BTK LC3K (KI) | CD69 Hu Blood FACS (IC50) |
|---|---|---|---|---|---|
| 113 | 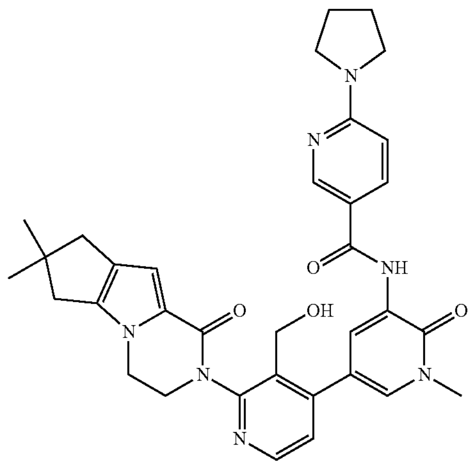 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-6-pyrrolidin-1-yl-pyridine-3-carboxamide | 607.702 | 0.077 | >3.5 |
| 114 | 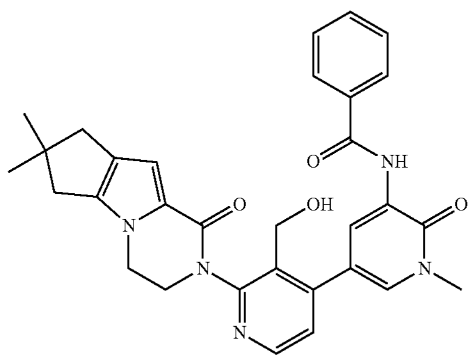 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]benzamide | 537.609 | 0.236 | >5.4 |
| 115 | 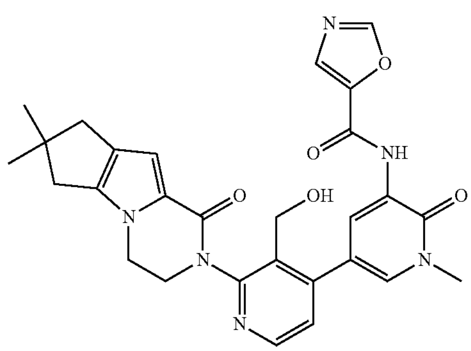 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]oxazole-5-carboxamide | 528.559 | >0.50 | >3.2 |
| 116 | 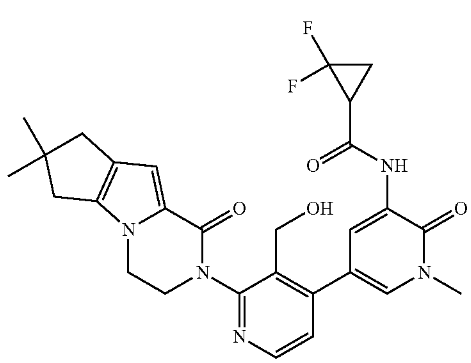 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2,2-difluoro-cyclopropanecarboxamide | 537.558 | 0.0348 | 0.988 |

TABLE 1-continued

| No. | Structure | IUPAC Name | MW | BTK LC3K (KI) | CD69 Hu Blood FACS (IC50) |
|---|---|---|---|---|---|
| 117 | 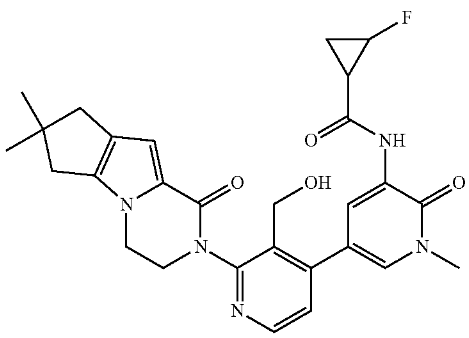 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide | 519.567 | 0.0035 | 0.567 |
| 118 | 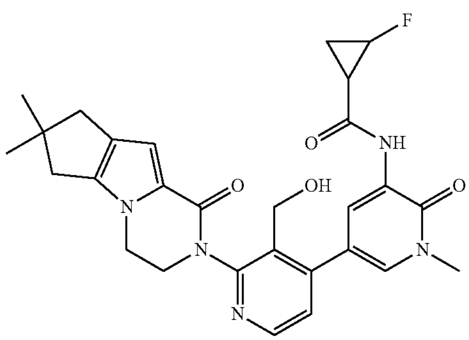 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide | 519.567 | 0.00589 | 0.219 |
| 119 | 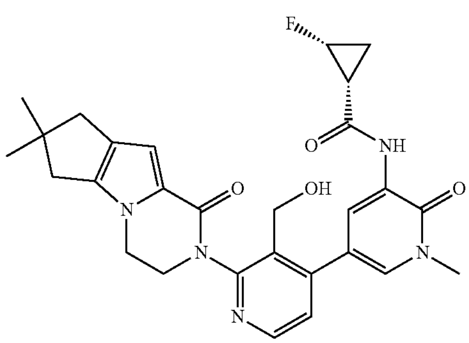 | (1R,2R)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide | 519.567 | 0.00177 | 0.122 |
| 120 | 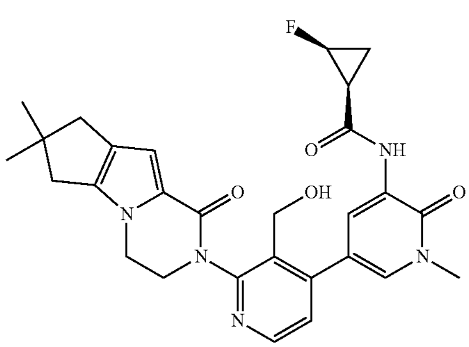 | (1S,2S)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide | 519.567 | 0.00275 | 0.0858 |

TABLE 1-continued

| No. | Structure | IUPAC Name | MW | BTK LC3K (KI) | CD69 Hu Blood FACS (IC50) |
|---|---|---|---|---|---|
| 121 | 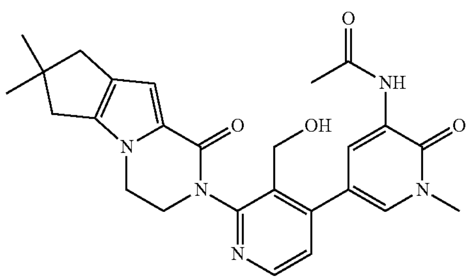 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]acetamide | 475.54 | 0.0347 | 0.5351 |
| 122 | 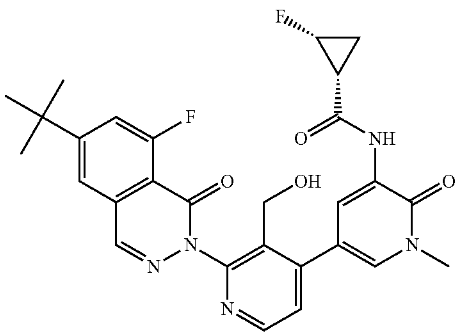 | (1R,2R)-N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide | 535.542 | 0.0035 | 0.1280 |
| 123 | 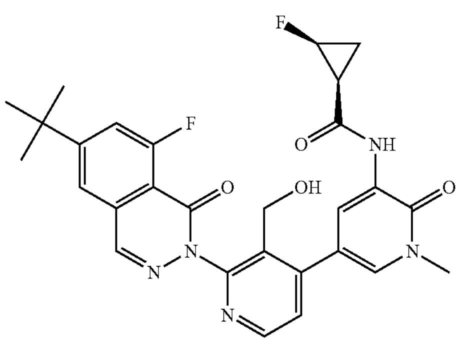 | (1S,2S)-N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide | 535.542 | 0.00224 | 0.0304 |
| 124 | 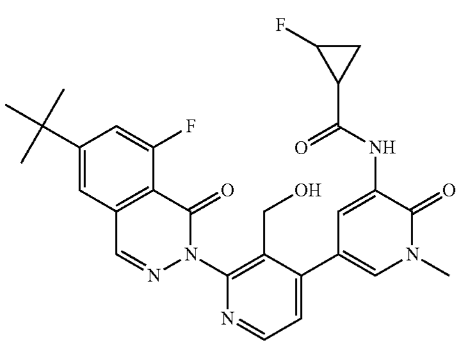 | N-[5-[2-(6-tert-butyl-8-fluoro-1-oxo-phthalazin-2-yl)-3-(hydroxymethyl)-4-pyridyl]-1-methyl-2-oxo-3-pyridyl]-2-fluoro-cyclopropanecarboxamide | 535.542 | 0.00336 | 0.1099 |

TABLE 1-continued

| No. | Structure | IUPAC Name | MW | BTK LC3K (KI) | CD69 Hu Blood FACS (IC50) |
|---|---|---|---|---|---|
| 125 | 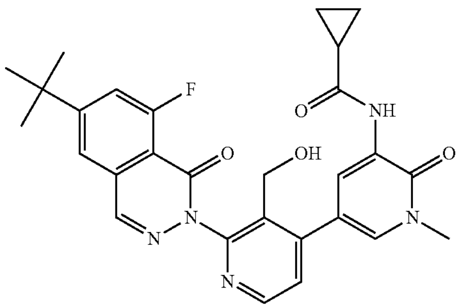 | N-[5-[2-(6-tert-butyl-8-fluoro-1-oxo-phthalazin-2-yl)-3-(hydroxymethyl)-4-pyridyl]-1-methyl-2-oxo-3-pyridyl]cyclopropanecarboxamide | 517.551 | 0.00216 | 0.0625 |
| 126 | 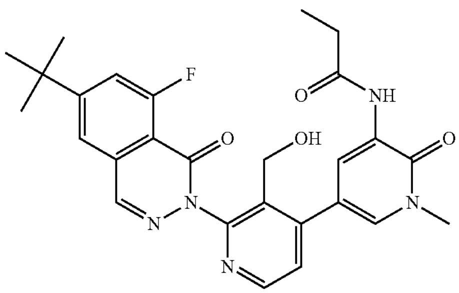 | N-[5-[2-(6-tert-butyl-8-fluoro-1-oxo-phthalazin-2-yl)-3-(hydroxymethyl)-4-pyridyl]-1-methyl-2-oxo-3-pyridyl]propanamide | 505.541 | 0.00701 | 0.5266 |
| 127 | 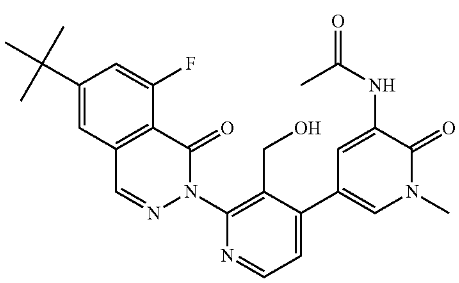 | N-[5-[2-(6-tert-butyl-8-fluoro-1-oxo-phthalazin-2-yl)-3-(hydroxymethyl)-4-pyridyl]-1-methyl-2-oxo-3-pyridyl]acetamide | 491.514 | 0.0108 | 0.3353 |

TABLE 2

| No. | Structure | IUPAC Name | MW | BTK LC3K (Ki) | CD69 Hu Blood FACS (IC50) |
|---|---|---|---|---|---|
| 128 | 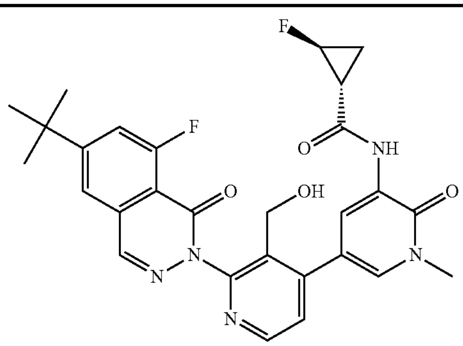 | (1R,2S)-N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide | 535.542 | 0.00336 | 0.11 |

TABLE 2-continued

| No. | Structure | IUPAC Name | MW | BTK LC3K (Ki) | CD69 Hu Blood FACS (IC50) |
|---|---|---|---|---|---|
| 129 | 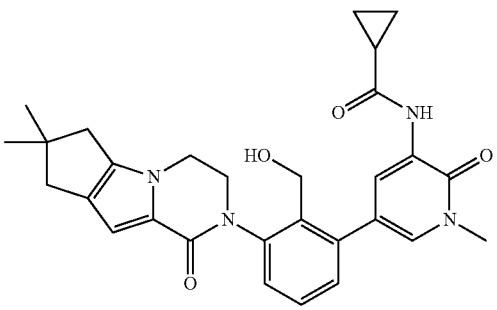 | N-[5-[3-(7,7-dimethyl-4-oxo-1,2,6,8-tetrahydrocyclopenta[3,4]pyrrolo[3,5-b]pyrazin-3-yl)-2-(hydroxymethyl)phenyl]-1-methyl-2-oxo-3-pyridyl]cyclopropanecarboxamide | 500.589 | 0.00378 | 0.0512 |
| 130 | 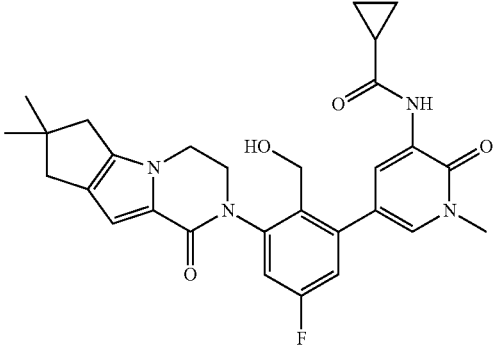 | N-[5-[3-(7,7-dimethyl-4-oxo-1,2,6,8-tetrahydrocyclopenta[3,4]pyrrolo[3,5-b]pyrazin-3-yl)-5-fluoro-2-(hydroxymethyl)phenyl]-1-methyl-2-oxo-3-pyridyl]cyclopropanecarboxamide | 518.579 | 0.00129 | 0.035 |
| 131 | 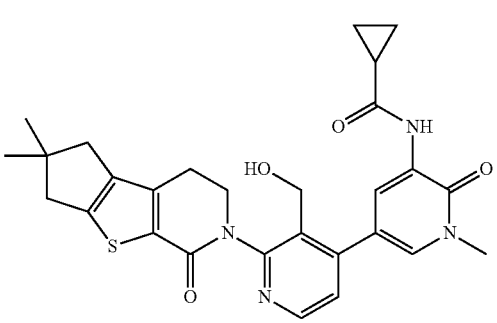 | N-[5-[2-(7,7-dimethyl-4-oxo-1,2,6,8-tetrahydrocyclopenta[3,4]thieno[1,3-c]pyridin-3-yl)-3-(hydroxymethyl)-4-pyridyl]-1-methyl-2-oxo-3-pyridyl]cyclopropanecarboxamide | 518.627 | 0.00706 | 0.24 |
| 132 | 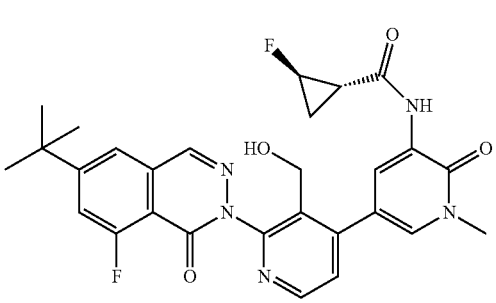 | (1S,2R)-N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide | 535.542 | 0.0157 | 0.326 |

TABLE 2-continued

| No. | Structure | IUPAC Name | MW | BTK LC3K (Ki) | CD69 Hu Blood FACS (IC50) |
|---|---|---|---|---|---|
| 133 | 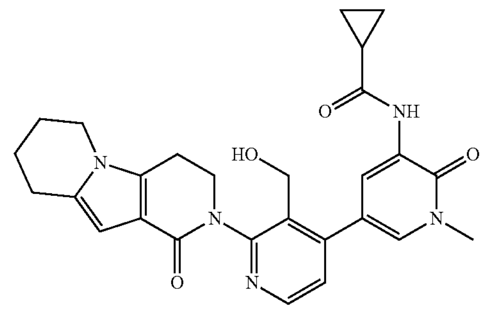 | N-[5-[3-(hydroxymethyl)-2-(1-oxo-3,4,6,7,8,9-hexahydropyrido[3,4-b]indolizin-2-yl)-4-pyridyl]-1-methyl-2-oxo-3-pyridyl]cyclopropanecarboxamide | 487.55 | 0.077 | >4.3 |
| 134 | 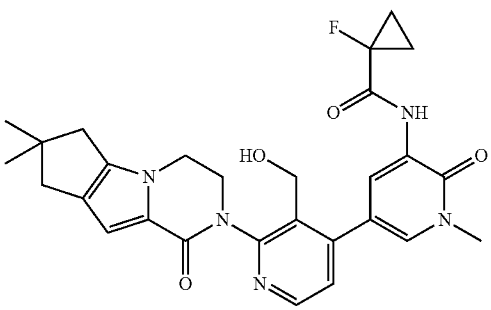 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-1-fluoro-cyclopropanecarboxamide | 519.567 | 0.129 | 4.2 |
| 135 | 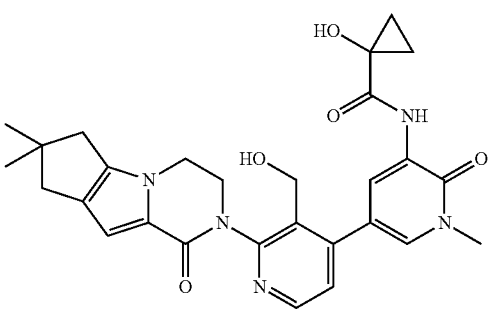 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-1-hydroxy-cyclopropanecarboxamide | 517.576 | 0.186 | >3.4 |
| 136 | 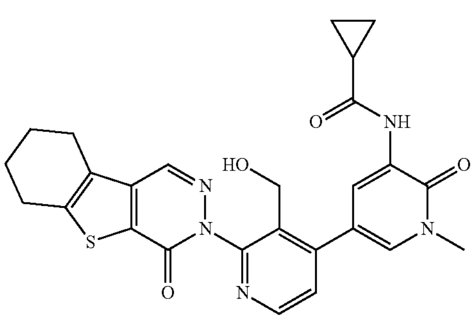 | N-[5-[3-(hydroxymethyl)-2-(4-oxo-6,7,8,9-tetrahydrobenzothiopheno[2,3-d]pyridazin-3-yl)-4-pyridyl]-1-methyl-2-oxo-3-pyridyl]cyclopropanecarboxamide | 503.573 | 0.00435 | 1.1 |

TABLE 2-continued

| No. | Structure | IUPAC Name | MW | BTK LC3K (Ki) | CD69 Hu Blood FACS (IC50) |
|---|---|---|---|---|---|
| 137 | 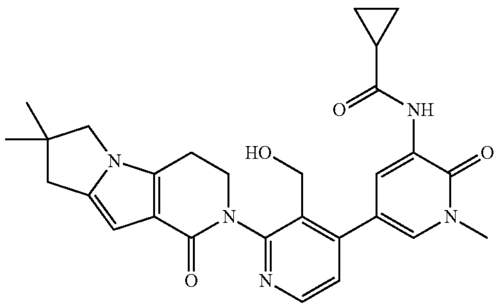 | N-[5-[2-(7,7-dimethyl-4-oxo-1,2,6,8-tetrahydropyrido[3,4-b]pyrrolizin-3-yl)-3-(hydroxymethyl)-4-pyridyl]-1-methyl-2-oxo-3-pyridyl]cyclopropanecarboxamide | 501.577 | 0.0285 | 0.616 |
| 138 | 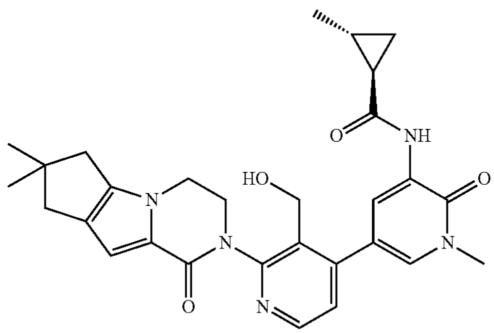 | (1R,2R)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methyl-cyclopropanecarboxamide | 515.603 | 0.0438 | 2.6 |
| 139 | 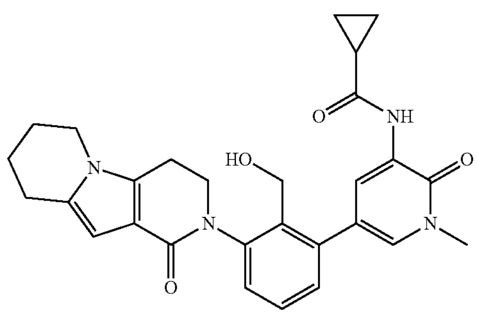 | N-[5-[2-(hydroxymethyl)-3-(1-oxo-3,4,6,7,8,9-hexahydropyrido[3,4-b]indolizin-2-yl)phenyl]-1-methyl-2-oxo-3-pyridyl]cyclopropanecarboxamide | 486.562 | 0.0078 | 0.689 |
| 140 | 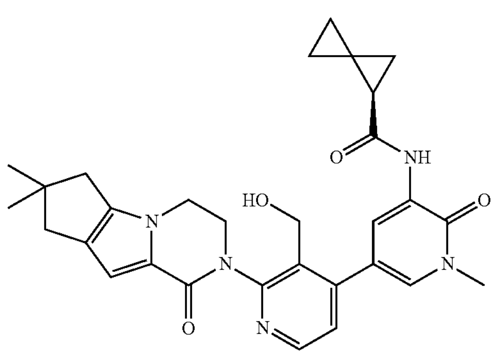 | (R)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.2]pentane-2-carboxamide | 527.614 | 0.0052 | 1.4 |

TABLE 2-continued

| No. | Structure | IUPAC Name | MW | BTK LC3K (Ki) | CD69 Hu Blood FACS (IC50) |
|---|---|---|---|---|---|
| 141 | 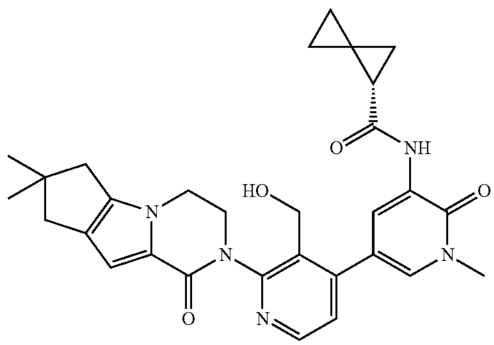 | (S)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.2]pentane-2-carboxamide | 527.614 | 0.0058 | 1.6 |
| 142 | 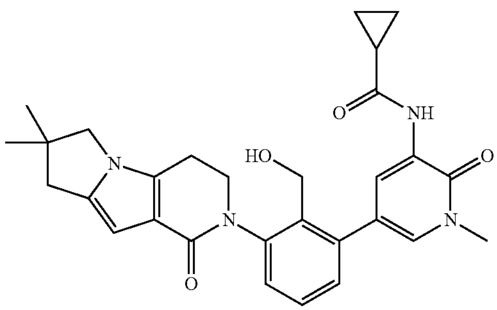 | N-[5-[3-(7,7-dimethyl-4-oxo-1,2,6,8-tetrahydropyrido[3,4-b]pyrrolizin-3-yl)-2-(hydroxymethyl)phenyl]-1-methyl-2-oxo-3-pyridyl]cyclopropanecarboxamide | 500.589 | 0.0018 | 0.070 |
| 143 | 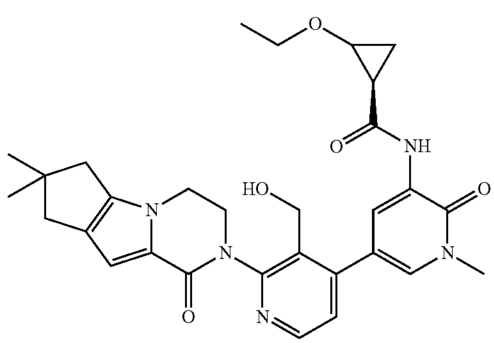 | (1R)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-ethoxy-cyclopropanecarboxamide | 545.629 | 0.053 | 2.2 |
| 144 | 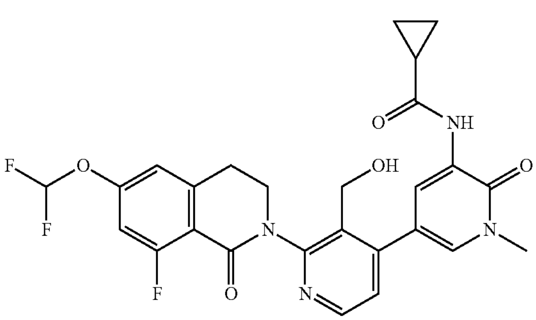 | N-[5-[2-[6-(difluoromethoxy)-8-fluoro-1-oxo-3,4-dihydroisoquinolin-2-yl]-3-(hydroxymethyl)-4-pyridyl]-1-methyl-2-oxo-3-pyridyl]cyclopropanecarboxamide | 528.48 | 0.234 | >5.4 |

TABLE 2-continued

| No. | Structure | IUPAC Name | MW | BTK LC3K (Ki) | CD69 Hu Blood FACS (IC50) |
|---|---|---|---|---|---|
| 145 | 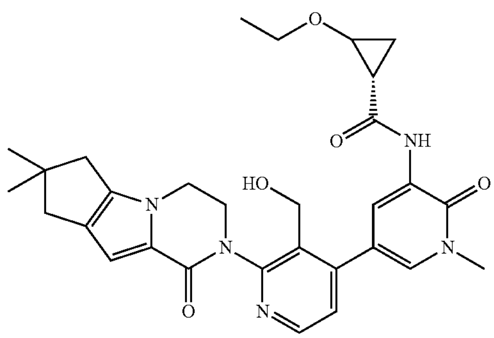 | (1S)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-ethoxy-cyclopropanecarboxamide | 545.629 | 0.011 | 0.636 |
| 146 | 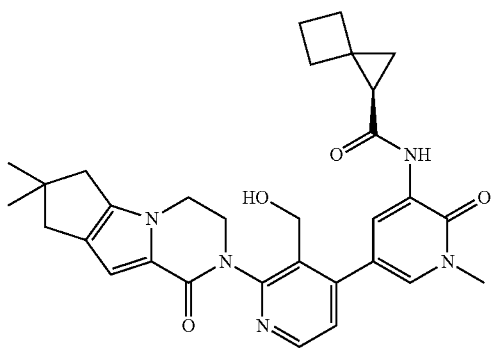 | (R)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.3]hexane-2-carboxamide | 541.641 | 0.017 | 5.2 |
| 147 | 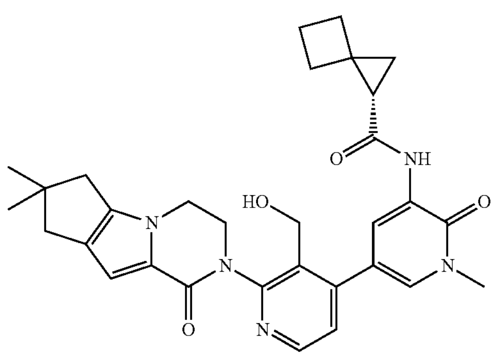 | (S)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.3]hexane-2-carboxamide | 541.641 | 0.0048 | 0.91 |
| 148 | 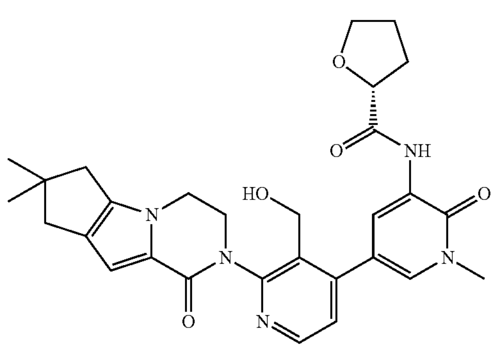 | (2R)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]tetrahydrofuran-2-carboxamide | 531.603 | >0.50 | >6.1 |

TABLE 2-continued

| No. | Structure | IUPAC Name | MW | BTK LC3K (Ki) | CD69 Hu Blood FACS (IC50) |
|---|---|---|---|---|---|
| 149 | 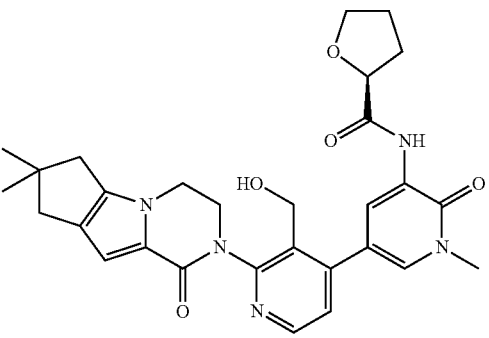 | (2S)-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]tetrahydrofuran-2-carboxamide | 531.603 | 0.252 | >6.3 |
| 150 | 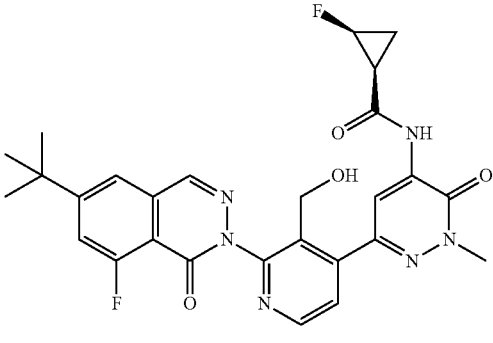 | (1S,2S)-N-[6-[2-(6-tert-butyl-8-fluoro-1-oxo-phthalazin-2-yl)-3-(hydroxymethyl)-4-pyridyl]-2-methyl-3-oxo-pyridazin-4-yl]-2-fluoro-cyclopropanecarboxamide | 536.53 | 0.0030 | 0.214 |
| 151 | 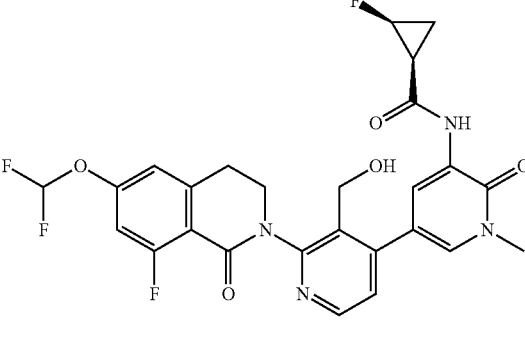 | (1S,2S)-N-[5-[2-[6-(difluoromethoxy)-8-fluoro-1-oxo-3,4-dihydroisoquinolin-2-yl]-3-(hydroxymethyl)-4-pyridyl]-1-methyl-2-oxo-3-pyridyl]-2-fluoro-cyclopropanecarboxamide | 546.47 | 0.066 | >5.3 |
| 152 | 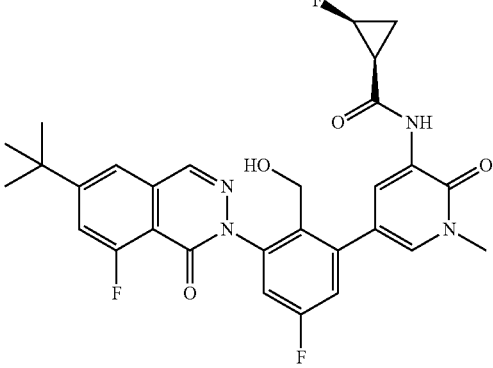 | (1S,2S)-N-[5-[3-(6-tert-butyl-8-fluoro-1-oxo-phthalazin-2-yl)-5-fluoro-2-(hydroxymethyl)phenyl]-1-methyl-2-oxo-3-pyridyl]-2-fluoro-cyclopropanecarboxamide | 552.544 | 0.00053 | 0.0368 |

TABLE 2-continued

| No. | Structure | IUPAC Name | MW | BTK LC3K (Ki) | CD69 Hu Blood FACS (IC50) |
|---|---|---|---|---|---|
| 153 | 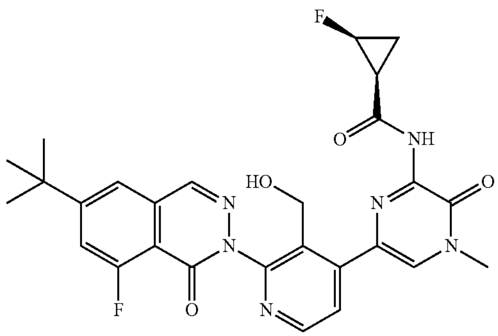 | (1S,2S)-N-[6-[2-(6-tert-butyl-8-fluoro-1-oxo-phthalazin-2-yl)-3-(hydroxymethyl)-4-pyridyl]-4-methyl-3-oxo-pyrazin-2-yl]-2-fluoro-cyclopropanecarboxamide | 536.53 | 0.013 | — |
| 154 | 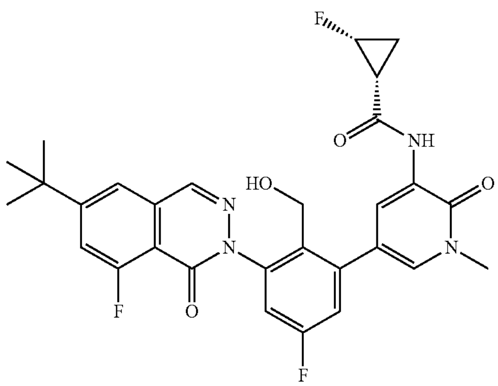 | (1R,2R)-N-[5-[3-(6-tert-butyl-8-fluoro-1-oxo-phthalazin-2-yl)-5-fluoro-2-(hydroxymethyl)phenyl]-1-methyl-2-oxo-3-pyridyl]-2-fluoro-cyclopropanecarboxamide | 552.544 | 0.00059 | 0.125 |
| 155 | 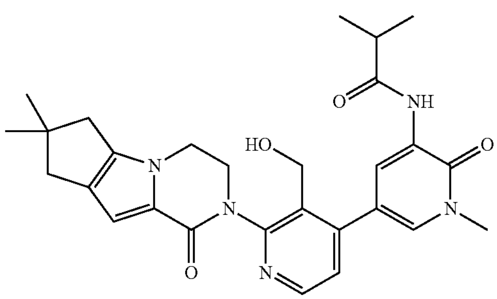 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methyl-propanamide | 503.593 | 0.098 | — |
| 156 | 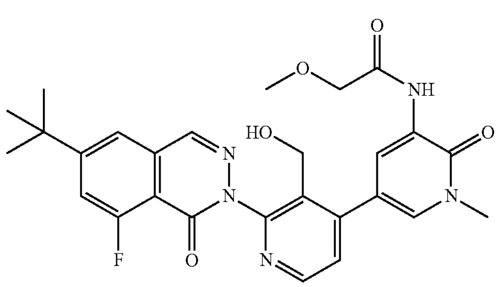 | N-[5-[2-(6-tert-butyl-8-fluoro-1-oxo-phthalazin-2-yl)-3-(hydroxymethyl)-4-pyridyl]-1-methyl-2-oxo-3-pyridyl]-2-methoxy-acetamide | 521.54 | 0.021 | >4.5 |

TABLE 2-continued

| No. | Structure | IUPAC Name | MW | BTK LC3K (Ki) | CD69 Hu Blood FACS (IC50) |
|---|---|---|---|---|---|
| 157 | 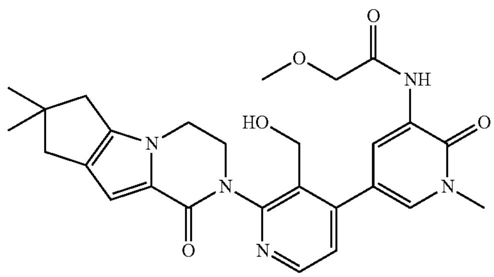 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methoxy-acetamide | 505.566 | 0.044 | >4.4 |
| 158 | 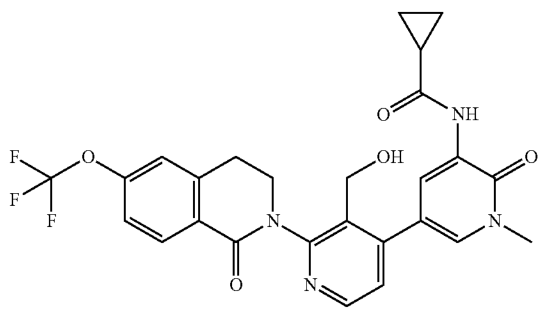 | N-[5-[3-(hydroxymethyl)-2-[1-oxo-6-(trifluoromethoxy)-3,4-dihydroisoquinolin-2-yl]-4-pyridyl]-1-methyl-2-oxo-3-pyridyl]cyclopropanecarboxamide | 528.48 | 0.262 | >4.4 |
| 159 | 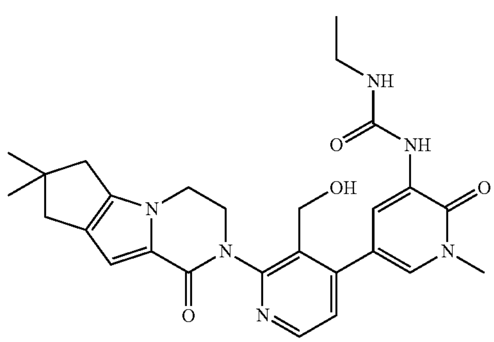 | 1-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-3-ethyl-urea | 504.581 | 0.0016 | 0.133 |
| 160 | 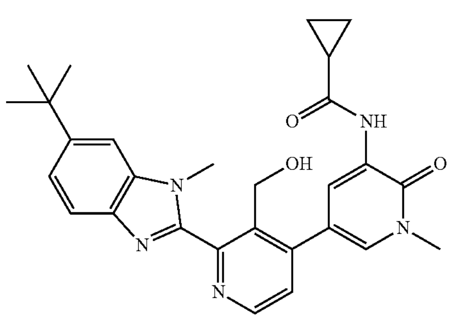 | N-[5-[2-(6-tert-butyl-1-methyl-benzimidazol-2-yl)-3-(hydroxymethyl)-4-pyridyl]-1-methyl-2-oxo-3-pyridyl]cyclopropanecarboxamide | 485.577 | 0.0257 | >3.5 |

TABLE 2-continued

| No. | Structure | IUPAC Name | MW | BTK LC3K (Ki) | CD69 Hu Blood FACS (IC50) |
|---|---|---|---|---|---|
| 161 | 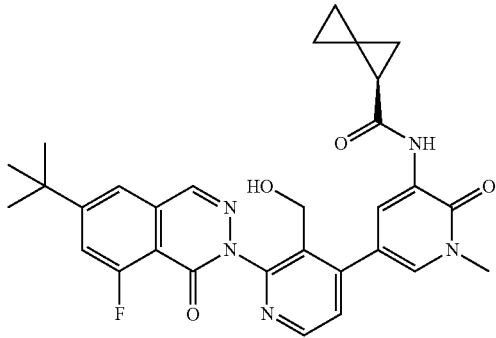 | (R)-N-[5-[2-(6-tert-butyl-8-fluoro-1-oxo-phthalazin-2-yl)-3-(hydroxymethyl)-4-pyridyl]-1-methyl-2-oxo-3-pyridyl]spiro[2.2]pentane-2-carboxamide | 543.589 | 0.0037 | 0.338 |
| 162 | 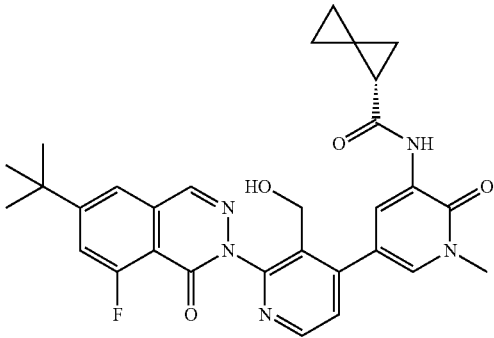 | (S)-N-[5-[2-(6-tert-butyl-8-fluoro-1-oxo-phthalazin-2-yl)-3-(hydroxymethyl)-4-pyridyl]-1-methyl-2-oxo-3-pyridyl]spiro[2.2]pentane-2-carboxamide | 543.589 | 0.0050 | 0.786 |
| 163 | 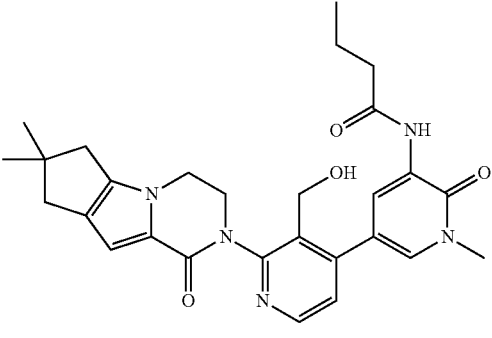 | N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]butanamide | 503.593 | 0.0328 | 1.9 |
| 164 | 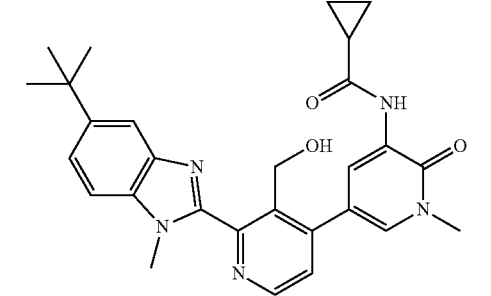 | N-[5-[2-(5-tert-butyl-1-methyl-benzimidazol-2-yl)-3-(hydroxymethyl)-4-pyridyl]-1-methyl-2-oxo-3-pyridyl]cyclopropanecarboxamide | 485.577 | >0.50 | >10.6 |

TABLE 2-continued

| No. | Structure | IUPAC Name | MW | BTK LC3K (Ki) | CD69 Hu Blood FACS (IC50) |
|---|---|---|---|---|---|
| 165 | 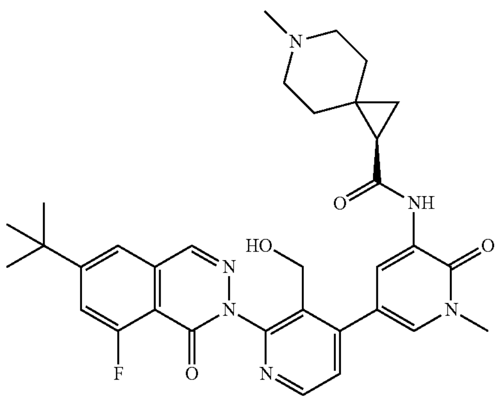 | (R)-N-[5-[2-(6-tert-butyl-8-fluoro-1-oxo-phthalazin-2-yl)-3-(hydroxymethyl)-4-pyridyl]-1-methyl-2-oxo-3-pyridyl]-6-methyl-6-azaspiro[2.5]octane-2-carboxamide | 600.683 | 0.0408 | >4.8 |
| 166 | 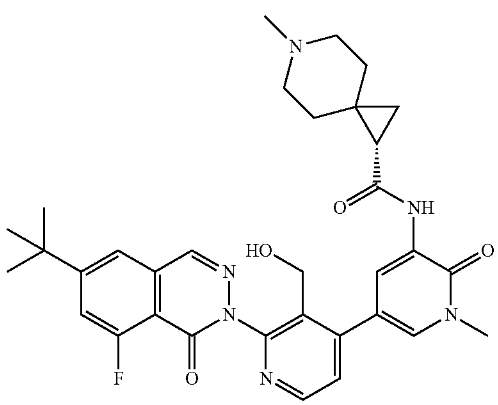 | (S)-N-[5-[2-(6-tert-butyl-8-fluoro-1-oxo-phthalazin-2-yl)-3-(hydroxymethyl)-4-pyridyl]-1-methyl-2-oxo-3-pyridyl]-6-methyl-6-azaspiro[2.5]octane-2-carboxamide | 600.683 | 0.0054 | 1.6 |
| 167 | 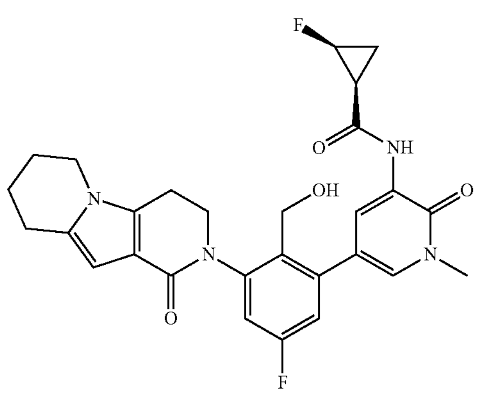 | (1S,2S)-2-fluoro-N-[5-[5-fluoro-2-(hydroxymethyl)-3-(1-oxo-3,4,6,7,8,9-hexahydropyrido[3,4-b]indolizin-2-yl)phenyl]-1-methyl-2-oxo-3-pyridyl]cyclopropanecarboxamide | 522.543 | 0.0024 | 0.245 |

TABLE 2-continued

| No. | Structure | IUPAC Name | MW | BTK LC3K (Ki) | CD69 Hu Blood FACS (IC50) |
|---|---|---|---|---|---|
| 168 | 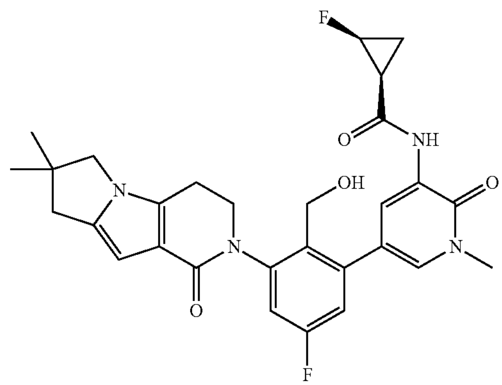 | (1S,2S)-N-[5-[3-(7,7-dimethyl-4-oxo-1,2,6,8-tetrahydropyrido[3,4-b]pyrrolizin-3-yl)-5-fluoro-2-(hydroxymethyl)phenyl]-1-methyl-2-oxo-3-pyridyl]-2-fluoro-cyclopropanecarboxamide | 536.57 | 0.0010 | 0.157 |
| 169 | 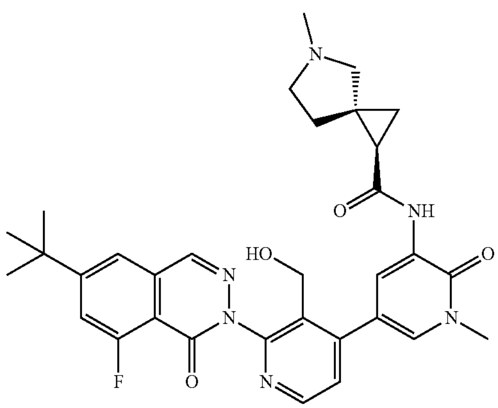 | (1R,3S)-N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide | 586.657 | 0.0384 | >4.8 |
| 170 | 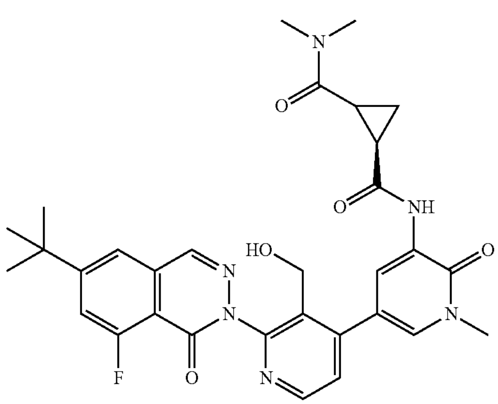 | N2-[5-[2-(6-tert-butyl-8-fluoro-1-oxo-phthalazin-2-yl)-3-(hydroxymethyl)-4-pyridyl]-1-methyl-2-oxo-3-pyridyl]-N1,N1-dimethyl-cyclopropane-1,2-dicarboxamide | 588.629 | 0.025 | >4.8 |

TABLE 2-continued

| No. | Structure | IUPAC Name | MW | BTK LC3K (Ki) | CD69 Hu Blood FACS (IC50) |
|---|---|---|---|---|---|
| 171 | 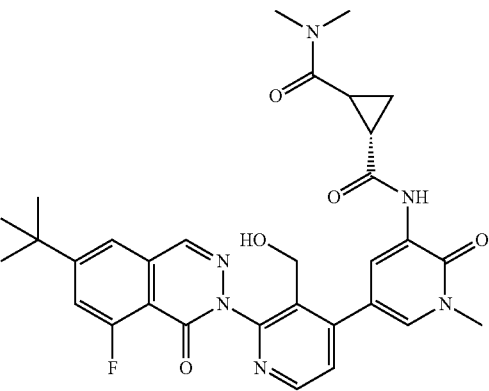 | N2-[5-[2-(6-tert-butyl-8-fluoro-1-oxo-phthalazin-2-yl)-3-(hydroxymethyl)-4-pyridyl]-1-methyl-2-oxo-3-pyridyl]-N1,N1-dimethyl-cyclopropane-1,2-dicarboxamide | 588.629 | 0.0915 | >4.8 |
| 172 | 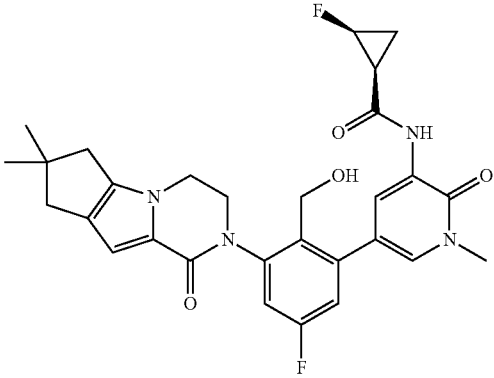 | (1S,2S)-N-[5-[3-(7,7-dimethyl-4-oxo-1,2,6,8-tetrahydrocyclopenta[3,4]pyrrole[3,5-b]pyrazin-3-yl)-5-fluoro-2-(hydroxymethyl)phenyl]-1-methyl-2-oxo-3-pyridyl]-2-fluoro-cyclopropanecarboxamide | 536.57 | 0.0008 | 0.017 |
| 173 | 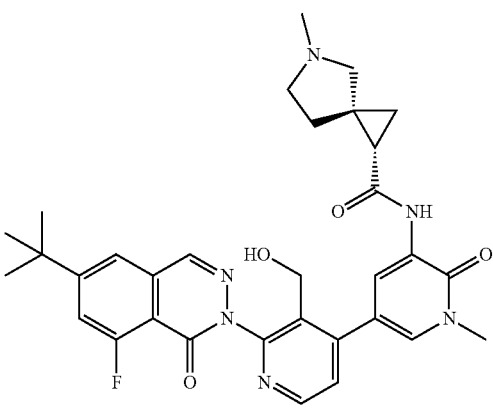 | (1S,3S)-N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide | 586.657 | 0.026 | >4.8 |

TABLE 2-continued

| No. | Structure | IUPAC Name | MW | BTK LC3K (Ki) | CD69 Hu Blood FACS (IC50) |
|---|---|---|---|---|---|
| 174 | 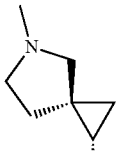 | (1S,3R)-N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide | 586.657 | 0.0072 | 1.5 |
| 175 | 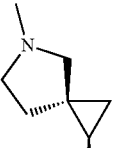 | (1R,3R)-N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide | 586.657 | 0.0076 | >4.8 |
| 176 | 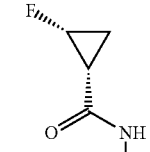 | (1R,2R)-N-[5-[3-(7,7-dimethyl-4-oxo-1,2,6,8-tetrahydrocyclopenta[3,4]pyrrole[3,5-b]pyrazin-3-yl)-5-fluoro-2-(hydroxymethyl)phenyl]-1-methyl-2-oxo-3-pyridyl]-2-fluoro-cyclopropanecarboxamide | 536.57 | 0.0021 | 0.0327 |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with Btk such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of Btk activity may result in reduced amounts of reperfusion injury in such situations.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs. The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with additional therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be a Bcl-2 inhibitor, a JAK inhibitor, an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, $3^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Experimental procedures, intermediates and reagents useful for useful for the preparation of Formula I compounds may be found in WO2011/140488; US 2012/0010191; WO2013/067274; US 2013/0116235; WO2013/067277; US 2013/0116245; WO2013/067260; US 2013/0116262; WO2013/067264; US 2013/0116246, which are incorporated by reference in its entirety.

Figure 2:
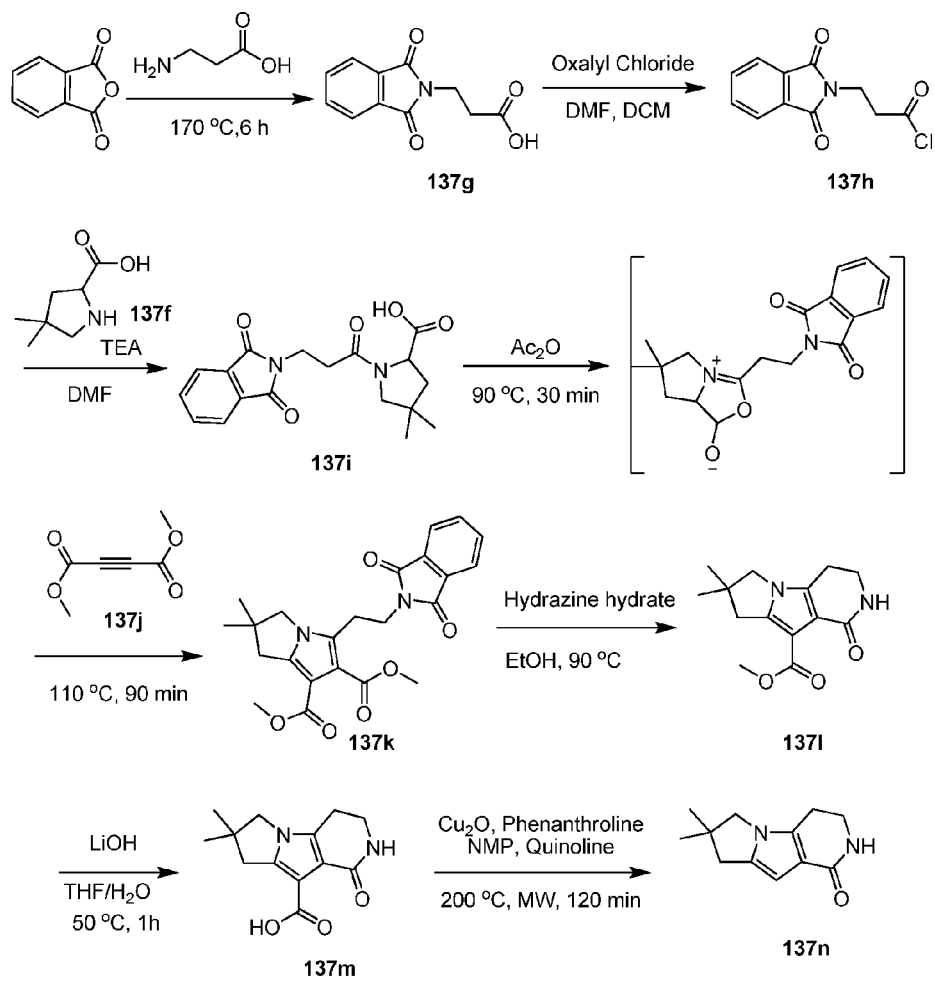
FIG. 2 shows the synthesis of 7,7-dimethyl-2,3,4,6,7,8-hexahydro-1H-pyrido[3,4-b]pyrrolizin-1-one 137n from 3-(1,3-dioxoisoindolin-2-yl)propanoic acid 137g.
Figure 3:
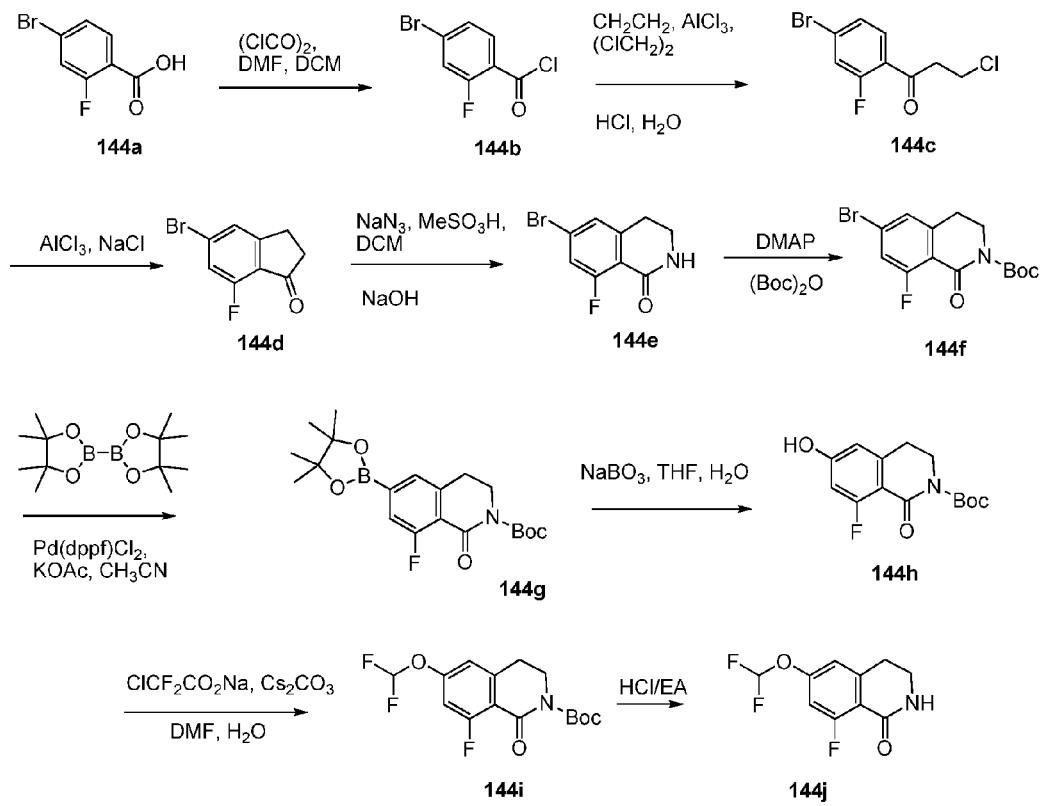
Figure 4:
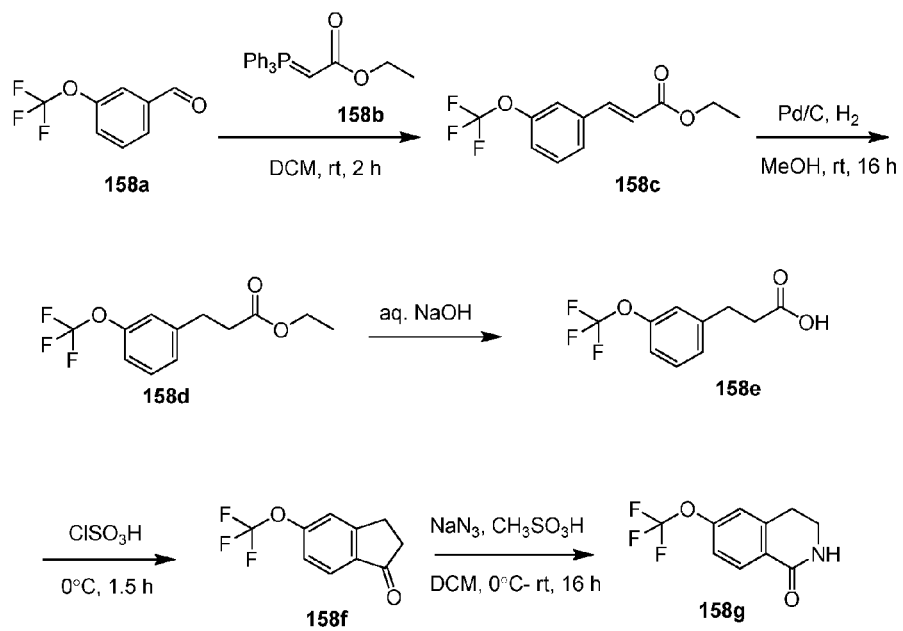
Figure 5:
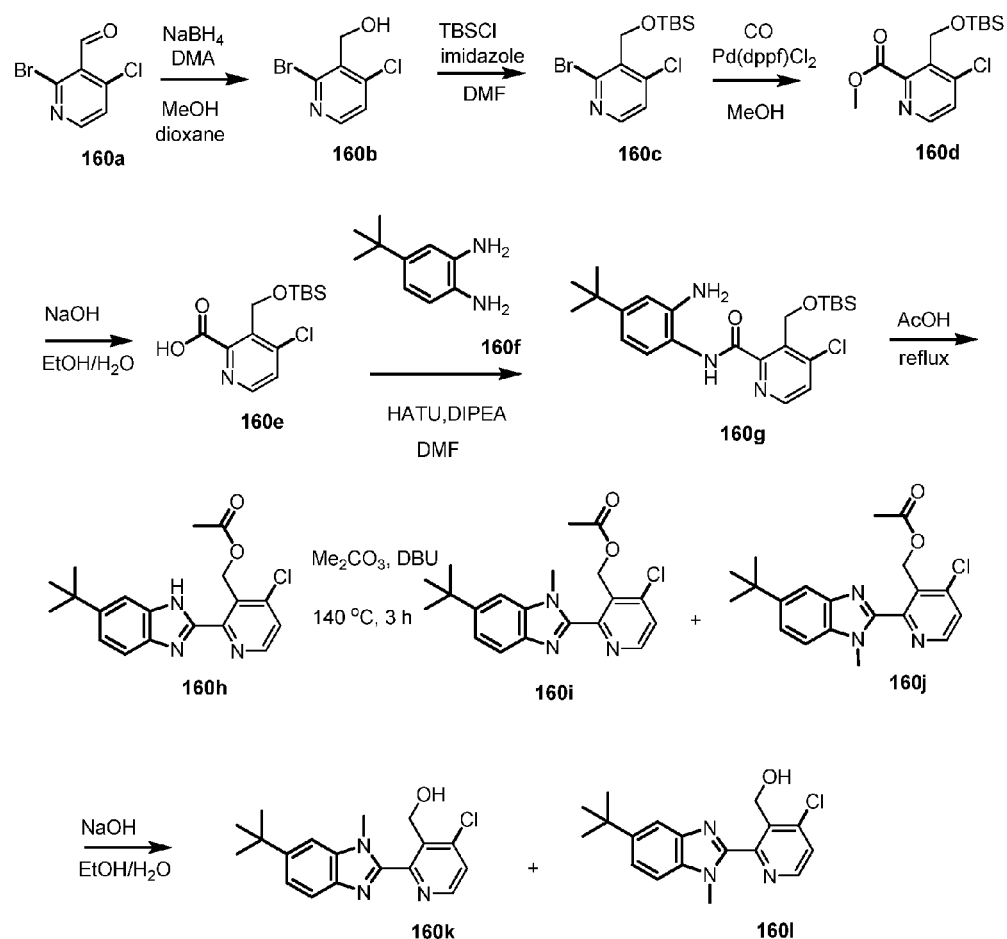
Figure 6:
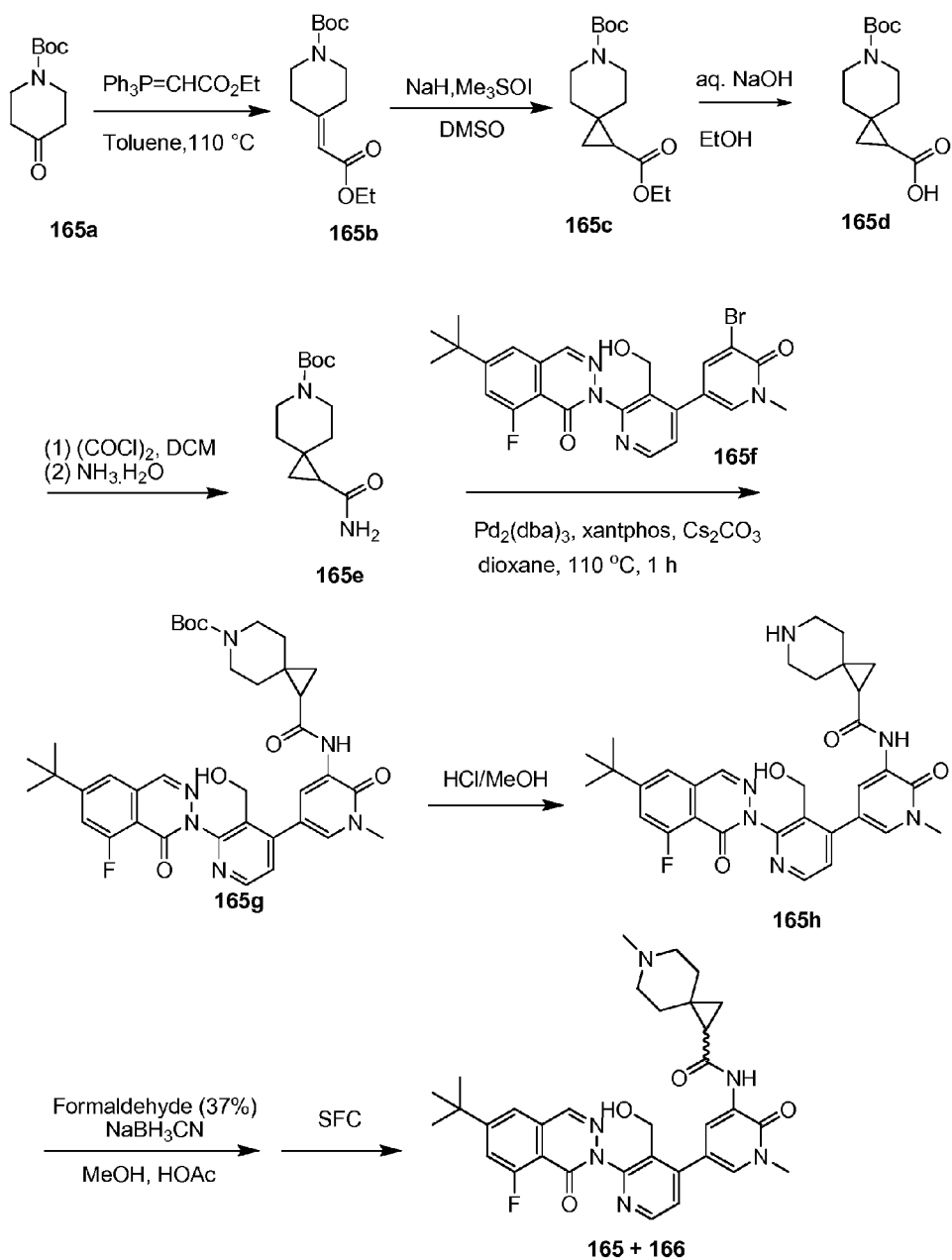

FIGS. 1-6 describe the synthesis of exemplary embodiments of Formula I compounds 101-176, more fully described in the following Examples, and may be useful for the preparation of other Formula I compounds.

General Preparative Procedures

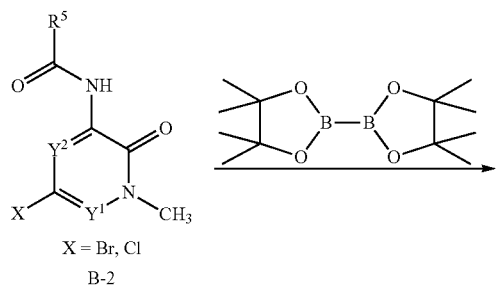

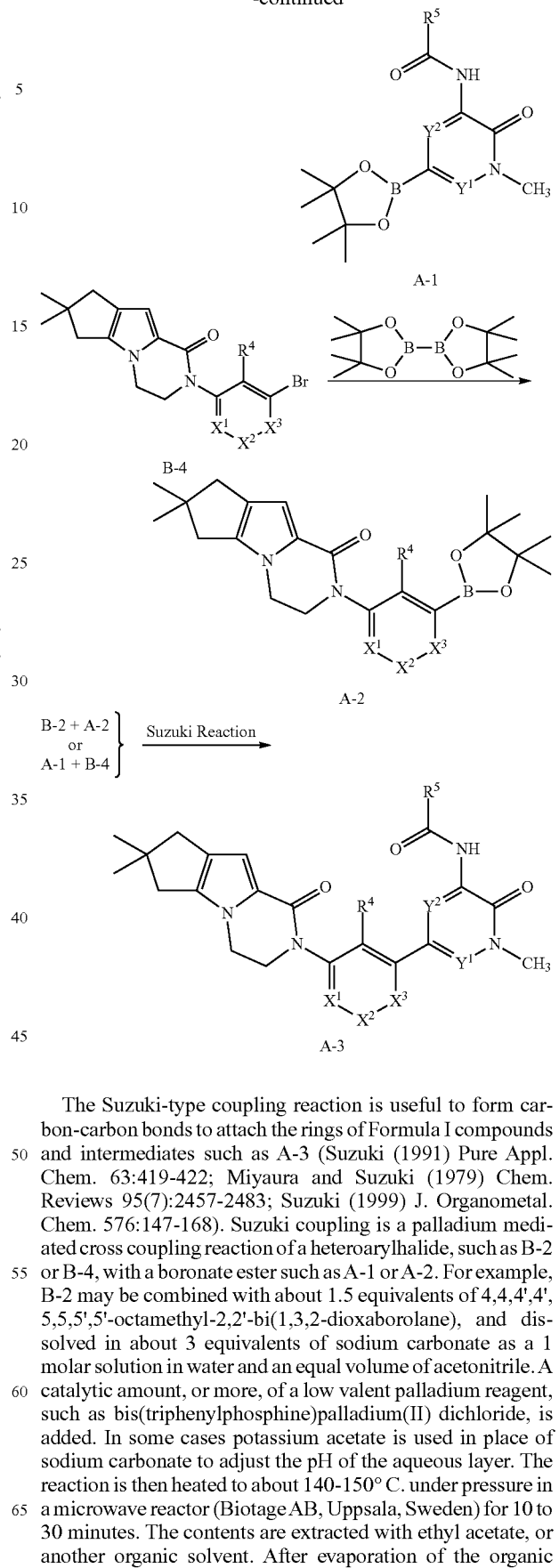

The Suzuki-type coupling reaction is useful to form carbon-carbon bonds to attach the rings of Formula I compounds and intermediates such as A-3 (Suzuki (1991) Pure Appl. Chem. 63:419-422; Miyaura and Suzuki (1979) Chem. Reviews 95(7):2457-2483; Suzuki (1999) J. Organometal. Chem. 576:147-168). Suzuki coupling is a palladium mediated cross coupling reaction of a heteroarylhalide, such as B-2 or B-4, with a boronate ester such as A-1 or A-2. For example, B-2 may be combined with about 1.5 equivalents of 4,4,4',4', 5,5,5',5'-octamethyl-2,2'-bi(1,3,2-dioxaborolane), and dissolved in about 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. In some cases potassium acetate is used in place of sodium carbonate to adjust the pH of the aqueous layer. The reaction is then heated to about 140-150° C. under pressure in a microwave reactor (Biotage AB, Uppsala, Sweden) for 10 to 30 minutes. The contents are extracted with ethyl acetate, or another organic solvent. After evaporation of the organic layer the boron ester A-1 may be purified on silica or by reverse phase HPLC. Substituents are as defined, or protected forms or precursors thereof. Likewise, bromide intermediate B-4 can be boronylated to give A-2.

Suzuki coupling of B-2 and A-2, or of A-1 and B-4, gives Formula I compound or intermediate A-3. Boronic ester (or acid) (1.5 eq) A-1 or A-2, and a palladium catalyst such as bis(triphenylphosphine)palladium(II) chloride (0.05 eq) is added to a mixture of halo intermediate (1 eq) B-2 or B-4 in acetonitrile and 1 M of sodium carbonate aqueous solution (equal volume as acetonitrile). The reaction mixture is heated to about 150° C. in a microwave for about 15 min. LC/MS indicates whether the reaction is complete or requires further time or reagents. Water is added to the mixture, and the precipitated product is filtered and purified by HPLC to yield the product A-3. Substituents may be as defined, or protected forms or precursors thereof.

A variety of low valent, Pd(II) and Pd(0) palladium catalysts, precatalysts, and ligands can be used during the Suzuki or Suzuki/Miyaura coupling step (Miyaura, N. (2002) Top. Curr. Chem., 219:11-59; Kotha, S. et al (2002) Tetrahedron, 58:9633-9695; Bellina, F. et al (2004) Synthesis, 15:2419-2440; Hassan, J. et al (2002) Chem. Rev. 102:1359-1470; Littke, A. F. et al (2002) Angew. Chem., Int. Ed. 41:4176-4211; Barder, T. E. et al (2005) J. Am. Chem. Soc., 127:4685-4696; Walker, S. D. et al (2004) Angew. Chem., Int. Ed., 43:1871-1876; Yin, J. et al (2002) J. Am. Chem. Soc., 124: 1162-1163), including $PdCl2\{PtBu_2(p-R-Ph)\}_2$ (Guram et al (2006) Organic Letters 8(9):1787-1789), $PdCl_2(PPh_3)_2$, $Pd(t-Bu)_3$, $PdCl_2$ $dppfCH_2Cl_2$, $Pd(PPh_3)_4$, $Pd(OAc)_2/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II) EnCat™ BINAP30 (US 2004/0254066).

Exemplary embodiments of low valent, Pd(II) and Pd(0) palladium catalysts, precatalysts, and ligands are "Buchwald" catalysts, palladacycles, and ligands, including 2-Dicyclohexylphosphino-2,4,6-triisopropylbiphenyl (X-Phos, CAS Reg. No. 564483-18-7) and Chloro(2-dicyclohexylphosphino-2',4',6'-triisopropyl-1,1'-biphenyl)[2-(2'-amino-1,1'-biphenyl)]palladium(II) (X-Phos aminobiphenyl palladium chloride precatalyst, CAS Reg. No. 1310584-14-5), commercially available (Johnson Matthey, West Deptford, N.J.; Sigma-Aldrich Fine Chemicals, and other suppliers). See U.S. Pat. No. 7,223,879, U.S. Pat. No. 6,395,916, U.S. Pat. No. 6,307,087.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

EXAMPLES

Example 1

2,2,2-trichloro-1-(4,5,6,7-tetrahydro-1H-indol-2-yl)ethanone 1

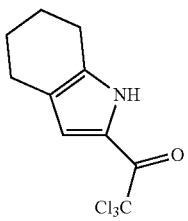

1

A 100-mL single-neck round-bottomed flask equipped with a magnetic stirrer, condenser and nitrogen inlet was purged with nitrogen and charged with 4,5,6,7-tetrahydro-1H-indole (3.00 g, 24.8 mmol), trichloroacetyl chloride (13.5 g, 74.4 mmol) and 1,2-dichloroethane (50 mL). The solution was stirred at 85° C. for 2 h. After that time, the reaction mixture was concentrated under reduced pressure to afford a 100% yield (6.50 g) of 2,2,2-trichloro-1-(4,5,6,7-tetrahydro-1H-indol-2-yl)ethanone 1 as a black semi-solid: $^1$H NMR (500 MHz, DMSO-d$_6$) δ 11.94 (s, 1H), 7.05 (s, 1H), 2.62 (t, 2H, J=6.0 Hz), 2.47 (t, 2H, J=6.0 Hz), 1.80 (m, 2H), 1.65 (m, 2H); MS (ESI+) m/z 266.0 (M+H)

Example 102

Ethyl 4,5,6,7-Tetrahydro-1H-indole-2-carboxylate 2

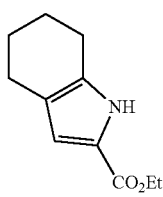

2

A 100-mL single-neck round-bottomed flask equipped with a magnetic stirrer and nitrogen inlet was purged with nitrogen and charged with 101 (6.50 g, 24.8 mmol), sodium ethoxide (17.0 mg, 0.25 mmol) and ethanol (40 mL). The solution was stirred at room temperature for 1 h. After that time, the reaction mixture was concentrated under reduced pressure. The residue was purified by column chromatography to afford a 100% yield (4.80 g) of ethyl 4,5,6,7-tetrahydro-1H-indole-2-carboxylate 2 as a brown solid: mp 70-72° C.; $^1$H NMR (300 MHz, CDCl$_3$) δ 9.08 (s, 1H), 6.75 (s, 1H), 4.25 (q, 2H, J=7.2 Hz), 2.65 (t, 2H, J=6.0 Hz), 2.56 (t, 2H, J=6.0 Hz), 1.85 (m, 4H), 1.28 (t, 3H, J=7.2 Hz); MS (ESI+) m/z 194.1 (M+H)

Example 3

Ethyl 1-(Cyanomethyl)-4,5,6,7-tetrahydro-1H-indole-2-carboxylate 3

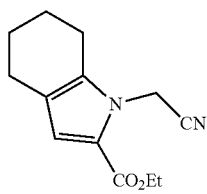

3

A 125-mL single-neck round-bottomed flask equipped with a magnetic stirrer and nitrogen inlet was purged with nitrogen and charged with 2 (5.76 g, 29.8 mmol) and DMF (50 mL). The solution was cooled to 0° C. using an ice bath. NaH (60% dispersion in mineral oil, 1.43 g, 35.8 mmol) was added. The resulting mixture was stirred at room temperature for 1 h. After that time, bromoacetonitrile (1.43 g, 35.8 mmol) was added. The mixture was stirred at room temperature for 14 h. After that time, the reaction mixture was concentrated under reduced pressure and the residue was partitioned between ethyl acetate (150 mL) and water (450 mL). The organic layer was separated, and the aqueous layer was extracted with ethyl acetate (3×150 mL). The combined organic layers were washed with brine, dried over sodium sulfate and concentrated under reduced pressure. The residue was purified by column chromatography to afford a 55% yield (3.80 g) of ethyl 1-(cyanomethyl)-4,5,6,7-tetrahydro-1H-indole-2-carboxylate 3 as a yellow semi-solid: $^1$H NMR (300 MHz, CDCl$_3$) δ 6.66 (s, 1H), 5.29 (s, 2H), 4.28 (q, 2H, J=7.2 Hz), 2.62 (t, 2H, J=6.3 Hz), 2.49 (t, 2H, J=6.3 Hz), 1.92 (m, 2H), 1.75 (m, 2H), 1.33 (t, 3H, J=7.2 Hz); MS (ESI+) m/z 233.1 (M+H)

Example 4

Ethyl 1-(2-Aminoethyl)-4,5,6,7-tetrahydro-1H-indole-2-carboxylate 4

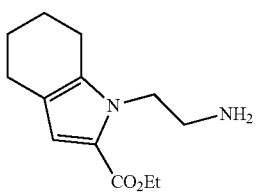

A 200-mL Parr reactor bottle was purged with nitrogen and charged with 10% palladium on carbon (50% wet, 1.28 g dry weight), 3 (3.00 g, 12.9 mmol), 12% hydrochloric acid (6.5 mL, 25 mmol), ethyl acetate (60 mL) and ethanol (40 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. diatomaceous earth filter agent (CELITE®, Imerys Minerals California, Inc.) CELITE® 521 (4.0 g) was added, and the mixture was filtered through a pad of CELITE® 521. The filter cake was washed with ethanol (2×20 mL), and the combined filtrates were concentrated to dryness under reduced pressure. The residue was partitioned between ethyl acetate (150 mL) and 10% aqueous potassium carbonate (100 mL). The organic layer was separated, and the aqueous layer was extracted with ethyl acetate (3×75 mL). The combined organic layers were dried over sodium sulfate and concentrated under reduced pressure. The residue was triturated with ethanol (5 mL) to afford a 71% yield (1.71 g) of ethyl 1-(2-aminoethyl)-4,5,6,7-tetrahydro-1H-indole-2-carboxylate 4 as a white solid: mp 102-104° C.; $^1$H NMR (500 MHz, DMSO-d$_6$) δ 6.61 (s, 1H), 6.22 (br, 2H), 4.15 (m, 4H), 2.77 (m, 2H), 2.59 (t, 2H, J=6.5 Hz), 2.42 (t, 2H, J=6.5 Hz), 1.70 (m, 2H), 1.62 (m, 2H), 1.23 (t, 3H, J=7.0 Hz); MS (APCI+) m/z 237.2 (M+H)

Example 5

3,4,6,7,8,9-Hexahydropyrazino[1,2-a]indol-1(2H)-one 5

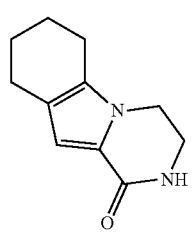

A 100-mL single-neck round-bottomed flask equipped with a magnetic stirrer and nitrogen inlet was purged with nitrogen and charged with 4 (1.80 g, 7.63 mmol), sodium ethoxide (1.55 g, 22.8 mmol) and ethanol (50 mL). The mixture was stirred at 55° C. for 5 h. After that time, the reaction mixture was concentrated under reduced pressure and the residue was partitioned between ethyl acetate (200 mL) and water (100 mL). The organic layer was separated, and the aqueous layer was extracted with ethyl acetate (2×100 mL). The combined organic layers were washed with brine, dried over sodium sulfate and concentrated under reduced pressure. The residue was purified by column chromatography to afford a 42% yield (605 mg) of 3,4,6,7,8,9-hexahydropyrazino[1,2-a]indol-1(2H)-one 4 as a white solid: mp 207-209° C.; $^1$H NMR (500 MHz, DMSO-d$_6$) δ 7.41 (s, 1H), 6.36 (s, 1H), 3.84 (t, 2H, J=6.0 Hz), 3.42 (m, 2H), 2.51 (t, 2H, J=6.0 Hz), 2.42 (t, 2H, J=6.0 Hz), 1.76 (m, 2H), 1.65 (m, 2H); (APCI+) m/z 191.3 (M+H)

Example 6

3-Bromo-5-(1-oxo-3,4,6,7,8,9-hexahydropyrazino[1,2-a]indol-2(1H)-yl)isonicotinaldehyde 6

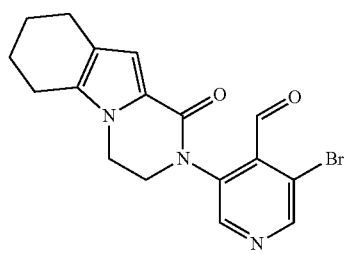

A 50-mL single-neck round-bottomed flask equipped with a magnetic stirrer and a reflux condenser was charged with 5 (300 mg, 1.57 mmol), 3,5-dibromoisonicotinaldehyde (2) (517 mg, 1.96 mmol), 4,5-bis(diphenylphosphino-9,9-dimethylxanthene (XantPhos, 120 mg, 0.2 mmol), tris(dibenzylideneacetone)dipalladium(0) (180 mg, 0.2 mmol), Cs$_2$CO$_3$ (650 mg, 2 mmol), and 1,4-dioxane (8 mL) following Buchwald reaction conditions (Wolf and Buchwald (2004) Org. Synth Coll. Vol. 10:423; Paul et al (1994) Jour. Amer. Chem. Soc. 116:5969-5970). After three cycles of vacuum/argon flush, the mixture was heated at 100° C. for 6 h. It was then cooled to room temperature and filtered. The filtrate was concentrated under reduced pressure and the resulting residue was purified by flash column chromatography eluting with DCM/MeOH (from 40:1 to 20:1) to afford 6 as a pale yellow solid (350 mg, 40%). MS: [M+H]$^+$ 374.

Example 101

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]cyclobutanecarboxamide 101

Step 1: N-(5-bromo-1-methyl-2-oxo-1,2-dihydropyridin-3-yl)cyclobutanecarboxamide 101a

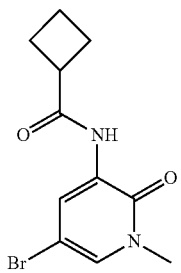

101a

To a mixture or cyclobutanecarboxylic acid (200 mg, 2.0 mmol), HATU (1.14 g, 3.0 mmol) and DIPEA (516 mg, 4.0 mmol) in DCM (8 mL) was added 3-amino-5-bromo-1-methylpyridin-2(1H)-one (330 mg, 1.62 mmol). The reaction mixture was stirred at 25° C. for 5 hours. The resulting mixture was evaporated under reduced pressure and the residue was purified on a silica-gel column eluting with 20:1 DCM/methanol to afford 101a (230 mg, 54%). MS-ESI: [M+H]$^+$ 285.1

Step 2: [4-(5-cyclobutaneamido-1-methyl-6-oxo-1,6-dihydropyridin-3-yl)-2-{4,4-dimethyl-9-oxo-1,10-diazatricyclo[6.4.0.0$^{2,6}$]dodeca-2(6),7-dien-10-yl}pyridin-3-yl]methyl acetate 101b

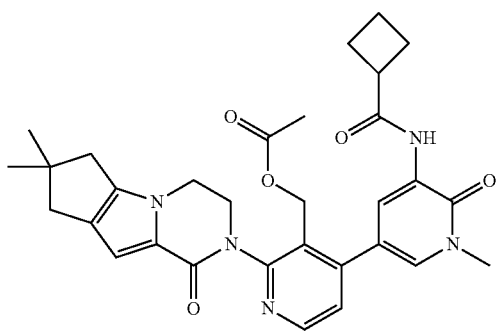

101b

A 50-mL single-neck round-bottomed flask equipped with a magnetic stirrer and a reflux condenser was charged with 101a (230 mg, 0.80 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid (320 mg, 0.80 mmol), Pd(dppf)Cl$_2$ (42 mg, 0.050 mmol), NaOAc (82 mg, 1.0 mmol), K$_3$PO$_4$.3H$_2$O (266 mg, 1.0 mmol), water (5 drops) and acetonitrile (6 mL). After three cycles of vacuum/argon flush, the mixture was heated at 100° C. for 1 h. It was then filtered and the filtrate was evaporated in vacuo. The residue was purified by silica-gel column chromatography eluting with 20:1 dichloromethane/methanol to afford 101b (200 mg, 56%) as a brown solid. MS-ESI: [M+H]$^+$ 558.3

Step 3: A mixture of 101b (200 mg, 0.36 mmol) and LiOH (34 mg, 1.4 mmol) in $^i$PrOH/THF (1:1, 4 mL) and H$_2$O (1 mL) was stirred at 40° C. for 0.5 h. The mixture was evaporated under reduced pressure. The residue was partitioned between EtOAc and water. The combined EtOAc extract was concentrated under reduced pressure and the residue was purified by reverse-phase prep-HPLC to afford 101 (80 mg, 45%) as a pale yellow solid. MS-ESI: [M+H]$^+$ 516.3. $^1$H NMR (500 MHz, DMSO-d$_6$) δ 9.10 (s, 1H), 8.48-8.47 (m, 2H), 7.73 (d, J=2.0 Hz, 1H), 7.31 (d, J=5.0 Hz, 1H), 6.56 (s, 1H), 4.95-4.94 (m, 1H), 4.44-4.40 (m, 2H), 4.23-4.18 (m, 3H), 3.86-3.84 (m, 1H), 3.57 (s, 3H), 3.57-3.50 (m, 1H), 2.58-2.55 (m, 2H), 2.42 (s, 2H), 2.20-2.07 (m, 4H), 1.94-1.88 (m, 1H), 1.80-1.77 (m, 1H), 1.21 (s, 6H).

Example 102

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl] cyclopropanecarboxamide 102

Step 1: N-(5-bromo-1-methyl-2-oxo-1,2-dihydropyridin-3-yl)cyclopropanecarboxamide 102a

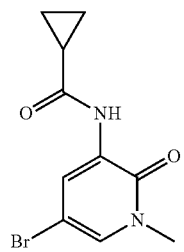

102a

To a mixture of cyclopropanecarboxylic acid (180 mg, 2.0 mmol), HATU (570 mg, 1.5 mmol) and DIPEA (390 mg, 3.0 mmol) in DCM (8 mL) was added 3-amino-5-bromo-1-methylpyridin-2(1H)-one (230 mg, 1.12 mmol). The reaction mixture was stirred at 25° C. for 5 hours. The resulting mixture was evaporated under reduced pressure and the residue was purified on a silica-gel column chromatography eluting with 20:1 DCM/methanol to afford the 102a (220 mg, 72%). MS-ESI: [M+H]$^+$ 270.1

Step 2: [4-(5-cyclopropaneamido-1-methyl-6-oxo-1,6-dihydropyridin-3-yl)-2-{4,4-dimethyl-9-oxo-1,10-diazatricyclo[6.4.0.0$^{2,6}$]dodeca-2(6),7-dien-10-yl}pyridin-3-yl]methyl acetate 102b

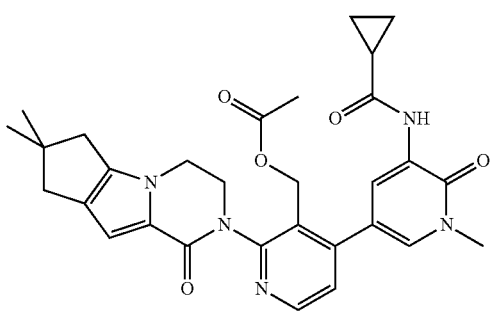

102b

A 50-mL round-bottomed flask equipped with a magnetic stirrer and a reflux condenser was charged with 102a (220 mg, 0.80 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 102c (320 mg, 0.80 mmol),

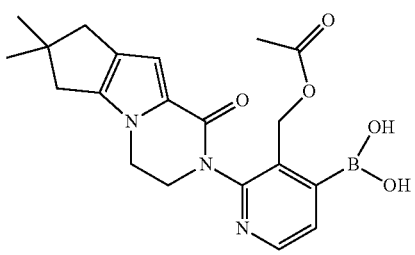

102c

Pd(dppf)Cl₂ (42 mg, 0.050 mmol), NaOAc (82 mg, 1.0 mmol), K₃PO₄.3H₂O (266 mg, 1.0 mmol), water (6 drops), and acetonitrile (6 mL). After three cycles of vacuum/argon flush, the mixture was heated at 100° C. for 1 h. It was then filtered and the filtrate was evaporated under reduced pressure. The residue was purified by silica-gel column chromatography eluting with 20:1 dichloromethane/methanol to afford 102b (150 mg, 33%) as a brown solid. MS-ESI: [M+H]⁺ 544.3

Step 3: A mixture of 102b (150 mg, 0.27 mmol) and LiOH (34 mg, 1.4 mmol) in ⁱPrOH/THF (1:1, 4 mL) and H₂O (1 mL) was stirred at 40° C. for 0.5 h. The mixture was evaporated under reduced pressure and the residue was partitioned between EtOAc and water. The combined EtOAc extract was concentrated under reduced pressure and the residue was purified by reverse-phase prep-HPLC to afford 102 (65 mg, 47%) as a pale yellow solid. MS-ESI: [M+H]⁺ 502.3. ¹H NMR (500 MHz, DMSO-d₆) δ 9.69 (s, 1H), 8.45 (d, J=5.0 Hz, 1H), 8.41 (d, J=2.0 Hz, 1H), 7.73 (d, J=2.0 Hz, 1H), 7.28 (d, J=5.0 Hz, 1H), 6.55 (s, 1H), 4.94-4.92 (m, 1H), 4.41-4.37 (m, 2H), 4.23-4.17 (m, 3H), 3.85-3.83 (m, 1H), 3.59 (s, 3H), 2.58-2.55 (m, 2H), 2.42 (s, 2H), 2.27-2.25 (m, 1H), 1.27 (s, 6H), 0.78-0.76 (m, 4H).

Example 103

2-cyclopropyl-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]acetamide 103

Step 1: (2-{4,4-dimethyl-9-oxo-1,10-diazatricyclo[6.4.0.0²,⁶]dodeca-2(6),7-dien-10-yl}-4-{5-[(diphenylmethylidene)amino]-1-methyl-6-oxo-1,6-dihydropyridin-3-yl}-pyridin-3-yl)-ethyl acetate 103a

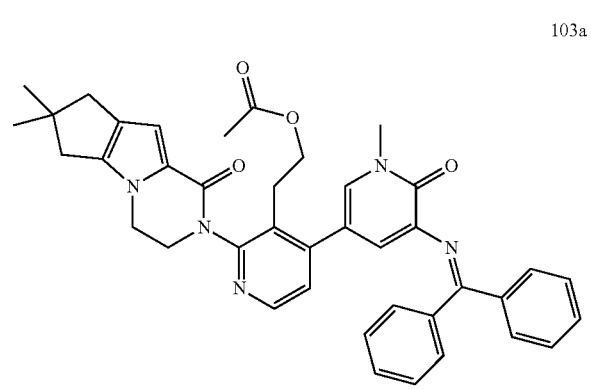

103a

A 100-mL single-neck round-bottomed flask equipped with a magnetic stirrer and a reflux condenser was charged with 5-bromo-3-[(diphenylmethylidene)amino]-1-methyl-1,2-dihydropyridin-2-one 103b (1.0 g, 2.70 mmol),

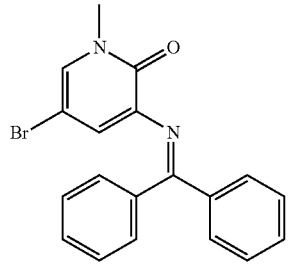

103b

{3-[(acetyloxy)methyl]-2-{4,4-dimethyl-9-oxo-1,10-diazatricyclo[6.4.0.0²,⁶]dodeca-2(6),7-dien-10-yl}pyridin-4-yl}boronic acid 102c (1.20 g, 3.00 mmol), Pd(dppf)Cl₂ (122 mg, 0.15 mmol), NaOAc (460 mg, 5.4 mmol), K₃PO₄.3H₂O (1.27 g, 5.4 mmol), H₂O (1 mL), and acetonitrile (30 mL). After three cycles of vacuum/argon flush, the mixture was heated at 80° C. for 1 h. It was then filtered and the filtrate was evaporated in vacuo. The residue was purified by silica-gel column chromatography eluting with 20:1 dichloromethane/methanol to afford 103a (800 mg, 47%) as a yellow solid. MS-ESI: [M+H]⁺ 640.3

Step 2: [4-(5-amino-1-methyl-6-oxo-1,6-dihydropyridin-3-yl)-2-{4,4-dimethyl-9-oxo-1,10-diazatricyclo[6.4.0.0²,⁶]dodeca-2(6),7-dien-10-yl}pyridin-3-yl]methyl acetate 103c

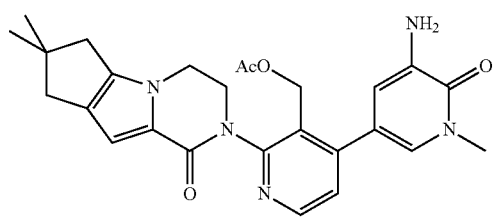

103c

A mixture of 103a (800 mg, 1.25 mmol) in HCl/dioxane (20 mL) was stirred at 0° C. for 0.5 h. The mixture was evaporated in vacuo and the residue was purified by reverse-phase prep-HPLC to afford 103c (350 mg, 60%) as a pale yellow solid. MS-ESI: [M+H]⁺ 476.1. ¹H NMR (500 MHz, DMSO-d₆) δ 8.43 (d, J=5.0 Hz, 1H), 7.09 (d, J=5.0 Hz, 1H), 6.81 (d, J=2.0 Hz, 1H), 6.77 (s, 1H), 6.57 (d, J=2.0 Hz, 1H), 6.24-6.22 (m, 1H), 5.13-5.11 (m, 1H), 4.51-4.47 (m, 1H), 4.36 (s, 2H), 4.24-4.20 (m, 1H), 4.14-4.11 (m, 1H), 4.01-3.98 (m, 1H), 3.62 (s, 3H), 2.55-2.54 (m, 2H), 2.49 (s, 2H), 1.81 (s, 3H), 1.26 (s, 6H).

Step 3: 10-[4-(5-amino-1-methyl-6-oxo-1,6-dihydropyridin-3-yl)-3-(hydroxymethyl)-pyridin-2-yl]-4,4-dimethyl-1,10-diazatricyclo[6.4.0.0²,⁶]dodeca-2(6),7-dien-9-one 103d

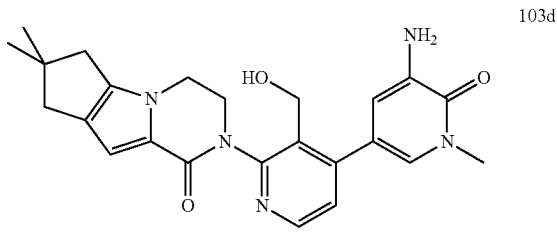

103d

A mixture of 103c (1.1 g, 2.3 mmol) and LiOH (450 mg, 11.0 mmol) in $^{i}$PrOH/THF (1:1, 10 mL) and $H_2O$ (2.5 mL) was stirred at 40° C. for 0.5 h. The mixture was evaporated in vacuo. The residue was partitioned between EtOAc and water. The combined EtOAc extract was concentrated under reduced pressure and the residue was purified by silica-gel column chromatography eluting with 10:1 dichloromethane/methanol to afford 103d (350 mg, 36%) as a pale yellow solid. MS-ESI: [M+H]$^+$ 434.3. $^1$H NMR (500 MHz, CDCl$_3$) δ 8.44 (d, J=5.0 Hz, 1H), 7.59 (d, J=2.0 Hz, 1H), 7.21 (d, J=5.0 Hz, 1H), 6.83 (s, 1H), 6.82 (d, J=2.0 Hz, 1H), 5.04-5.03 (m, 1H), 4.63-4.62 (m, 1H), 4.50-4.48 (m, 1H), 4.30-4.28 (m, 1H), 4.16-4.10 (m, 3H), 3.87-3.85 (m, 1H), 3.65 (s, 3H), 2.57-2.56 (m, 2H), 2.50 (s, 2H), 1.26 (s, 6H).

Step 4: Intermediate 103d was acylated with 2-cyclopropylacetyl chloride or the activated ester of 2-cyclopropylacetic acid to give 103. LC-MS m/z: 516.3 [M+H]$^+$. $^1$H NMR (400 MHz, DMSO-d$_6$) δ 9.27 (s, 1H), 8.51-8.44 (m, 2H), 7.73 (d, J=2.4 Hz, 1H), 7.30 (d, J=5.0 Hz, 1H), 6.56 (s, 1H), 4.93 (s, 1H), 4.42 (t, J=11.4 Hz, 2H), 4.25-4.15 (m, 3H), 3.85 (d, J=10.3 Hz, 1H), 3.59 (s, 3H), 2.57 (d, J=7.4 Hz, 2H), 2.43 (s, 2H), 2.37 (d, J=7.1 Hz, 2H), 1.22 (s, 6H), 1.08-0.96 (m, 1H), 0.56-0.46 (m, 2H), 0.26-0.17 (m, 2H).

Example 104

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl] oxetane-3-carboxamide 104

Following the procedures of Examples 101-103 and 120, 104 was prepared. LC-MS m/z: 518.3[M+1]+. $^1$H NMR (400 MHz, DMSO-d$_6$) δ 9.52 (s, 1H), 8.58-8.50 (m, 1H), 8.50-8.46 (m, 1H), 7.76 (d, J=2.4 Hz, 1H), 7.36-7.26 (m, 1H), 6.56 (s, 1H), 4.97-4.88 (m, 1H), 4.72-4.58 (m, 2H), 4.46-4.35 (m, 2H), 4.30-4.17 (m, 3H), 4.06 (q, J=5.2 Hz, 1H), 3.86 (d, J=10.4 Hz, 1H), 3.58 (d, J=1.1 Hz, 3H), 3.17 (d, J=5.2 Hz, 2H), 2.58 (d, J=7.2 Hz, 2H), 2.43 (s, 2H), 1.22 (s, 6H).

Example 105

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-morpholino-acetamide 105

Following the procedures of Examples 101-103 and 120, 105 was prepared. LC-MS m/z: 561.3 [M+1]+. $^1$H NMR (400 MHz, DMSO-d$_6$) δ 9.96 (s, 1H), 8.48 (d, J=5.0 Hz, 1H), 8.44 (d, J=2.4 Hz, 1H), 7.74 (d, J=2.4 Hz, 1H), 7.30 (d, J=5.0 Hz, 1H), 6.55 (s, 1H), 4.93 (s, 1H), 4.43-4.38 (m, 2H), 4.25-4.14 (m, 3H), 3.85 (d, J=10.3 Hz, 1H), 3.70-3.62 (m, 4H), 3.60 (s, 3H), 3.27 (s, 2H), 3.17 (s, 2H), 2.61-2.51 (m, 4H), 2.42 (s, 2H), 1.22 (s, 6H).

Example 106

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methyl-cyclopropanecarboxamide 106

Following the procedures of Examples 101-103 and 120, 106 was prepared. LC-MS m/z: 516.3 [M+1]+. $^1$H NMR (400 MHz, DMSO-d$_6$) δ 9.56 (s, 1H), 8.50-8.43 (m, 1H), 8.43-8.37 (m, 1H), 7.72 (d, J=2.4 Hz, 1H), 7.33-7.25 (m, 1H), 6.55 (s, 1H), 4.93-4.88 (m, 1H), 4.46-4.35 (m, 2H), 4.25-4.14 (m, 3H), 3.88-3.80 (m, 1H), 3.59 (s, 3H), 2.57 (d, J=7.3 Hz, 2H), 2.42 (s, 2H), 2.06-1.97 (m, 1H), 1.22 (s, 6H), 1.07 (d, J=5.9 Hz, 3H), 1.03-0.90 (m, 2H), 0.66-0.57 (m, 1H).

Example 107

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl] propanamide 107

Following the procedures of Examples 101-103 and 120, 107 was prepared. LC-MS m/z: 490.2 [M+1]+. $^1$H NMR (400 MHz, DMSO-d$_6$) δ 9.26 (s, 1H), 8.52-8.43 (m, 2H), 7.72 (d, J=2.4 Hz, 1H), 7.30 (d, J=5.1 Hz, 1H), 6.56 (s, 1H), 4.92 (t, J=5.1 Hz, 1H), 4.44-4.36 (m, 2H), 4.27-4.14 (m, 3H), 3.90-3.81 (m, 1H), 3.58 (s, 3H), 2.57 (d, J=7.3 Hz, 2H), 2.49-2.44 (m, 2H), 2.43 (s, 2H), 1.22 (s, 6H), 1.05 (t, J=7.5 Hz, 3H).

Example 108

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-(3,5-dimethylpyrazol-1-yl)acetamide 108

Following the procedures of Examples 101-103 and 120, 108 was prepared. LC-MS m/z: 570.3 [M+1]+. $^1$H NMR (400 MHz, DMSO-d$_6$) δ 9.54 (s, 1H), 8.46 (d, J=5.0 Hz, 1H), 8.44 (d, J=2.4 Hz, 1H), 7.76 (d, J=2.4 Hz, 1H), 7.29 (d, J=5.1 Hz, 1H), 6.55 (s, 1H), 5.85 (s, 1H), 4.98 (s, 2H), 4.92 (s, 1H), 4.42-4.34 (m, 2H), 4.22-4.14 (m, 3H), 3.84 (d, J=10.2 Hz, 1H), 3.58 (s, 3H), 2.61-2.51 (m, 2H), 2.42 (s, 2H), 2.17 (s, 3H), 2.10 (s, 3H), 1.22 (s, 6H).

Example 109

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl] pyridine-3-carboxamide 109

Following the procedures of Examples 101-103 and 120, 109 was prepared. LC-MS m/z: 539.3 [M+1]+. $^1$H NMR (400 MHz, DMSO-d$_6$) δ 9.71 (s, 1H), 9.08 (d, J=2.1 Hz, 1H), 8.77 (dd, J=4.8, 1.6 Hz, 1H), 8.54-8.47 (m, 2H), 8.33-8.25 (m, 1H), 7.86 (d, J=2.4 Hz, 1H), 7.62-7.53 (m, 1H), 7.36 (d, J=5.0 Hz, 1H), 6.56 (s, 1H), 4.99 (s, 1H), 4.51-4.37 (m, 2H), 4.32-4.16 (m, 3H), 3.87 (d, J=10.3 Hz, 1H), 3.63 (s, 3H), 2.58 (d, J=7.4 Hz, 2H), 2.43 (s, 2H), 1.22 (s, 6H).

Example 110

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-1-methyl-pyrazole-4-carboxamide 110

Following the procedures of Examples 101-103 and 120, 110 was prepared. LC-MS m/z: 542.3 [M+1]+. $^1$H NMR (400 MHz, DMSO-d$_6$) δ 9.02 (s, 1H), 8.49 (d, J=5.0 Hz, 1H), 8.45 (d, J=2.4 Hz, 1H), 8.43 (s, 1H), 7.98 (d, J=0.8 Hz, 1H), 7.78 (d, J=2.4 Hz, 1H), 7.34 (d, J=5.0 Hz, 1H), 6.56 (s, 1H), 4.96 (t, J=5.3 Hz, 1H), 4.47-4.38 (m, 2H), 4.28-4.15 (m, 3H), 3.89 (s, 3H), 3.88-3.82 (m, 1H), 3.62 (s, 3H), 2.58 (d, J=7.5 Hz, 2H), 2.43 (s, 2H), 1.22 (s, 6H).

Example 111

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-5-methyl-1H-pyrazole-3-carboxamide 111

Following the procedures of Examples 101-103 and 120, 111 was prepared. LC-MS m/z: 542.3 [M+1]+. $^1$H NMR (400 MHz, DMSO-d$_6$) δ 13.19 (s, 1H), 9.72 (s, 1H), 8.56 (d, J=2.4 Hz, 1H), 8.49 (d, J=5.0 Hz, 1H), 7.75 (d, J=2.4 Hz, 1H), 7.34 (d, J=5.0 Hz, 1H), 6.56 (s, 1H), 6.51 (s, 1H), 4.95 (t, J=5.3 Hz, 1H), 4.47-4.38 (m, 2H), 4.31-4.15 (m, 3H), 3.92-3.83 (m, 1H), 3.62 (s, 3H), 2.58 (d, J=7.3 Hz, 2H), 2.43 (s, 2H), 2.30 (s, 3H), 1.22 (s, 6H).

Example 112

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-1,5-dimethyl-pyrazole-3-carboxamide 112

Following the procedures of Examples 101-103 and 120, 112 was prepared. LC-MS m/z: 556.3 [M+1]+. $^1$H NMR (400 MHz, DMSO-d$_6$) δ 9.61 (s, 1H), 8.55 (d, J=2.4 Hz, 1H), 8.49 (d, J=5.0 Hz, 1H), 7.75 (d, J=2.4 Hz, 1H), 7.34 (d, J=5.1 Hz, 1H), 6.59-6.53 (m, 2H), 4.99-4.91 (m, 1H), 4.47-4.38 (m, 2H), 4.28-4.15 (m, 3H), 3.88 (s, 1H), 3.85 (s, 3H), 3.62 (s, 3H), 2.58 (d, J=7.5 Hz, 2H), 2.43 (s, 2H), 2.31 (s, 3H), 1.22 (s, 6H).

Example 113

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-6-pyrrolidin-1-yl-pyridine-3-carboxamide 113

Following the procedures of Examples 101-103 and 120, 113 was prepared. LC-MS m/z: 608.3 [M+1]+. $^1$H NMR (400 MHz, DMSO-d$_6$) δ 9.20 (s, 1H), 8.66 (d, J=2.5 Hz, 1H), 8.53-8.46 (m, 2H), 7.97 (dd, J=8.9, 2.5 Hz, 1H), 7.79 (d, J=2.4 Hz, 1H), 7.35 (d, J=5.0 Hz, 1H), 6.59-6.50 (m, 2H), 4.96 (t, J=5.3 Hz, 1H), 4.48-4.39 (m, 2H), 4.26-4.15 (m, 3H), 3.86 (d, J=10.2 Hz, 1H), 3.63 (s, 3H), 3.46 (d, J=6.7 Hz, 4H), 2.58 (d, J=7.4 Hz, 2H), 2.43 (s, 2H), 2.01-1.93 (m, 4H), 1.22 (s, 6H).

Example 114

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]benzamide 114

Following the procedures of Examples 101-103 and 120, 114 was prepared. LC-MS m/z: 538.3 [M+1]+. $^1$H NMR (400 MHz, DMSO-d$_6$) δ 9.42 (s, 1H), 8.54 (d, J=2.4 Hz, 1H), 8.50 (d, J=5.1 Hz, 1H), 7.97-7.90 (m, 2H), 7.83 (d, J=2.4 Hz, 1H), 7.68-7.60 (m, 1H), 7.60-7.52 (m, 2H), 7.36 (d, J=5.0 Hz, 1H), 6.57 (s, 1H), 4.98 (t, J=5.3 Hz, 1H), 4.48-4.39 (m, 2H), 4.24-4.17 (m, 3H), 3.87 (d, J=10.8 Hz, 1H), 3.64 (s, 3H), 2.58 (d, J=7.5 Hz, 2H), 2.43 (s, 2H), 1.22 (s, 6H).

Example 115

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]oxazole-5-carboxamide 115

Following the procedures of Examples 101-103 and 120, 115 was prepared. LC-MS m/z: 529.2 [M+1]+. $^1$H NMR (400 MHz, DMSO-d$_6$) δ 9.40 (s, 1H), 8.67 (s, 1H), 8.50 (d, J=5.0 Hz, 1H), 8.48 (d, J=2.4 Hz, 1H), 8.04 (s, 1H), 7.85 (d, J=2.4 Hz, 1H), 7.35 (d, J=5.0 Hz, 1H), 6.56 (s, 1H), 4.97 (t, J=5.3 Hz, 1H), 4.46-4.37 (m, 2H), 4.26-4.15 (m, 3H), 3.86 (d, J=10.6 Hz, 1H), 3.63 (s, 3H), 2.58 (d, J=7.5 Hz, 2H), 2.43 (s, 2H), 1.22 (s, 6H).

Example 116

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2,2-difluoro-cyclopropanecarboxamide 116

Following the procedures of Examples 101-103 and 120, 116 was prepared. LC-MS m/z: 538.3 [M+1]+. $^1$H NMR (400 MHz, DMSO-d$_6$) δ 10.04 (s, 1H), 8.47 (d, J=5.1 Hz, 1H), 8.43 (d, J=2.4 Hz, 1H), 7.78 (d, J=2.4 Hz, 1H), 7.30 (d, J=5.0 Hz, 1H), 6.55 (s, 1H), 4.92 (t, J=5.3 Hz, 1H), 4.44-4.35 (m, 2H), 4.25-4.14 (m, 3H), 3.85 (d, J=9.8 Hz, 1H), 3.60 (s, 3H), 3.42-3.31 (m, 1H), 2.57 (d, J=7.2 Hz, 2H), 2.42 (s, 2H), 2.03-1.91 (m, 2H), 1.22 (s, 6H).

Example 117

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide 117

Following the procedures of Examples 101-103 and 120, 117 was prepared. LC-MS m/z: 520.3 [M+1]+. $^1$H NMR (400 MHz, DMSO-d$_6$) δ 9.97 (s, 1H), 8.46 (d, J=5.1 Hz, 1H), 8.38 (d, J=2.3 Hz, 1H), 7.75 (d, J=2.4 Hz, 1H), 7.28 (d, J=5.1 Hz, 1H), 6.55 (s, 1H), 4.94-4.87 (m, 1H), 4.75 (s, 1H), 4.44-4.34 (m, 2H), 4.24-4.14 (m, 3H), 3.84 (d, J=10.4 Hz, 1H), 3.59 (s, 3H), 2.96-2.87 (m, 1H), 2.57 (d, J=7.1 Hz, 4H), 2.42 (s, 2H), 1.53-1.38 (m, 1H), 1.22 (s, 6H).

Example 118

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide 118

Following the procedures of Examples 101-103 and 120, 118 was prepared. LC-MS m/z: 520.3 [M+1]+. $^1$H NMR (400 MHz, DMSO-$d_6$) δ 9.97 (s, 1H), 8.46 (d, J=5.0 Hz, 1H), 8.38 (d, J=2.4 Hz, 1H), 7.75 (d, J=2.4 Hz, 1H), 7.28 (d, J=5.1 Hz, 1H), 6.55 (s, 1H), 4.91 (t, J=5.3 Hz, 1H), 4.75 (s, 1H), 4.44-4.32 (m, 2H), 4.26-4.14 (m, 3H), 3.84 (d, J=10.3 Hz, 1H), 3.59 (s, 3H), 2.98-2.87 (m, 1H), 2.57 (d, J=7.2 Hz, 4H), 2.42 (s, 2H), 1.53-1.38 (m, 1H), 1.22 (s, 6H).

Example 119

(1R,2R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide 119

Following the procedures of Examples 101-103 and 120, 119 was prepared. LC-MS m/z: 520.3 [M+1]+. $^1$H NMR (400 MHz, DMSO-$d_6$) δ 9.69 (s, 1H), 8.47 (d, J=5.1 Hz, 1H), 8.43 (d, J=2.4 Hz, 1H), 7.74 (d, J=2.4 Hz, 1H), 7.30 (d, J=5.0 Hz, 1H), 6.56 (s, 1H), 4.93 (t, J=5.3 Hz, 2H), 5.04-4.71 (m, 1H), 4.45-4.36 (m, 2H), 4.25-4.15 (m, 3H), 3.85 (d, J=10.5 Hz, 1H), 3.60 (s, 3H), 2.57 (d, J=7.2 Hz, 2H), 2.43 (s, 2H), 1.66-1.54 (m, 1H), 1.22 (s, 6H), 1.21-1.08 (m, 1H).

Example 120

(1S,2S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide 120

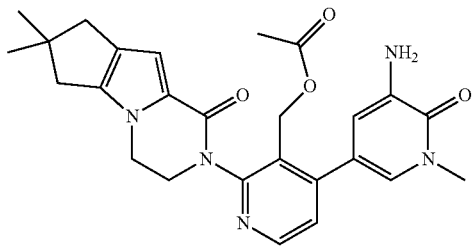

120a

A solution of (5-amino-2'-(7,7-dimethyl-1-oxo-3,4,7,8-tetrahydro-1H-cyclopenta[4,5]pyrrolo[1,2-a]pyrazin-2(6H)-yl)-1-methyl-6-oxo-1,6-dihydro[3,4'-bipyridin]-3'-yl)methyl acetate 120a (25 mg, 0.05 mmol, 1.0 equiv), (1S,2S)-2-fluorocyclopropanecarboxylic acid (7 mg, 0.065 mmol, 1.3 equiv), HATU (28 mg, 0.075 mmol, 1.5 equiv) and N,N-diisopropylethylamine (25 uL, 0.15 mmol, 3.0 equiv) in DMF (1.0 mL) was stirred at 50° C. overnight. The reaction mixture was concentrated under vacuum. A solution of crude product in THF (1 mL) was mixed with a 1M solution of sodium hydroxide in H$_2$O (1 mL) and stirred at 50° C. overnight. Reaction mixture was extracted one time with EtOAc (2 mL) and a saturated solution of ammonium chloride in H$_2$O (2 mL). The organic phase was removed, dried over sodium sulfate and passed through a filter. The resulting organic phase was concentrated under vacuum and the crude product was purified by Prep-HPLC (Column, Sunfire C18 19×150; mobile phase, CH$_3$CN:NH$_4$CO$_3$/H$_2$O (10 mmol/L)=5%-85%, 10 min; Detector, UV 254 nm) to give 14.7 mg (60%) of 120 as an off white solid. LC-MS m/z: 520.3 [M+1]+. $^1$H NMR (400 MHz, DMSO-$d_6$) δ 9.70 (s, 1H), 8.47 (d, J=5.0 Hz, 1H), 8.43 (d, J=2.4 Hz, 1H), 7.75 (d, J=2.4 Hz, 1H), 7.30 (d, J=5.1 Hz, 1H), 6.56 (s, 1H), 4.92 (t, J=5.3 Hz, 3H), 5.01-4.76 (m, 1H), 4.48-4.36 (m, 2H), 4.25-4.14 (m, 3H), 3.85 (d, J=10.1 Hz, 1H), 3.60 (s, 3H), 2.57 (d, J=7.2 Hz, 2H), 2.43 (s, 2H), 1.67-1.50 (m, 1H), 1.22 (s, 6H), 1.19-1.08 (m, 1H).

Example 121

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl] acetamide 121

Following the procedures of Example 120, 121 was prepared. LC-MS m/z: 476.3 [M+1]+. $^1$H NMR (400 MHz, DMSO-$d_6$) δ 9.37 (s, 1H), 8.47 (d, J=5.0 Hz, 1H), 8.43 (d, J=2.4 Hz, 1H), 7.72 (d, J=2.5 Hz, 1H), 7.29 (d, J=5.0 Hz, 1H), 6.55 (s, 1H), 4.92 (t, J=5.2 Hz, 1H), 4.43-4.35 (m, 2H), 4.25-4.14 (m, 3H), 3.85 (d, J=10.3 Hz, 1H), 3.58 (s, 3H), 2.57 (d, J=7.5 Hz, 2H), 2.43 (s, 2H), 2.14 (s, 3H), 1.22 (s, 6H).

Example 122

(1R,2R)—N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide 122

Following the procedures of Example 123, 122 was prepared. LC-MS m/z: 536.2 [M+1]+. $^1$H NMR (400 MHz, DMSO-$d_6$) δ 9.73 (s, 1H), 8.56 (d, J=5.0 Hz, 1H), 8.52 (d, J=2.5 Hz, 1H), 8.41 (d, J=2.4 Hz, 1H), 7.89 (d, J=1.7 Hz, 1H), 7.80-7.72 (m, 2H), 7.49 (d, J=5.0 Hz, 1H), 4.90 (t, J=5.1 Hz, 1H), 5.05-4.70 (m, 1H), 4.44-4.36 (m, 2H), 3.60 (s, 3H), 2.47-2.42 (m, 1H), 1.71-1.48 (m, 1H), 1.39 (s, 9H), 1.19-1.07 (m, 1H).

Example 123

(1S,2S)—N-[5-[2-(6-tert-butyl-8-fluoro-1-oxo-phthalazin-2-yl)-3-(hydroxymethyl)-4-pyridyl]-1-methyl-2-oxo-3-pyridyl]-2-fluoro-cyclopropanecarboxamide 123

Step 1: 5-(diphenylmethyleneamino)-1-methyl-6-oxo-1,6-dihydropyridin-3-yl-boronic acid 123a

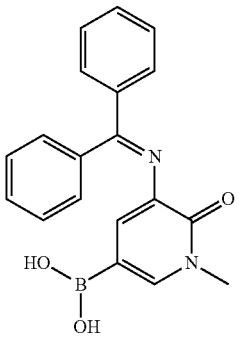

123a

A 100-mL round-bottomed flask equipped with a reflux condenser was charged with 5-bromo-3-[(diphenylmethylidene)amino]-1-methyl-1,2-dihydropyridin-2-one 103b (3.0 g, 8.1 mmol), PinB$_2$ (6.1 g, 24.0 mmol), Pd$_2$(dba)$_3$ (290 mg, 0.40 mmol), X-phos (385 mg, 0.80 mmol), KOAc (1.6 g, 16.0 mmol), and 1,4-dioxane (30 mL). After three cycles of vacuum/argon flush, the mixture was heated at 60° C. for 3 h. It was then filtered and the filtrate was evaporated under reduced pressure. The residue was washed with PE to afford 123a (2.5 g, 93%) as brown oil, which was used directly without further purification. MS-ESI: [M+H]$^+$ 333.1

Step 2: 6-tert-butyl-2-(4-(5-(diphenylmethyleneamino)-1-methyl-6-oxo-1,6-dihydropyridin-3-yl)-3-(hydroxymethyl)pyridin-2-yl)-8-fluorophthalazin-1(2H)-one 123b

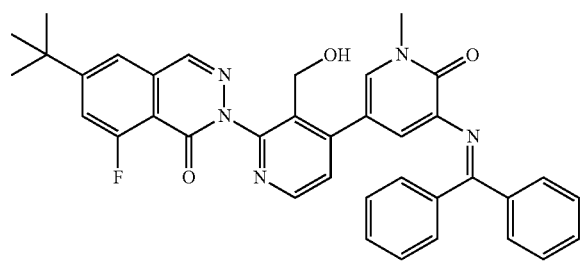

123b

A 50-mL round-bottomed flask equipped with a reflux condenser was charged with 123a (2.0 g, 6.0 mmol), 6-tert-butyl-2-(4-chloro-3-(hydroxymethyl)pyridin-2-yl)-8-fluorophthalazin-1(2H)-one 123c (2.17 g, 6.0 mmol),

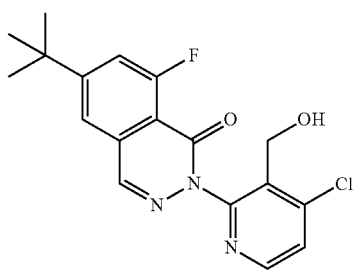

123c

K$_3$PO$_4$ (2.54 g, 12.0 mmol), NaOAc (1.0 g, 12.0 mmol), Pd(dppf)Cl$_2$ (245 mg, 0.3 mmol), and CH$_3$CN/H$_2$O (15/2 mL). The system was subject to three cycles of vacuum/argon flush and heated at 100° C. under N$_2$ protection for 2 h. LCMS analysis showed completed conversion to the desired product. The reaction mixture was cooled to room temperature and filtered. The filtrated was concentrated under reduced pressure. The residue was partitioned between DCM (20 mL) and water (10 mL). The water layer was extracted with DCM (2×10 mL). The combined organic extract was dried over Na$_2$SO$_4$, filtered, and concentrated under reduced pressure. The dark residue was purified by silica-gel column-chromatography eluting with DCM/MeOH (50:1 to 20:1) to afford 123b (1.6 g, 40%) as yellow solid. MS-ESI: [M+H]$^+$ 614.3.

Step 3: 2-(4-(5-amino-1-methyl-6-oxo-1,6-dihydropyridin-3-yl)-3-(hydroxymethyl)-pyridin-2-yl)-6-tert-butyl-8-fluorophthalazin-1(2H)-one 123d

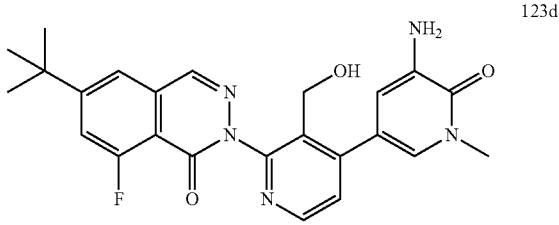

123d

A mixture of 123b (1.6 g, 2.6 mmol) in HCl/dioxane (4M, 10 mL) was stirred at 25° C. for 1 h. The mixture was evaporated in vacuo and the residue was purified by reverse-phase prep-HPLC to afford 123d (580 mg, 50%) as a pale yellow solid. MS-ESI: [M+H]$^+$ 450.1. $^1$H NMR (500 MHz, DMSO-d$_6$) δ 8.53-8.52 (m, 2H), 7.90 (d, J=1.0 Hz, 1H), 7.79-7.76 (m, 1H), 7.45 (d, J=5.0 Hz, 1H), 7.24 (d, J=2.5 Hz, 1H), 6.65 (d, J=2.0 Hz, 1H), 5.33 (s, 2H), 4.95-4.93 (m, 1H), 4.39 (s, 2H), 3.52 (s, 3H), 1.38 (s, 9H).

Step 4: A solution of 123d, (1S,2S)-2-fluorocyclopropanecarboxylic acid (15 mg, 0.14 mmol, 1.3 equiv), HATU (65 mg, 0.17 mmol, 1.5 equiv) and N,N-diisopropylethylamine (60 uL, 0.33 mmol, 3.0 equiv) in DMF (1.0 mL) was stirred at 50° C. overnight. The reaction mixture was concentrated under vacuum and the crude product was purified by Prep-HPLC (Column, Sunfire C18 19×150; mobile phase, CH$_3$CN:NH$_4$CO$_3$/H$_2$O (10 mmol/L)=5%-85%, 10 min; Detector, UV 254 nm) to give 43 mg (73%) of 123 as an off white solid. LC-MS m/z: 536.2 [M+1]+. $^1$H NMR (400 MHz, DMSO-d$_6$) δ 9.73 (s, 1H), 8.56 (d, J=5.0 Hz, 1H), 8.52 (d, J=2.5 Hz, 1H), 8.41 (d, J=2.4 Hz, 1H), 7.89 (d, J=1.7 Hz, 1H), 7.80-7.72 (m, 2H), 7.49 (d, J=5.0 Hz, 1H), 5.03-4.73 (m, 1H), 4.89 (t, J=5.2 Hz, 1H), 4.43-4.36 (m, 2H), 3.60 (s, 3H), 2.50-2.41 (m, 1H), 1.68-1.52 (m, 1H), 1.39 (s, 9H), 1.20-1.08 (m, 1H).

Example 124

N-[5-[2-(6-tert-butyl-8-fluoro-1-oxo-phthalazin-2-yl)-3-(hydroxymethyl)-4-pyridyl]-1-methyl-2-oxo-3-pyridyl]-2-fluoro-cyclopropanecarboxamide 124

Following the procedures of Example 123, 124 was prepared. LC-MS m/z: 536.2 [M+1]+. $^1$H NMR (400 MHz, DMSO-d$_6$) δ 10.00 (s, 1H), 8.55 (d, J=5.0 Hz, 1H), 8.52 (d, J=2.6 Hz, 1H), 8.35 (d, J=2.4 Hz, 1H), 7.89 (d, J=1.8 Hz, 1H), 7.80-7.72 (m, 2H), 7.46 (d, J=5.0 Hz, 1H), 4.88 (s, 1H), 4.94-4.69 (m, 1H), 4.39 (s, 3H), 3.60 (s, 3H), 2.98-2.85 (m, 1H), 1.39 (s, 9H), 1.26-1.13 (m, 1H).

Example 125

N-[5-[2-(6-tert-butyl-8-fluoro-1-oxo-phthalazin-2-yl)-3-(hydroxymethyl)-4-pyridyl]-1-methyl-2-oxo-3-pyridyl]cyclopropanecarboxamide 125

Following the procedures of Example 123, 125 was prepared. LC-MS m/z: 518.2 [M+1]+. $^1$H NMR (400 MHz, DMSO-$d_6$) δ 9.70 (s, 1H), 8.55 (d, J=5.0 Hz, 1H), 8.52 (d, J=2.5 Hz, 1H), 8.38 (d, J=2.4 Hz, 1H), 7.89 (d, J=1.8 Hz, 1H), 7.80-7.71 (m, 2H), 7.47 (d, J=5.0 Hz, 1H), 4.89 (t, J=5.0 Hz, 1H), 4.43-4.35 (m, 2H), 3.60 (s, 3H), 2.31-2.20 (m, 1H), 1.39 (s, 9H), 0.85-0.72 (m, 4H).

Example 126

N-[5-[2-(6-tert-butyl-8-fluoro-1-oxo-phthalazin-2-yl)-3-(hydroxymethyl)-4-pyridyl]-1-methyl-2-oxo-3-pyridyl]propanamide 126

Following the procedures of Example 123, 126 was prepared. LC-MS m/z: 506.2 [M+1]+. $^1$H NMR (400 MHz, DMSO-$d_6$) δ 9.28 (s, 1H), 8.56 (d, J=5.0 Hz, 1H), 8.52 (d, J=2.5 Hz, 1H), 8.43 (d, J=2.5 Hz, 1H), 7.90 (d, J=1.7 Hz, 1H), 7.81-7.70 (m, 2H), 7.48 (d, J=5.0 Hz, 1H), 4.92-4.87 (m, 1H), 4.42-4.37 (m, 2H), 3.59 (s, 3H), 2.49-2.43 (m, 2H), 1.39 (s, 9H), 1.05 (t, J=7.5 Hz, 3H).

Example 127

N-[5-[2-(6-tert-butyl-8-fluoro-1-oxo-phthalazin-2-yl)-3-(hydroxymethyl)-4-pyridyl]-1-methyl-2-oxo-3-pyridyl]acetamide 127

Following the procedures of Example 123, 127 was prepared. LC-MS m/z: 492.2 [M+1]+. $^1$H NMR (400 MHz, DMSO-$d_6$) δ 9.40 (s, 1H), 8.56 (d, J=5.0 Hz, 1H), 8.52 (d, J=2.5 Hz, 1H), 8.41 (d, J=2.4 Hz, 1H), 7.89 (d, J=1.7 Hz, 1H), 7.80-7.70 (m, 2H), 7.48 (d, J=5.0 Hz, 1H), 4.89 (t, J=5.1 Hz, 1H), 4.42-4.35 (m, 2H), 3.59 (s, 3H), 2.15 (s, 3H), 1.39 (s, 9H).

Example 128

(1R,2S)—N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide 128

Following the procedures of Example 123, 128 was prepared.

Example 129

N-[5-[3-(7,7-dimethyl-4-oxo-1,2,6,8-tetrahydrocyclopenta[3,4]pyrrolo[3,5-b]pyrazin-3-yl)-2-(hydroxymethyl)phenyl]-1-methyl-2-oxo-3-pyridyl]cyclopropanecarboxamide 129

Following the procedures of Example 120, 129 was prepared.

Example 130

N-[5-[3-(7,7-dimethyl-4-oxo-1,2,6,8-tetrahydrocyclopenta[3,4]pyrrolo[3,5-b]pyrazin-3-yl)-5-fluoro-2-(hydroxymethyl)phenyl]-1-methyl-2-oxo-3-pyridyl]cyclopropanecarboxamide 130

Following the procedures of Example 120, 130 was prepared.

Example 131

N-[5-[2-(7,7-dimethyl-4-oxo-1,2,6,8-tetrahydrocyclopenta[3,4]thieno[1,3-c]pyridin-3-yl)-3-(hydroxymethyl)-4-pyridyl]-1-methyl-2-oxo-3-pyridyl]cyclopropanecarboxamide 131

Following the procedures herein, 131 was prepared. LC-MS m/z: 519.3 [M+1]+. 1H NMR (400 MHz, CDCl3): δ 8.63 (s, 1H), 8.52 (d, J=2.0 Hz, 1H), 8.43 (d, J=5.2 Hz, 1H), 8.10 (d, J=2.0 Hz, 1H), 7.27 (d, J=5.2 Hz, 1H), 4.87 (d, J=13.2 Hz, 1H), 4.64 (d, J=12.0 Hz, 1H), 4.39-4.40 (m, 1H), 4.22 (t, J=11.6 Hz, 1H), 3.78-3.81 (m, 1H), 3.69 (s, 3H), 2.90-2.97 (m, 2H), 2.78 (s, 2H), 2.53-2.60 (m, 2H), 1.62-1.66 (m, 1H), 1.27 (s, 6H), 1.05-1.07 (m, 2H), 0.87-0.89 (m, 2H)

Example 132

(1S,2R)—N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide 132

Following the procedures of Example 123, 132 was prepared. LC-MS m/z: 536.21 [M+1]+. 1H NMR (400 MHz, DMSO-d6) δ 10.00 (s, 1H), 8.58-8.49 (m, 2H), 8.35 (d, J=2.4 Hz, 1H), 7.89 (d, J=1.7 Hz, 1H), 7.80-7.72 (m, 2H), 7.46 (d, J=5.0 Hz, 1H), 4.88 (t, J=5.2 Hz, 1H), 4.94-4.72 (m, 1H), 4.38 (t, J=4.9 Hz, 2H), 3.60 (s, 3H), 2.99-2.85 (m, 1H), 1.39 (s, 9H), 1.53-1.13 (m, 2H).

Example 133

N-[5-[3-(hydroxymethyl)-2-(1-oxo-3,4,6,7,8,9-hexahydropyrido[3,4-b]indolizin-2-yl)-4-pyridyl]-1-methyl-2-oxo-3-pyridyl]cyclopropanecarboxamide 133

Following the procedures herein, 133 was prepared. LC-MS m/z: 488.2 [M+1]+. 1H NMR (400 MHz, CDCl3): δ 8.65 (s, 1H), 8.54 (d, J=2.4 Hz, 1H), 8.43 (d, J=5.2 Hz, 1H), 8.14 (d, J=2.0 Hz, 1H), 7.25 (s, 1H), 6.31 (s, 1H), 5.10-5.07 (m, 1H), 4.65-4.62 (m, 1H), 4.46-4.39 (m, 1H), 4.24-4.21 (m, 1H), 3.93-3.82 (m, 2H), 3.70 (s, 3H), 2.94-2.85 (m, 2H), 2.83-2.81 (m, 2H), 2.05-2.02 (m, 2H), 1.88-1.86 (m, 2H), 1.69-1.65 (m, 2H), 1.09 (m, 2H), 0.91-0.89 (m, 2H).

Example 134

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-1-fluoro-cyclopropanecarboxamide 134

Following the procedures of Example 120, 134 was prepared. LC-MS m/z: 520.3 [M+1]+. 1H NMR (400 MHz, DMSO-d6) δ 9.24 (d, J=3.9 Hz, 1H), 8.48 (d, J=5.0 Hz, 1H), 8.42 (d, J=2.4 Hz, 1H), 7.82 (d, J=2.4 Hz, 1H), 7.32 (d, J=5.0 Hz, 1H), 6.55 (s, 1H), 4.94 (t, J=5.4 Hz, 1H), 4.40 (dd, J=8.8, 5.3 Hz, 2H), 4.30-4.15 (m, 3H), 3.85 (d, J=10.8 Hz, 1H), 3.63 (s, 3H), 2.57 (d, J=7.4 Hz, 2H), 2.43 (s, 2H), 1.53 (q, J=5.3, 4.8 Hz, 1H), 1.49 (q, J=5.3, 4.7 Hz, 1H), 1.34 (td, J=8.7, 5.3 Hz, 2H), 1.22 (s, 6H).

Example 135

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-1-hydroxy-cyclopropanecarboxamide 135

Following the procedures of Example 120, 135 was prepared. LC-MS m/z: 518.2 [M+1]+. 1H NMR (400 MHz, DMSO-d6) δ 9.76 (s, 1H), 8.49-8.45 (m, 2H), 7.75 (d, J=2.4 Hz, 1H), 7.31 (d, J=5.1 Hz, 1H), 6.86 (s, 1H), 6.55 (s, 1H), 4.94-4.89 (m, 1H), 4.45-4.36 (m, 2H), 4.22-4.15 (m, 2H), 3.89-3.82 (m, 1H), 3.61 (s, 3H), 2.57 (d, J=7.2 Hz, 1H), 2.43 (s, 2H), 1.24 (s, 1H), 1.22 (s, 6H), 1.16 (q, J=3.9, 3.5 Hz, 2H), 1.02 (d, J=3.4 Hz, 2H), 0.95 (d, J=6.5 Hz, 1H).

Example 136

N-[5-[3-(hydroxymethyl)-2-(4-oxo-6,7,8,9-tetrahydrobenzothiopheno[2,3-d]pyridazin-3-yl)-4-pyridyl]-1-methyl-2-oxo-3-pyridyl]cyclopropanecarboxamide 136

Following the procedures herein, 136 was prepared. LC-MS m/z: 504.0 [M+1]+. 1H NMR (400 MHz, CDCl3): δ 8.64 (s, 1H), 8.60 (d, J=5.6 Hz, 1H), 8.59 (d, J=3.2 Hz, 1H), 8.29 (s, 1H), 8.03 (d, J=2.4 Hz, 1H), 7.49 (d, J=5.2 Hz, 1H), 4.50 (m, 2H), 4.40 (br s, 1H), 3.70 (s, 3H), 2.97 (m, 2H), 2.85 (m, 2H), 1.97-1.96 (m, 4H), 1.68-1.64 (m, 1H), 1.08 (m, 2H), 0.90-0.88 (m, 2H).

Example 137

N-[5-[2-(7,7-dimethyl-4-oxo-1,2,6,8-tetrahydropyrido[3,4-b]pyrrolizin-3-yl)-3-(hydroxymethyl)-4-pyridyl]-1-methyl-2-oxo-3-pyridyl]cyclopropanecarboxamide 137

Step 1: A mixture of tert-butyl 5-oxopyrrolidine-2-carboxylate 137a (50 g, 270 mmol), TEA (54 g, 540 mmol), (Boc)$_2$O (70 g, 324 mmol) in DCM (1 L) was stirred at 20° C. for 16 h. The reaction solution was washed with brine (500 mL×3). See FIG. 1. The organic layer was dried over anhydrous sodium sulfate, filtered, and concentrated under reduced pressure. The residue was purified by column (PE/EA=6/1) to give 71 g (92%) of di-tert-butyl 5-oxopyrrolidine-1,2-dicarboxylate 137b as a white solid. $^1$H NMR (400 MHz, CDCl$_3$): δ 4.47-4.44 (m, 1H), 2.61-2.54 (m, 1H), 2.47-2.45 (m, 1H), 2.29-2.24 (m, 1H), 2.00-1.97 (m, 1H), 1.49 (s, 9H), 1.46 (s, 9H).

Step 2: To a solution of 137b (71 g, 250 mmol) in THF (1.5 L) at −78° C. was slowly added LiHMDS (500 mL, 500 mmol, 1M in THF), and the reaction mixture was stirred at −40° C. for 1 hour. See FIG. 1. Methyl iodide (71 g, 500 mmol) was added dropwise and the mixture was stirred at ambient temperature for 16 h. The reaction was poured into water (2 L) and extracted with EtOAc (1 L×3). The combined organic extracts were washed with brine (1 L×3), dried over anhydrous sodium sulfate, filtered, and concentrated under reduced pressure. The crude was purified by column (PE/EA=6/1) to give 35 g (44.9%) of di-tert-butyl 4,4-dimethyl-5-oxopyrrolidine-1,2-dicarboxylate 137c as a white solid. $^1$H NMR (400 MHz, CDCl$_3$): δ 4.27-4.23 (m, 1H), 2.06-2.00 (m, 1H), 1.75-1.71 (m, 1H), 1.36 (s, 9H), 1.33 (s, 9H), 1.05 (s, 6H).

Step 3: Et$_3$BHLi (134 mL, 134 mmol, 1M in THF) was added slowly to a mixture of 137c (35 g, 112 mmol) in THF (1 L) at −78° C. and stirred for 2 h. See FIG. 1. Saturated aqueous sodium bicarbonate solution (500 mL) was added, stirred for 30 min, then extracted with DCM (1 L×3). The combined organic extracts were washed with brine (1 L×3), dried over anhydrous sodium sulfate, filtered, and concentrated under reduced pressure to give di-tert-butyl 5-hydroxy-4,4-dimethylpyrrolidine-1,2-dicarboxylate 137d as a colorless oil (38 g, crude).

Step 4: Triethylsilane (14 g, 121 mmol) and BF$_3$-Et$_2$O (19 g, 133 mmol) were added to a mixture of 137d (38 g, 121 mmol) in DCM (1 L) at −78° C. and stirred for 30 min. See FIG. 1. Another batch of triethylsilane (14 g, 121 mmol) and BF$_3$-Et$_2$O (19 g, 133 mmol) was added and stirred for 2 h. The reaction was quenched with anhydrous sodium sulfate and extracted with DCM (1 L×2). The combined organic extracts were washed with brine (1 L×2), dried over anhydrous sodium sulfate, filtered, and concentrated under reduced pressure.

The residue was purified by column (PE/EA=5/1) to give di-tert-butyl 4,4-dimethylpyrrolidine-1,2-dicarboxylate 137e as a colorless oil (27 g, 75%). $^1$H NMR (400 MHz, CDCl$_3$): δ 4.20-4.10 (m, 1H), 3.35-3.32 (m, 1H), 3.20-3.13 (m, 1H), 2.04-1.99 (m, 1H), 1.70-1.64 (m, 1H), 1.44 (s, 9H), 1.42 (s, 9H), 1.09 (s, 3H), 1.08 (s, 3H).

Step 5: A mixture of 137e (27 g, 90 mmol) and TFA (100 mL) in DCM (200 mL) was stirred at 20° C. for 16 h. See FIG. 1. The reaction solution was concentrated under reduced pressure to give 4,4-dimethylpyrrolidine-2-carboxylic acid 137f as a brown oil (27 g, TFA salt). $^1$H NMR (400 MHz, CDCl$_3$): δ 12.08 (br s, 2H), 9.56 (br s, 1H), 7.77 (br s, 1H), 4.52 (s, 1H), 3.20 (s, 2H), 2.30-2.24 (m, 1H), 2.00-1.94 (m, 1H), 1.17 (s, 6H).

Step 6: A mixture of isobenzofuran-1,3-dione (20 g, 135 mmol) and 3-aminopropanoic acid (12 g, 135 mmol) was stirred at 170° C. for 6 h. See FIG. 2. Upon reaction completion, the mixture was diluted with water and extracted with DCM (100 mL×3). The combined organic layers were dried over anhydrous sodium sulfate, filtered, and concentrated under reduced pressure to give 3-(1,3-dioxoisoindolin-2-yl)propanoic acid 137g (20 g, 69%) as a white solid.

Step 7: To a solution of 137g (20.0 g, 91 mmol) in DCM (250 mL) were added oxalyl chloride (13.8 g, 109 mmol) and DMF (0.1 mL). See FIG. 2. The mixture was stirred at RT for 4 h. Upon reaction completion, the mixture was concentrated to give 3-(1,3-dioxoisoindolin-2-yl)propanoyl chloride 137h (20.0 g, 92%) as a white solid.

Step 8: To a solution of 4,4-dimethylpyrrolidine-2-carboxylic acid 137f (13.0 g, 72.5 mmol) in DMF (250 mL) was added 137h (17.0 g, 72.5 mmol) and TEA (14.5 g, 145 mmol). See FIG. 2. The mixture was stirred at RT (room temperature) for 16 h (sixteen hours). Upon reaction completion, the mixture was washed with brine (50 mL×3), dried over anhydrous sodium sulfate, filtered, and concentrated under reduced pressure to give crude 1-(3-(1,3-dioxoisoindolin-2-yl)propanoyl)-4,4-dimethylpyrrolidine-2-carboxylic acid 137i, which was used directly without purification.

Step 9: A mixture of 137i (crude, 72.5 mmol) and Ac$_2$O (100 mL) was stirred at 90° C. for 0.5 h. Then dimethyl but-2-ynedioate 137j (20.6 g, 145 mmol) was added. See FIG. 2. The mixture was stirred at 110° C. for 2 h. Upon reaction completion, the mixture was concentrated under reduced pressure. The crude was purified by silica gel chromatography (PE/EA=50/1 to 1/1) to give dimethyl 5-(2-(1,3-dioxoisoindolin-2-yl)ethyl)-2,2-dimethyl-2,3-dihydro-1H-pyrrolizine-6,7-dicarboxylate 137k (15 g, 48%).

Step 10: To a solution of 137k (15.0 g, 35.4 mmol) in EtOH (100 mL) was added hydrazine hydrate (3.5 g, 70.8 mmol). See FIG. 2. The mixture was stirred at 90° C. for 2 h. After cooling the reaction to RT, the resultant precipitate was filtered and washed with ethanol. The filtrate was concentrated to give crude methyl 7,7-dimethyl-1-oxo-2,3,4,6,7,8-hexahydro-1H-pyrido[3,4-b]pyrrolizine-9-carboxylate 137l as a yellow solid.

Step 11: To a solution of 137l (crude, 35.4 mmol) in THF/H₂O (100 mL/100 mL) was added LiOH (4.26 g, 177 mmol). See FIG. 2. The mixture was stirred at 50° C. for 1 h. Upon reaction completion, the mixture was acidified with HCl (1N) until pH<6 and concentrated to remove THF. The resulting white solid was collected by filtration and washed with cold water to give 7,7-dimethyl-1-oxo-2,3,4,6,7,8-hexahydro-1H-pyrido[3,4-b]pyrrolizine-9-carboxylic acid 137m (8 g, 91%).

Step 12: A microwave vial was charged with 137m (900 mg, 3.63 mmol), Cu₂O (26 mg, 0.18 mmol), phenanthroline (66 mg, 0.36 mmol), quinoline (3 g, 23 mmol) and NMP (8 mL). The reaction mixture was microwaved at 200° C. for 3 h. See FIG. 2. Water was added and the mixture was neutralized to pH 7 by addition of 1N HCl and extracted with EA (50 mL×3). The combined organic extracts were dried over anhydrous sodium sulfate, filtered, and concentrated under reduced pressure. The residue was purified by silica gel chromatography (DCM/MeOH=10/1) to give 7,7-dimethyl-2,3,4,6,7,8-hexahydro-1H-pyrido[3,4-b]pyrrolizin-1-one 137n (450 mg, 61%) as a white solid. $^1$H NMR (400 MHz, CDCl₃) δ 6.18 (t, J=1.2 Hz, 1H), 5.16 (s, 1H), 3.57 (s, 4H), 2.76 (t, J=6.9 Hz, 2H), 2.64 (d, J=1.1 Hz, 2H), 1.25 (s, 6H); MS-ESI [M+H]⁺=205.1.

Following the procedures herein, 137n was converted to 137. LC-MS m/z: 502.2 [M+1]+. 1H NMR (400 MHz, CDCl3): δ 8.65 (s, 1H), 8.54 (d, J=2.0 Hz, 1H), 8.43 (d, J=5.2 Hz, 1H), 8.14 (d, J=2.4 Hz, 1H), 7.25 (m, 1H), 6.25 (s, 1H), 5.10 (d, J=12.4 Hz, 1H), 4.66 (d, J=11.6 Hz, 1H), 4.40-4.39 (m, 1H), 4.25-4.21 (m, 1H), 3.83-3.80 (m, 1H), 3.71 (s, 3H), 3.68-3.61 (m, 2H), 3.04-3.03 (m, 1H), 2.91-2.87 (m, 1H), 2.68 (s, 2H), 1.67-1.65 (m, 1H), 1.30 (s, 6H), 1.09-0.99 (m, 2H), 0.91-0.80 (m, 2H).

Example 138

(1R,2R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methyl-cyclopropanecarboxamide 138

Following the procedures of Example 120, 138 was prepared. LC-MS m/z: 516.26 [M+1]+. 1H NMR (400 MHz, DMSO-d6) δ 9.58 (s, 1H), 8.46 (d, J=5.0 Hz, 1H), 8.40 (d, J=2.5 Hz, 1H), 7.72 (d, J=2.4 Hz, 1H), 7.28 (d, J=5.1 Hz, 1H), 6.55 (s, 1H), 4.95-4.90 (m, 1H), 4.46-4.33 (m, 2H), 4.28-4.14 (m, 3H), 3.89-3.80 (m, 1H), 3.59 (s, 3H), 2.57 (d, J=7.4 Hz, 1H), 2.42 (s, 2H), 2.02 (dt, J=8.3, 4.3 Hz, 1H), 1.22 (s, 6H), 1.21-1.14 (m, 1H), 1.07 (d, J=5.9 Hz, 3H), 1.01-0.95 (m, 1H), 0.65-0.58 (m, 1H).

Example 139

N-[5-[2-(hydroxymethyl)-3-(1-oxo-3,4,6,7,8,9-hexahydropyrido[3,4-b]indolizin-2-yl)phenyl]-1-methyl-2-oxo-3-pyridyl]cyclopropanecarboxamide 139

Following the procedures herein, 139 was prepared. LC-MS m/z: 487 [M+1]+.

Example 140

(R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.2]pentane-2-carboxamide 140

Following the procedures of Example 120, 140 was prepared, separated from the racemic mixture by chiral HPLC, eluting as the first peak. LC-MS m/z: 528.4 [M+1]+. 1H NMR (400 MHz, DMSO-d6) δ 9.41 (s, 1H), 8.47 (d, J=5.0 Hz, 1H), 8.43 (d, J=2.4 Hz, 1H), 7.72 (d, J=2.4 Hz, 1H), 7.29 (d, J=5.1 Hz, 1H), 6.56 (s, 1H), 4.97-4.89 (m, 1H), 4.47-4.33 (m, 2H), 4.29-4.14 (m, 3H), 3.89-3.80 (m, 1H), 3.58 (s, 3H), 2.63-2.51 (m, 3H), 2.42 (s, 2H), 1.38-1.29 (m, 2H), 1.22 (s, 6H), 0.93-0.80 (m, 3H), 0.80-0.71 (m, 1H).

Example 141

(S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.2]pentane-2-carboxamide 141

Following the procedures of Example 120, 141 was prepared, separated from the racemic mixture by chiral HPLC, eluting as the second peak. LC-MS m/z: 528.4 [M+1]+. 1H NMR (400 MHz, DMSO-d6) δ 9.41 (s, 1H), 8.47 (d, J=5.0 Hz, 1H), 8.43 (d, J=2.4 Hz, 1H), 7.72 (d, J=2.4 Hz, 1H), 7.29 (d, J=5.0 Hz, 1H), 6.56 (s, 1H), 4.97-4.89 (m, 1H), 4.48-4.33 (m, 2H), 4.29-4.14 (m, 3H), 3.89-3.80 (m, 1H), 3.58 (s, 3H), 2.60-2.52 (m, 3H), 2.42 (s, 2H), 1.37-1.29 (m, 2H), 1.22 (s, 6H), 0.94-0.81 (m, 2H), 0.80-0.71 (m, 1H).

Example 142

N-[5-[3-(7,7-dimethyl-4-oxo-1,2,6,8-tetrahydropyrido[3,4-b]pyrrolizin-3-yl)-2-(hydroxymethyl)phenyl]-1-methyl-2-oxo-3-pyridyl]cyclopropanecarboxamide 142

Following the procedures of Example 137, 142 was prepared.

Example 143

(S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.2]pentane-2-carboxamide 143

Following the procedures of Example 120, 143 was prepared, separated from the racemic mixture by chiral HPLC, eluting as the first peak. LC-MS m/z: 546.4 [M+1]+. 1H NMR (400 MHz, DMSO-d6) δ 9.81 (s, 1H), 8.46 (d, J=5.0 Hz, 1H), 8.40 (d, J=2.4 Hz, 1H), 7.73 (d, J=2.5 Hz, 1H), 7.28 (d, J=5.1 Hz, 1H), 6.55 (s, 1H), 4.92 (t, J=5.3 Hz, 1H), 4.46-4.32 (m, 2H), 4.28-4.14 (m, 3H), 3.88-3.81 (m, 1H), 3.59 (s, 3H), 3.57-3.50 (m, 2H), 3.47-3.41 (m, 2H), 2.57 (d, J=7.4 Hz, 2H), 2.42 (s, 2H), 1.22 (s, 6H), 1.11 (td, J=6.2, 5.4, 3.6 Hz, 5H).

Example 144

N-[5-[2-[6-(difluoromethoxy)-8-fluoro-1-oxo-3,4-dihydroisoquinolin-2-yl]-3-(hydroxymethyl)-4-pyridyl]-1-methyl-2-oxo-3-pyridyl]cyclopropanecarboxamide 144

Step 1: To a solution of 4-bromo-2-fluorobenzoic acid 144a (250 g, 1.14 mol) in dry DCM (2000 mL) was added oxalyl chloride (446 g, 3.51 mol) and DMF (10 mL) at RT, and the reaction mixture was stirred at RT for 1 h. See FIG. 3. The mixture was concentrated under reduced pressure to give 4-bromo-2-fluorobenzoyl chloride 144b (271 g, 100%) as a yellow solid, which was used for the next step without further purification.

Step 2: To a stirred suspension of aluminum trichloride (153 g, 1.15 mol) in DCE (1000 mL) was added a solution of 144b (271 g, 1.14 mol) in DCE (1000 mL) at 0° C. See FIG. 3. Ethylene gas was bubbled through the dark suspension for 3 h until the acid chloride was consumed. The reaction mixture was then stirred at RT overnight, cooled to 0° C., and quenched with 4M HCl (500 mL). The organic phase was separated and washed with brine (100 mL), dried over anhydrous sodium sulfate, and concentrated under reduced pressure. The crude residue was purified by column chromatography (PE/EA=30 to 10:1) to give 1-(4-bromo-2-fluorophenyl)-3-chloropropan-1-one 144c (210 g, 68%).

Step 3: A mixture of sodium chloride (333 g, 5.69 mol) and aluminum trichloride (1270 g, 9.52 mol) was added to 144c (210 g, 0.79 mol) in several portions at 130° C. See FIG. 3. The neat reaction mixture was then stirred at 180° C. After 5 h the reaction mixture was poured into a stirred solution of ice water (1000 mL) and concentrated HCl (100 mL). The quenched reaction was stirred for 40 min and then extracted with DCM (4000 mL×3). The combined organic phase was washed with saturated NaHCO$_3$ solution (1000 mL), brine (2000 mL×2), dried with anhydrous sodium sulfate, filtered and concentrated under reduced pressure. The residue was purified by silica gel chromatography (PE/EA=50/1, 10/1) to afford 55.0 g (30.4%) of 5-bromo-7-fluoro-2,3-dihydro-1H-inden-1-one 144d. $^1$H NMR (400 MHz, CDCl$_3$) δ 7.37 (s, 1H), 7.10-7.12 (d, J=8.4 Hz, 1H), 3.04-3.10 (m, 2H), 2.50-2.66 (m, 2H).

Step 4: To a mixture of 144d (10.35 g, 45.19 mmol) in DCM (75 mL) was added methanesulfonic acid (52.73 mL, 70.92 g, 737.90 mmol) at 0° C., followed by sodium azide (5.88 g, 90.44 mmol) in several portions. See FIG. 3. The reaction mixture was stirred at 0° C. for 2 h, and 20% aq. NaOH solution (40 mL) was added. The reaction mixture was stirred for 30 min, and the aqueous phase was extracted with DCM (400 mL×3). The combined organic layers were washed with saturated brine (200 mL×2), dried with anhydrous sodium sulfate, filtered and concentrated under reduced pressure. The residue was purified by silica gel chromatography (PE/EA=10/1 to 2/1) to afford the 5.2 g (47.1%) of 6-bromo-8-fluoro-3,4-dihydroisoquinolin-1(2H)-one 144e. $^1$H NMR (400 MHz, CDCl$_3$) δ 7.22-7.25 (d, J=10.4 Hz, 1H), 7.20 (s, 1H), 6.94 (s, 1H), 3.46-3.53 (m, 2H), 2.88-2.97 (m, 2H); MS-ESI [M+H]$^+$=243.9/245.9.

Step 5: To a mixture of 144e (24.0 g, 98.3 mmol) in CH$_3$CN (300 mL) was added (Boc)$_2$O (25.75 g, 118.0 mmol) and DMAP (24.0 g, 196.7 mmol) in one portion at RT. See FIG. 3. The mixture was stirred at room temperature for 10 h. The mixture was poured into ice-water (w/w=1/1) (150 mL) and stirred for 20 min. The aqueous phase was extracted with EtOAc (400 mL×3). The combined organic phase was washed with saturated critic acid (100 mL×2), sat. aq. NaHCO$_3$ solution (100 mL), brine (200 mL×2), dried with anhydrous sodium sulfate, filtered, and concentrated under reduced pressure to give crude tert-butyl 6-bromo-8-fluoro-1-oxo-3,4-dihydroisoquinoline-2(1H)-carboxylate 144f (36 g, 106%). $^1$H NMR (400 MHz, CDCl$_3$) δ 7.24-7.28 (m, 2H), 3.94-3.97 (m, 2H), 2.95-2.99 (m, 2H), 1.59 (s, 9H).

Step 6: To a mixture of 144f (20.0 g, 58.1 mmol), bis (pinacolato)diboron (18.6 g, 73.2 mmol), and KOAc (28.5 g, 290.6 mmol) in CH$_3$CN (200 mL) was added Pd(dppf)Cl$_2$ (10.4 g, 14 mmol) at room temperature under N$_2$. See FIG. 3. The reaction mixture was stirred at 80° C. overnight under N$_2$ and then filtered. The filtrate was concentrated under reduced pressure to give a residue, which was purified by column chromatography (PE/EA=40:1 to 10:1) to afford 20.0 g (88.0%) of tert-butyl 8-fluoro-1-oxo-6-(4,4,5,5-tetramethyl-1,3,2-dioxaborolan-2-yl)-3,4-dihydroisoquinoline-2(1H)-carboxylate 144g.

Step 7: To a solution of 144g (16.0 g, 40.9 mmol) in THF (200 mL) and H$_2$O (200 mL) was added sodium perborate (26.4 g, 171.8 mmol) in one portion at RT under N$_2$. See FIG. 3. The mixture was stirred at room temperature for 8 h. The mixture was filtered and the filtration was extracted with EtOAc (400 mL×5). The combined organic phase was washed with saturated brine (200 mL×2), dried with anhydrous sodium sulfate, filtered and concentrated under reduced pressure. The residue was purified by silica gel chromatography (PE/EA=30/1, 5/1) to afford 9.50 g (82.6%) of tert-butyl 8-fluoro-6-hydroxy-1-oxo-3,4-dihydroisoquinoline-2 (1H)-carboxylate 144h. $^1$H NMR (400 MHz, CDCl$_3$) δ 6.56-6.60 (d, J=13.6 Hz, 1H), 6.49 (s, 1H), 3.83-3.86 (m, 2H), 2.82-2.84 (m, 2H), 1.49 (s, 9H), 1.20 (s, 1H).

Step 8: To a mixture of 144h (3.0 g, 10.7 mmol) in DMF (30 mL) was added sodium 2-chloro-2,2-difluoroacetate (4.1 g, 26.7 mmol) and Cs$_2$CO$_3$ (4.5 g, 13.9 mmol) at RT under N$_2$. See FIG. 3. The reaction mixture was stirred at 120° C. for 4 h. The mixture was cooled to RT, poured into ice-water (w/w=1/1) (150 mL), and stirred for 20 min. The aqueous phase was extracted with EtOAc (400 mL×3). The combined organic phase was washed with saturated brine (200 mL×2), dried with anhydrous sodium sulfate, filtered, and concentrated in vacuo. The residue was purified by silica gel chromatography (PE/EA=30/1 to 20/1) to afford 2.0 g (56.6%) of tert-butyl 6-(difluoromethoxy)-8-fluoro-1-oxo-3,4-dihydroisoquinoline-2(1H)-carboxylate 144i.

Step 9: To a mixture of 144i (2.0 g, 6.0 mmol) in EtOAC (10 mL) was added HCl in EtOAC (20 mL, 4 M) at RT. See FIG. 3. The reaction mixture was stirred at room temperature for 1 h and then concentrated under reduced pressure. The crude residue was triturated with MTBE (20 mL) to give 2.0 g (85.9%) of 6-(difluoromethoxy)-8-fluoro-3,4-dihydroisoquinolin-1(2H)-one 144j. $^1$H NMR (400 MHz, CDCl$_3$) δ 6.80-6.85 (m, 2H), 6.40-6.76 (m, 1H), 6.19 (s, 1H), 3.51-3.55 (m, 2H), 2.98-3.01 (m, 2H); MS-ESI [M+H]$^+$=232.0.

Following the procedures herein, 144j was converted to 144. LC-MS m/z: 529.2 [M+1]+. 1H NMR (400 MHz, CDCl3): δ 8.65 (s, 1H), 8.55 (d, J=2.0 Hz, 1H), 8.48 (d, J=5.2 Hz, 1H), 8.09 (d, J=2.0 Hz, 1H), 7.35 (d, J=5.2 Hz, 1H), 6.88-6.87 (m, 2H), 6.62 (t, J=72.4 Hz, 1H), 4.72-4.64 (m, 2H), 4.32-4.26 (m, 2H), 3.72 (m, 4H), 3.20 (m, 2H), 1.67 (m, 1H), 1.08 (m, 2H), 0.92-0.90 (m, 2H).

Example 145

(1S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-ethoxy-cyclopropanecarboxamide 145

Following the procedures of Example 120, 145 was prepared, separated from the racemic mixture by chiral HPLC. LC-MS m/z: 546.4 [M+1]+. 1H NMR (400 MHz, DMSO-d6) δ 9.81 (s, 1H), 8.46 (d, J=5.0 Hz, 1H), 8.40 (d, J=2.4 Hz, 1H), 7.73 (d, J=2.4 Hz, 1H), 7.28 (d, J=5.2 Hz, 1H), 6.55 (s, 1H), 4.94-4.89 (m, 1H), 4.39 (dd, J=12.9, 5.2 Hz, 2H), 4.23 (d, J=7.9 Hz, 1H), 4.21-4.15 (m, 2H), 3.89-3.80 (m, 1H), 3.59 (s, 3H), 3.57-3.49 (m, 2H), 3.48-3.39 (m, 2H), 2.57 (d, J=7.4 Hz, 2H), 2.42 (s, 2H), 1.22 (s, 6H), 1.11 (td, J=6.3, 5.5, 3.6 Hz, 5H).

Example 146

(R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.3]hexane-2-carboxamide 146

Following the procedures of Example 120, 146 was prepared, separated from the racemic mixture by chiral HPLC, eluting as the first peak. LC-MS m/z: 542.4 [M+1]+. 1H NMR (400 MHz, DMSO-d6) δ 9.53 (s, 1H), 8.48-8.45 (m, 1H), 8.45-8.40 (m, 1H), 7.72 (d, J=2.4 Hz, 1H), 7.31-7.27 (m, 1H), 6.55 (s, 1H), 4.97-4.88 (m, 1H), 4.49-4.32 (m, 2H), 4.29-4.14 (m, 3H), 3.88-3.81 (m, 1H), 3.59 (s, 3H), 2.57 (d, J=7.7 Hz, 2H), 2.42 (s, 2H), 2.25-2.16 (m, 2H), 2.12-2.02 (m, 3H), 2.02-1.90 (m, 2H), 1.22 (s, 6H), 1.07-1.01 (m, 1H), 0.98-0.92 (m, 1H).

Example 147

(S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.3]hexane-2-carboxamide 147

Following the procedures of Example 120, 147 was prepared, separated from the racemic mixture by chiral HPLC, eluting as the first peak. LC-MS m/z: 542.4 [M+1]+. 1H NMR (400 MHz, DMSO-d6) δ 9.53 (s, 1H), 8.46 (d, J=5.0 Hz, 1H), 8.42 (d, J=2.3 Hz, 1H), 7.72 (d, J=2.4 Hz, 1H), 7.29 (d, J=5.1 Hz, 1H), 6.55 (s, 1H), 4.97-4.88 (m, 1H), 4.48-4.32 (m, 2H), 4.29-4.13 (m, 3H), 3.89-3.79 (m, 1H), 3.59 (s, 3H), 2.57 (d, J=7.6 Hz, 2H), 2.42 (s, 2H), 2.26-2.16 (m, 2H), 2.12-2.02 (m, 3H), 2.02-1.87 (m, 2H), 1.22 (s, 6H), 1.07-1.01 (m, 1H), 0.98-0.92 (m, 1H).

Example 148

(2R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]tetrahydrofuran-2-carboxamide 148

Following the procedures of Example 120, 148 was prepared, separated from the racemic mixture by chiral HPLC. LC-MS m/z: 532.4 [M+1]+. 1H NMR (400 MHz, DMSO-d6) δ 9.39 (s, 1H), 8.48 (d, J=5.1 Hz, 1H), 8.46 (d, J=2.4 Hz, 1H), 7.76 (d, J=2.4 Hz, 1H), 7.31 (d, J=5.0 Hz, 1H), 6.56 (s, 1H), 4.97-4.92 (m, 1H), 4.47 (dd, J=8.4, 5.6 Hz, 1H), 4.44-4.32 (m, 2H), 4.30-4.21 (m, 1H), 4.21-4.15 (m, 2H), 3.96 (dt, J=8.0, 6.6 Hz, 1H), 3.92-3.81 (m, 2H), 3.59 (s, 3H), 2.57 (d, J=7.6 Hz, 2H), 2.42 (s, 2H), 2.23 (dq, J=12.1, 7.7 Hz, 1H), 2.03-1.93 (m 1H), 1.86 (qt, J=12.3, 6.3 Hz, 2H), 1.22 (s, 6H).

Example 149

(2S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]tetrahydrofuran-2-carboxamide 149

Following the procedures of Example 120, 149 was prepared, separated from the racemic mixture by chiral HPLC. LC-MS m/z: 532.4 [M+1]+. 1H NMR (400 MHz, DMSO-d6) δ 9.39 (s, 1H), 8.48 (d, J=5.0 Hz, 1H), 8.46 (d, J=2.4 Hz, 1H), 7.77 (d, J=2.4 Hz, 1H), 7.31 (d, J=5.1 Hz, 1H), 6.56 (s, 1H), 4.94 (t, J=5.2 Hz, 1H), 4.47 (dd, J=8.4, 5.6 Hz, 1H), 4.44-4.33 (m 2H), 4.31-4.21 (m, 1H), 4.22-4.15 (m, 2H), 3.96 (dt, J=8.0, 6.6 Hz, 1H), 3.93-3.81 (m, 2H), 3.59 (s, 3H), 2.57 (d, J=7.6 Hz, 2H), 2.42 (s, 2H), 2.30-2.18 (m, 1H), 2.03-1.93 (m, 1H), 1.87 (dtt, J=19.2, 12.4, 6.3 Hz, 2H), 1.22 (s, 6H).

Example 150

(1S,2S)—N-[6-[2-(6-tert-butyl-8-fluoro-1-oxo-phthalazin-2-yl)-3-(hydroxymethyl)-4-pyridyl]-2-methyl-3-oxo-pyridazin-4-yl]-2-fluoro-cyclopropanecarboxamide 150

Following the procedures of Example 123, 150 was prepared. LC-MS m/z: 537.0 [M+1]+. 1H NMR (400 MHz, CDCl3): δ 8.88 (s, 1H), 8.69 (d, J=4.8 Hz, 1H), 8.59 (s, 1H), 8.28 (d, J=2.0 Hz, 1H), 7.56-7.49 (m, 3H), 4.93-4.73 (m, 1H), 4.55 (s, 2H), 3.90 (s, 3H), 3.63 (br s, 1H), 1.98-1.92 (m, 2H), 1.41 (s, 9H), 1.30-1.24 (m, 1H).

Example 151

(1S,2S)—N-[5-[2-[6-(difluoromethoxy)-8-fluoro-1-oxo-3,4-dihydroisoquinolin-2-yl]-3-(hydroxymethyl)-4-pyridyl]-1-methyl-2-oxo-3-pyridyl]-2-fluoro-cyclopropanecarboxamide 151

Following the procedures of Example 144, 151 was prepared. LC-MS m/z: 547.1 [M+1]+. 1H NMR (400 MHz, CDCl3): δ 8.69 (s, 1H), 8.59 (d, J=6.0 Hz, 1H), 8.49 (d, J=5.2 Hz, 1H), 8.12 (d, J=2.4 Hz, 1H), 7.36 (s, 1H), 6.88-6.87 (m, 2H), 6.62 (t, J=72.4 Hz, 1H), 4.94-4.76 (m, 1H), 4.73-4.65 (m, 2H), 4.39-4.26 (m, 2H), 3.78-3.66 (m, 4H), 3.27-3.15 (m, 2H), 1.94-1.89 (m, 2H), 1.25-1.17 (m, 1H).

Example 152

(1S,2S)—N-[5-[3-(6-tert-butyl-8-fluoro-1-oxo-phthalazin-2-yl)-5-fluoro-2-(hydroxymethyl)phenyl]-1-methyl-2-oxo-3-pyridyl]-2-fluoro-cyclopropanecarboxamide 152

Following the procedures of Example 123, 152 was prepared.

Example 153

(1S,2S)—N-[6-[2-(6-tert-butyl-8-fluoro-1-oxo-phthalazin-2-yl)-3-(hydroxymethyl)-4-pyridyl]-4-methyl-3-oxo-pyrazin-2-yl]-2-fluoro-cyclopropanecarboxamide 153

Following the procedures of Example 123, 153 was prepared. LC-MS m/z: 537.2 [M+1]+. 1H NMR (400 MHz, CDCl3): δ 9.14 (s, 1H), 8.61 (d, J=5.2 Hz, 1H), 8.32 (s, 1H), 7.83 (s, 1H), 7.62-7.50 (m, 3H), 4.89-4.42 (m, 4H), 3.71 (s, 3H), 2.27 (s, 1H), 2.01-1.96 (m, 1H), 1.43 (s, 9H), 1.25-1.24 (m, 1H).

Example 154

(1R,2R)—N-[5-[3-(6-tert-butyl-8-fluoro-1-oxo-phthalazin-2-yl)-5-fluoro-2-(hydroxymethyl)phenyl]-1-methyl-2-oxo-3-pyridyl]-2-fluoro-cyclopropanecarboxamide 154

Following the procedures of Example 123, 154 was prepared.

Example 155

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methyl-propanamide 155

Following the procedures of Example 120, 155 was prepared. LC-MS m/z: 504.26 [M+1]+. 1H NMR (400 MHz, DMSO-d6) δ 9.23 (s, 1H), 8.47 (d, J=5.0 Hz, 1H), 8.44 (d, J=2.4 Hz, 1H), 7.74 (d, J=2.4 Hz, 1H), 7.30 (d, J=5.0 Hz, 1H), 6.56 (s, 1H), 4.98-4.90 (m, 1H), 4.49-4.33 (m, 2H), 4.30-4.11 (m, 3H), 3.89-3.81 (m, 1H), 3.58 (s, 3H), 2.95-2.84 (m, 1H), 2.60-2.56 (m, 2H), 2.44-2.40 (m, 2H), 1.22 (s, 6H), 1.08 (d, J=6.8 Hz, 6H).

Example 156

N-[5-[2-(6-tert-butyl-8-fluoro-1-oxo-phthalazin-2-yl)-3-(hydroxymethyl)-4-pyridyl]-1-methyl-2-oxo-3-pyridyl]-2-methoxy-acetamide 156

Following the procedures of Example 123, 156 was prepared. LC-MS m/z: 522.21 [M+1]+. 1H NMR (400 MHz, DMSO-d6) δ 9.28 (s, 1H), 8.58 (d, J=5.0 Hz, 1H), 8.53 (d, J=2.6 Hz, 1H), 8.45 (d, J=2.4 Hz, 1H), 7.90 (d, J=1.7 Hz, 1H), 7.77 (dd, J=13.2, 2.0 Hz, 2H), 7.50 (d, J=5.0 Hz, 1H), 4.92 (t, J=5.1 Hz, 1H), 4.39 (t, J=4.5 Hz, 2H), 4.06 (s, 2H), 3.60 (s, 3H), 3.43 (s, 3H), 1.39 (s, 9H).

Example 157

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methoxy-acetamide 157

Following the procedures of Example 120, 157 was prepared. LC-MS m/z: 506.24 [M+1]+. 1H NMR (400 MHz, DMSO-d6) δ 9.26 (s, 1H), 8.52-8.42 (m, 2H), 7.77 (d, J=2.4 Hz, 1H), 7.31 (d, J=5.1 Hz, 1H), 6.56 (s, 1H), 4.97-4.92 (m, 1H), 4.40 (dd, J=7.5, 5.4 Hz, 2H), 4.30-4.14 (m, 3H), 4.06 (s, 2H), 3.90-3.80 (m, 1H), 3.60 (s, 3H), 3.43 (s, 3H), 2.57 (d, J=7.9 Hz, 2H), 2.42 (s, 2H), 1.22 (s, 6H).

Example 158

N-[5-[3-(hydroxymethyl)-2-[1-oxo-6-(trifluoromethoxy)-3,4-dihydroisoquinolin-2-yl]-4-pyridyl]-1-methyl-2-oxo-3-pyridyl]cyclopropanecarboxamide 158

Step 1: A mixture of 3-(trifluoromethoxy)benzaldehyde 158a (10.0 g, 52.6 mmol) and ethyl 2-(triphenylphosphoranylidene)acetate 158b (27.5 g, 78.9 mmol) in DCM (200 mL) was stirred at 15° C. for 2 h. See FIG. 4. The resulting mixture was concentrated under reduced pressure, and the crude was purified by column chromatography on silica gel (ethyl acetate:petroleum ether=1:8) to afford ethyl 3-(3-(trifluoromethoxy)phenyl)acrylate 158c (12.0 g, 88%) as yellow oil.

Step 2: To a solution of 158c (12.0 g, 46.1 mmol) in methanol (100 mL) was added 10% Pd/C (1.0 g), and the reaction mixture was stirred at 15° C. for 16 h under hydrogen atmosphere. See FIG. 4. The resulting mixture was filtered, and the filtrate was concentrated under reduced pressure to afford ethyl 3-(3-(trifluoromethoxy)phenyl)propanoate 158d (11.0 g, crude) as a colorless solid.

Step 3: To a mixture of 158d (11.0 g, 42 mmol) in ethanol/water (150 mL/100 mL) was added lithium hydroxide (8.8 g, 210 mmol). See FIG. 4. The resulting mixture was stirred at 15° C. for 2 h. The mixture was diluted with water and extracted with EtOAc (200 mL×3). The organic layers were dried over anhydrous sodium sulfate and concentrated to afford 3-(3-(trifluoromethoxy)phenyl)propanoic acid 158e as a colorless oil.

Step 4: 158e (9.0 g, 38.5 mmol) was added portionwise to chlorosulfonic acid (100 mL) while cooling with an iced bath. See FIG. 4. The resulting mixture was stirred at 0° C. for 1.5 h, poured into ice-water (1 L), and extracted with EtOAc (200 mL×3). The organic layers were dried over anhydrous sodium sulfate and concentrated. The residue was purified with by column chromatography on silica gel (ethyl acetate:petroleum ether=1:3) to afford 5-(trifluoromethoxy)-2,3-dihydro-1H-inden-1-one 158f (800 mg, 9.6%) as a yellow solid. $^1$H NMR (400 MHz, CDCl$_3$): δ 7.72 (d, J=8.4 Hz, 1H), 7.24 (s, 1H), 7.14 (d, J=8.4 Hz, 1H), 3.11 (t, J=5.6 Hz, 2H), 2.69-2.66 (m, 2H).

Step 5: To a solution of 158f (650 mg, 3 mmol) in dichloromethane (6 mL) and methanesulfonic acid (3 mL) was added sodium azide (0.293 mg, 4.5 mmol). See FIG. 4. The reaction mixture was stirred at 20° C. for 16 h. The reaction mixture was partitioned between DCM (50 mL) and aqueous sodium hydroxide solution (50 mL, 1.0 M). The aqueous layer was extracted with DCM (20 mL×3). The combined organic layers were washed sequentially with water and brine, dried over anhydrous sodium sulfate, and concentrated under reduced pressure. The residue was purified by column chromatography on silica gel (ethyl acetate:petroleum ether=1:2) to give 6-(trifluoromethoxy)-3,4-dihydroisoquinolin-1(2H)-one 158g (340 mg, 49%) as a white solid. $^1$H NMR (400 MHz, DMSO-d$_6$): δ 10.21 (br s, 1H), 7.20 (s, 1H), 7.13 (d, J=8.8 Hz, 1H), 6.89 (d, J=8.8 Hz, 1H), 2.89 (t, J=7.6 Hz, 2H), 2.48-2.31 (m, 2H)

Following the procedures herein, 158g was converted to 158. LC-MS m/z: 529.5 [M+1]+. 1H NMR (400 MHz, CDCl3): δ 8.66 (s, 1H), 8.55 (d, J=2.4 Hz, 1H), 8.49 (d, J=5.2 Hz, 1H), 8.22 (d, J=8.4 Hz, 1H), 8.09 (d, J=2.8 Hz, 1H), 7.35 (d, J=5.2 Hz, 1H), 7.24 (m, 1H), 7.16 (s, 1H), 4.78 (d, J=11.6 Hz, 1H), 4.64 (d, J=12.0 Hz, 1H), 4.44-4.38 (m, 1H), 4.31-4.29 (m, 1H), 3.81-3.78 (m, 1H), 3.72 (s, 3H), 3.70-3.28 (m, 1H), 3.19-3.15 (m, 1H), 1.70-1.64 (m, 1H), 1.09 (m, 2H), 0.92-0.90 (m, 2H).

Example 159

1-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-3-ethylurea 159

Following the procedures of Example 120, 159 was prepared. LC-MS m/z: 505.26 [M+1]+. 1H NMR (400 MHz, DMSO-d6) δ 8.46 (d, J=5.0 Hz, 1H), 8.33 (s, 1H), 8.23 (d, J=2.5 Hz, 1H), 7.56 (d, J=2.4 Hz, 1H), 7.28 (d, J=5.0 Hz, 1H), 7.15 (t, J=5.4 Hz, 1H), 6.55 (s, 1H), 4.94-4.88 (m, 1H), 4.49-4.33 (m, 2H), 4.19 (q, J=6.9, 5.3 Hz, 3H), 3.84 (d, J=9.2 Hz, 1H), 3.57 (s, 3H), 3.08 (qd, J=7.2, 5.3 Hz, 2H), 2.57 (d, J=7.4 Hz, 2H), 2.43 (s, 2H), 1.22 (s, 6H), 1.03 (t, J=7.2 Hz, 3H).

Example 160

N-[5-[2-(6-tert-butyl-1-methyl-benzimidazol-2-yl)-3-(hydroxymethyl)-4-pyridyl]-1-methyl-2-oxo-3-pyridyl]cyclopropanecarboxamide 160

Step 1: To a solution of 2-bromo-4-chloronicotinaldehyde 160a (20 g, 90.4 mmol), N,N-dimethylacetamide (15.6 g, 180.8 mmol) and methanol (8.8 g, 271 mmol) in 1,4-dioxane (150 mL) was added sodium borohydride (1.7 g, 45.2 mmol). See FIG. 5. The mixture was stirred at 20° C. for 10 min. TLC (petroleum ether:ethyl acetate=1:1) showed that the starting material was completely consumed. The mixture was quenched with saturated aqueous ammonium chloride solution (30 mL) and water (40 mL), and extracted with EtOAc (100 mL×2). The organic layers were washed with brine (100 mL), dried over anhydrous sodium sulfate, and concentrated under reduced pressure. The residue was purified by column chromatography on silica gel (eluting with petroleum ether:ethyl acetate from 50:1 to 1:1) to afford (2-bromo-4-chloropyridin-3-yl)methanol 160b (20 g, 95%) as a white solid.

Step 2: A mixture of 160b (20 g, 90.0 mmol), tert-butyldimethylchlorosilane (17.6 g, 117 mmol) and imidazole (12.2 g, 180 mmol) in N,N-dimethylformamide (300 mL) was stirred at 15° C. for 12 h. See FIG. 5. TLC (petroleum ether:ethyl acetate=3:1) showed that the starting material was completely consumed. The mixture was diluted with water (200 mL) and extracted with EtOAc (200 mL×2). The organic layers were washed with brine (60 mL), dried over anhydrous sodium sulfate, and concentrated under reduced pressure. The residue was purified by column chromatography on silica gel (eluting with petroleum ether:ethyl acetate=20:1) to afford 2-bromo-3-(((tert-butyldimethylsilyl)oxy)methyl)-4-chloropyridine 160c (30 g, 99%) as a colorless oil.

Step 3: A mixture of 160c (30 g, 89 mmol), 1,1'-bis(diphenylphosphino)ferrocene palladium dichloride (3.67 g, 4.5 mmol) and triethylamine (10.8 g, 107 mmol) in methanol (15 mL) was stirred at 80° C. under carbon monoxide CO (30 psi) for 2 h. See FIG. 5. The mixture was diluted with water (50 mL) and extracted with EtOAc (100 mL×2). The combined organic layers were washed with brine (100 mL), dried over anhydrous sodium sulfate, and concentrated under reduced pressure. The residue was purified by column chromatography on silica gel (eluting with petroleum ether:ethyl acetate=3:1) to afford methyl 3-(((tert-butyldimethylsilyl)oxy)methyl)-4-chloropicolinate 160d (25 g, 89%) as a yellow solid.

Step 4: A mixture of 160d (25 g, 76 mmol) and sodium hydroxide (6.1 g, 152 mmol) in ethanol (200 mL) and water (200 mL) was stirred at 19° C. for 2 h. See FIG. 5. The mixture was diluted with water (200 mL) and the resulting mixture was extracted with EtOAc (200 mL×2). The organic layers were washed with brine (80 mL), dried over anhydrous sodium sulfate, filtered, and concentrated under reduced pressure to afford 3-(((tert-butyldimethylsilyl)oxy)methyl)-4-chloropicolinic acid 160e (20 g, 87%) as a white solid.

Step 5: A mixture of 160e (20 g, 66 mmol), 4-(tert-butyl)benzene-1,2-diamine 160f (10.8 g, 66 mmol), O-(7-azabenzotriazol-1-yl)-N,N,N',N'-tetramethyluronium hexafluorophosphate (30 g, 79 mmol) and diisopropylethylamine (17 g, 132 mmol) in N,N-dimethylformamide (1000 mL) was stirred at 19° C. for 12 h. See FIG. 5. TLC (petroleum ether:ethyl acetate=1:1) showed that the starting material was completely consumed. The mixture was diluted with water (1000 mL) and extracted with EtOAc (1000 mL×2). The combined organic layers were washed with brine (500 mL), dried over anhydrous sodium sulfate, and concentrated under reduced pressure. The residue was purified by column chromatography on silica gel (eluting with petroleum ether:ethyl acetate=1:1) to afford N-(2-amino-4-(tert-butyl)phenyl)-3-(((tert-butyldimethylsilyl)oxy)methyl)-4-chloropicolinamide 160g (20 g, 67%) as a yellow solid.

Step 6: A solution of 160g (10 g, 22 mmol) in acetic acid (100 mL) was stirred at 120° C. for 5 h. See FIG. 5. The mixture was concentrated under reduced pressure, and the residue was purified by column chromatography on silica gel (eluting with petroleum ether:ethyl acetate=3:1) to afford (2-(6-(tert-butyl)-1H-benzo[d]imidazol-2-yl)-4-chloropyridin-3-yl)methyl acetate 160h (3.5 g, 44%) as a yellow solid. MS-ESI: [M+H]+ 358.2.

Step 7: A mixture of 160h (500 mg, 1.4 mmol) and 1,8-diazabicyclo[5.4.0]undec-7-ene (212 mg, 1.4 mmol) in dimethyl carbonate (100 mL) was stirred at 140° C. for 3 h. See FIG. 5. TLC (petroleum ether:ethyl acetate=3:1) showed that the starting material was completely consumed. The mixture was diluted with water (100 mL) and extracted with EtOAc (100 mL×2). The combined organic layers were washed with brine (60 mL), dried over anhydrous sodium sulfate, and concentrated under reduced pressure. The residue was purified by chromatography on silica gel (eluting with petroleum ether:ethyl acetate=3:1) to afford (2-(6-(tert-butyl)-1-methyl-1H-benzo[d]imidazol-2-yl)-4-chloropyridin-3-yl)methyl acetate 160i and (2-(5-(tert-butyl)-1-methyl-1H-benzo[d]imidazol-2-yl)-4-chloropyridin-3-yl)methyl acetate 160j as a mixture of regioisomers (480 mg, 92%). MS-ESI: [M+H]+ 372.1.

Step 8: A mixture of 160l and 160j (480 mg, 1.3 mmol), and sodium hydroxide (104 mg, 2.6 mmol) in ethanol (20 mL) and water (20 mL) was stirred at 19° C. for 2 h. See FIG. 5. The mixture was diluted with water (20 mL) and extracted with EtOAc (20 mL×2). The organic layers were washed with brine (50 mL), dried over anhydrous sodium sulfate, and concentrated under reduced pressure to afford (2-(6-(tert-butyl)-1-methyl-1H-benzo[d]imidazol-2-yl)-4-chloropyridin-3-yl)methanol 160k and (2-(5-(tert-butyl)-1-methyl-1H-benzo[d]imidazol-2-yl)-4-chloropyridin-3-yl)methanol 160l as a mixture of regioisomers (400 mg, 94%). MS-ESI: [M+H]+ 330.2.

Following the procedures herein, 160k was converted to 160. LC-MS m/z: 486.2 [M+1]+. 1H NMR (400 MHz, CDCl3): 8.68 (s, 1H), 8.63-8.62 (m, 2H), 7.85 (d, J=2.0 Hz, 1H), 7.72 (d, J=9.2 Hz, 1H), 7.44-7.43 (m, 2H), 7.38 (d, J=4.8 Hz, 1H), 6.96 (t, J=7.6 Hz, 1H), 4.46 (d, J=7.2 Hz, 2H), 4.13 (s, 3H), 3.74 (s, 3H), 1.68-1.62 (m, 1H), 1.44 (s, 9H), 1.09-1.07 (m, 2H), 0.92-0.89 (m, 2H).

Example 161

(R)—N-[5-[2-(6-tert-butyl-8-fluoro-1-oxo-phthalazin-2-yl)-3-(hydroxymethyl)-4-pyridyl]-1-methyl-2-oxo-3-pyridyl]spiro[2.2]pentane-2-carboxamide 161

Following the procedures of Example 123, 161 was prepared, separated from the racemic mixture by chiral HPLC as the first peak. LC-MS m/z: 544.1 [M+1]+. 1H NMR (400

MHz, CDCl3): δ 8.62-8.61 (m, 2H), 8.55 (s, 1H), 8.34 (d, J=2.4 Hz, 1H), 8.03 (d, J=2.4 Hz, 1H), 7.57-7.50 (m, 3H), 4.48-4.39 (m, 2H), 4.24-4.20 (m, 1H), 3.70 (s, 3H), 2.07-2.04 (m, 1H), 1.56-1.54 (m, 1H), 1.48-1.43 (m, 10H), 0.99-0.96 (m, 4H).

Example 162

(S)—N-[5-[2-(6-tert-butyl-8-fluoro-1-oxo-phthalazin-2-yl)-3-(hydroxymethyl)-4-pyridyl]-1-methyl-2-oxo-3-pyridyl]spiro[2.2]pentane-2-carboxamide 162

Following the procedures of Example 123, 162 was prepared, separated from the racemic mixture by chiral HPLC as the second peak. LC-MS m/z: 544.2 [M+1]+. 1H NMR (400 MHz, CDCl3): δ 8.62-8.61 (m, 2H), 8.55 (s, 1H), 8.34 (d, J=2.4 Hz, 1H), 8.03 (d, J=2.4 Hz, 1H), 7.57-7.50 (m, 3H), 4.48-4.39 (m, 2H), 4.24-4.20 (m, 1H), 3.70 (s, 3H), 2.07-2.04 (m, 1H), 1.56-1.54 (m, 1H), 1.48-1.43 (m, 10H), 0.99-0.96 (m, 4H).

Example 163

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]butanamide 163

Following the procedures of Example 120, 163 was prepared. LC-MS m/z: 504.3 [M+1]+. 1H NMR (400 MHz, CDCl3): δ 8.58 (d, J=2.4 Hz, 1H), 8.46-8.43 (m, 2H), 8.15 (d, J=2.0 Hz, 1H), 7.31 (d, J=5.2 Hz, 1H), 6.84 (s, 1H), 5.18-5.15 (m, 1H), 4.70-4.45 (m, 2H), 4.30-4.10 (m, 3H), 3.95-3.80 (m, 1H), 3.70 (s, 3H), 2.58 (s, 2H), 2.52 (s, 2H), 2.42 (t, J=7.2 Hz, 2H), 1.77 (m, 2H), 1.28 (s, 6H), 1.06 (t, J=7.2 Hz, 3H).

Example 164

N-[5-[2-(5-tert-butyl-1-methyl-benzimidazol-2-yl)-3-(hydroxymethyl)-4-pyridyl]-1-methyl-2-oxo-3-pyridyl]cyclopropanecarboxamide 164

Following the procedures of Example 160, 164 was prepared. LC-MS m/z: 486.2 [M+1]+. 1H NMR (400 MHz, DMSO-d6): 9.75 (s, 1H), 8.71 (d, J=5.2 Hz, 1H), 8.48 (d, J=2.0 Hz, 1H), 7.75 (s, 1H), 7.69 (s, 1H), 7.62 (d, J=8.4 Hz, 1H), 7.49-7.47 (m, 2H), 4.43 (s, 2H), 3.94 (s, 3H), 3.61 (s, 3H), 2.32-2.26 (m, 1H), 1.37 (s, 9H), 0.78-0.76 (m, 4H).

Example 165

(R)—N-[5-[2-(6-tert-butyl-8-fluoro-1-oxo-phthalazin-2-yl)-3-(hydroxymethyl)-4-pyridyl]-1-methyl-2-oxo-3-pyridyl]-6-methyl-6-azaspiro[2.5]octane-2-carboxamide 165

Step 1: A mixture of tert-butyl 4-oxopiperidine-1-carboxylate 165a (10.0 g, 50.2 mmol) and ethyl 2-(triphenylphosphoranylidene)acetate (26.2 g, 75.3 mmol) in toluene (200 mL) was stirred at 100° C. for 1 h. See FIG. 6. The mixture was concentrated and purified by column chromatography on silica gel (petroleum ether:ethyl acetate=10:1) to afford tert-butyl 4-(2-ethoxy-2-oxoethylidene)piperidine-1-carboxylate 165b (12.6 g, 93%) as a white solid. ¹H NMR (400 MHz, CDCl₃): δ 5.72 (s, 1H), 4.16 (q, J=7.2 Hz, 2H), 3.52-3.45 (m, 4H), 2.94 (t, J=5.6 Hz, 2H), 2.28 (t, J=5.6 Hz, 2H), 1.48 (s, 9H), 1.29 (t, J=7.6 Hz, 3H).

Step 2: Sodium hydride (60% in mineral oil) (2.06 g, 85.8 mmol) was added to dimethylsulfoxide (100 mL) at 15° C., and the mixture was stirred at 15° C. for 20 min. See FIG. 6. Trimethylsulfoxonium iodide (19.0 g, 85.8 mmol) was added, and the reaction mixture was stirred for 2 h, then 165b (7.72 g, 28.7 mmol) was added and the resulting mixture was stirred at 15° C. for 50 h. Water (100 mL) was added, and the mixture was extracted with EtOAc (200 mL×3). The combined organic extracts were washed with brine (100 mL×2), dried over anhydrous sodium sulfate, filtered, and concentrated under reduced pressure. The residue was purified by silica gel column (petroleum ether: EtOAc=2:1) to yield 6-tert-butyl 1-ethyl 6-azaspiro[2.5]octane-1,6-dicarboxylate 165c (4.4 g, 54%) as a colorless oil. ¹H NMR (400 MHz, CD₃CN): δ 4.06-4.04 (m, 2H), 3.40-3.18 (m, 4H), 1.92-1.90 (m, 1H), 1.59-1.50 (m, 3H), 1.39-1.30 (m, 10H), 1.19-1.16 (m, 3H), 1.03-1.01 (m, 1H), 0.91-0.93 (m, 1H).

Step 3: To the solution of 165c (500 mg, 1.76 mmol) in ethanol (8 mL) was added sodium hydroxide (212 mg, 5.3 mmol) in water (4 mL). See FIG. 6. The mixture was stirred at 15° C. for 12 h. The solvent was evaporated under reduced pressure. The aqueous solution was acidified with dilute hydrochloride acid (0.5 M) slowly under ice bath until pH~4, and extracted with EtOAc (10 mL×3). The combined organic extracts were dried over anhydrous sodium sulfate, filtered, and concentrated to give 6-(tert-butoxycarbonyl)-6-azaspiro[2.5]octane-1-carboxylic acid 165d (390 mg, 83%) as a white solid. ¹H NMR (400 MHz, CDCl₃): δ 3.52-3.42 (m, 3H), 3.38-3.35 (m, 1H), 1.75-1.72 (m, 2H), 1.58-1.56 (m, 1H), 1.46-1.43 (m, 11H), 1.23-1.21 (m, 1H), 1.02-1.01 (m, 1H).

Step 4: To a mixture of 165d (400 mg, 1.57 mmol) and N,N-dimethylformamide (0.1 mL) in DCM (5 mL) was added oxalyl chloride (397 mg, 3.13 mmol) dropwise. See FIG. 6. The reaction mixture was stirred at 15° C. for 2.5 h and then concentrated. The residue was dissolved in tetrahydrofuran (20 mL) and added dropwise to aqueous ammonia (10 mL, 28%). The mixture was stirred at 15° C. for 4 h and then diluted with water (15 mL). The reaction mixture was extracted with EtOAc (15 mL×3). The combined organic layers were dried over anhydrous sodium sulfate, filtered, and concentrated to afford tert-butyl 1-carbamoyl-6-azaspiro[2.5]octane-6-carboxylate 165e (260 mg, 65%) as a white solid. ¹H NMR (400 MHz, CDCl₃): δ 5.58 (s, 1H), 5.34 (s, 1H), 3.48-3.39 (m, 4H), 1.73-1.70 (m, 2H), 1.48 (s, 9H), 1.47-1.41 (m, 2H), 1.40-1.22 (m, 2H), 0.89-0.87 (m, 1H).

Step 5: A mixture of 165e (100 mg, 0.39 mmol), 2-(5-bromo-3'-(hydroxymethyl)-1-methyl-6-oxo-1,6-dihydro-[3,4'-bipyridin]-2'-yl)-6-(tert-butyl)-8-fluorophthalazin-1(2H)-one 165f (202 mg, 0.39 mmol), tris(dibenzylideneacetone)dipalladium (0) (18 mg, 0.02 mmol), 4,5-bis(diphenylphosphino)-9,9-dimethylxanthene (23 mg, 0.04 mmol) and cesium carbonate (384 mg, 1.18 mmol) was stirred at 100° C. under N₂ for 1 h. See FIG. 6. After cooling to ambient temperature, the mixture was poured into water (10 mL) and extracted with EtOAc (10 mL×3). The combined organic layers were dried over anhydrous sodium sulfate, filtered, concentrated under reduced pressure, and purified by prep-TLC (petroleum ether:ethyl acetate:methylene chloride:methanol=5:5:10:1) to afford tert-butyl 1-((2'46-(tert-butyl)-8-fluoro-1-oxophthalazin-2(1H)-yl)-3'-(hydroxymethyl)-1-methyl-6-oxo-1,6-dihydro-[3,4'-bipyridin]-5-yl)carbamoyl)-6-azaspiro[2.5]octane-6-carboxylate 165g (150 mg, 58%) as a white solid.

Step 6: A solution of 165g (120 mg, 0.18 mmol) in methanolic hydrochloride solution (5 mL) was stirred at 15° C. for 20 min, and then concentrated. The residue was dissolved in DCM (20 mL) and washed with aqueous sodium bicarbonate (10 mL×3). See FIG. 6. The organic layer was dried over anhydrous sodium sulfate, filtered, concentrated under reduced pressure to afford N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-6-azaspiro[2.5]octane-1-carboxamide 165h (100 mg, 98%) as a yellow solid. MS-ESI: [M+H]$^+$ 587.2.

Step 7: Aqueous formaldehyde (3 mL, 37%) was added dropwise to the solution of 165h (80 mg, 0.17 mmol) in methanol (5 mL). See FIG. 6. After 30 min at 15° C., sodium cyanoborohydride (26 mg, 0.40 mmol) was added. The mixture was stirred at 15° C. for another 1 h, then concentrated under reduced pressure. The reaction was quenched with water (20 mL), then extracted with EtOAc (20 mL×3). The combined organic extracts were dried over anhydrous sodium sulfate, filtered, concentrated under reduced pressure, and purified by prep-TLC (dichloromethane:methanol=10:1) to afford racemic N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-6-azaspiro[2.5]octane-1-carboxamide (40 mg, 50%). MS-ESI: [M+H]$^+$ 601.3. The enantiomers were separated by SFC to give 165 and 166.

First eluting peak 165 SFC RT=0.561 min. $^1$H NMR (400 MHz, CDCl$_3$): δ 8.65-8.62 (m, 3H), 8.35 (d, J=2.4 Hz, 1H), 8.03 (d, J=2.0 Hz, 1H), 7.58-7.51 (m, 3H), 4.49-4.24 (m, 3H), 3.72 (s, 3H), 2.51-2.30 (m, 7H), 1.82 (br s, 2H), 1.58-1.57 (m, 2H), 1.44 (s, 9H), 1.28-1.26 (m, 2H), 0.95-0.94 (m, 1H); MS-ESI: [M+H]$^+$ 601.3.

Example 166

(S)—N-[5-[2-(6-tert-butyl-8-fluoro-1-oxo-phthalazin-2-yl)-3-(hydroxymethyl)-4-pyridyl]-1-methyl-2-oxo-3-pyridyl]-6-methyl-6-azaspiro[2.5]octane-2-carboxamide 166

Following the procedures of Example 165, separation by SFC gave the second eluting peak 166 at RT=0.899 min. $^1$H NMR (400 MHz, CDCl$_3$): δ 8.71 (s, 1H), 8.64 (d, J=5.2 Hz, 1H), 8.57 (s, 1H), 8.35 (d, J=2.0 Hz, 1H), 8.03 (s, 1H), 7.58-7.55 (m, 2H), 7.49 (d, J=4.8 Hz, 1H), 4.48-4.22 (m, 3H), 3.73 (s, 3H), 3.50 (br s, 3H), 2.77 (br s, 6H), 1.67 (m, 2H), 1.44 (s, 9H), 1.26 (s, 3H); MS-ESI: [M+H]$^+$ 601.3.

Example 167

(1S,2S)-2-fluoro-N-[5-[5-fluoro-2-(hydroxymethyl)-3-(1-oxo-3,4,6,7,8,9-hexahydropyrido[3,4-b]indolizin-2-yl)phenyl]-1-methyl-2-oxo-3-pyridyl]cyclopropanecarboxamide 167

Following the procedures herein, 167 was prepared. LC-MS m/z: 524 [M+1]+.

Example 168

(1S,2S)—N-[5-[3-(7,7-dimethyl-4-oxo-1,2,6,8-tetrahydropyrido[3,4-b]pyrrolizin-3-yl)-5-fluoro-2-(hydroxymethyl)phenyl]-1-methyl-2-oxo-3-pyridyl]-2-fluoro-cyclopropanecarboxamide 168

Following the procedures of Example 137, 168 was prepared. LC-MS m/z: 538 [M+1]+.

Example 169

(1R,3S)—N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide 169

Following the procedures of Example 123, 169 was prepared, separated from the racemic mixture by chiral HPLC as the first peak. LC-MS m/z: 587.2 [M+1]+. 1H NMR (400 MHz, CDCl3): δ 8.69 (s, 1H), 8.63 (d, J=5.2 Hz, 1H), 8.60 (s, 1H), 8.35 (d, J=1.6 Hz, 1H), 8.02 (d, J=1.6 Hz, 1H), 7.58-7.51 (m, 3H), 4.48-4.40 (m, 2H), 3.72 (s, 3H), 2.90-2.83 (m, 2H), 2.75-2.67 (m, 2H), 2.42 (s, 3H), 2.02-1.95 (m, 3H), 1.84-1.82 (m, 1H), 1.49-1.48 (m, 1H), 1.44 (s, 9H), 1.19-1.18 (m, 1H).

Example 170

N2-[5-[2-(6-tert-butyl-8-fluoro-1-oxo-phthalazin-2-yl)-3-(hydroxymethyl)-4-pyridyl]-1-methyl-2-oxo-3-pyridyl]-N1,N1-dimethyl-cyclopropane-1,2-dicarboxamide 170

Following the procedures of Example 123, 170 was prepared, separated from the racemic mixture by chiral HPLC as a mixture of enantiomers in the second peak. LC-MS m/z: 589.3 [M+1]+. 1H NMR (400 MHz, CDCl3): δ 8.81 (s, 1H), 8.63-8.61 (m, 2H), 8.35 (d, J=2.0 Hz, 1H), 8.05 (s, 1H), 7.58-7.50 (m, 3H), 4.60-4.30 (m, 2H), 4.30-4.15 (m, 1H), 3.70 (s, 3H), 3.14 (s, 3H), 2.96 (s, 3H), 2.19-2.15 (m, 2H), 1.88-1.86 (m, 1H), 1.43 (s, 9H), 1.34-1.32 (m, 1H).

Example 171

N2-[5-[2-(6-tert-butyl-8-fluoro-1-oxo-phthalazin-2-yl)-3-(hydroxymethyl)-4-pyridyl]-1-methyl-2-oxo-3-pyridyl]-N1,N1-dimethyl-cyclopropane-1,2-dicarboxamide 171

Following the procedures of Example 123, 171 was prepared, separated from the racemic mixture by chiral HPLC as a mixture of enantiomers in the first peak. LC-MS m/z: 589.2 [M+1]+. 1H NMR (400 MHz, CDCl3): δ 8.81 (s, 1H), 8.64-8.61 (m, 2H), 8.35 (d, J=2.0 Hz, 1H), 8.07 (s, 1H), 7.58-7.51 (m, 3H), 4.60-4.35 (m, 2H), 4.35-4.15 (m, 1H), 3.70 (s, 3H), 3.15 (s, 3H), 2.97 (s, 3H), 2.19-2.15 (m, 2H), 1.89-1.84 (m, 1H), 1.44 (s, 9H), 1.35-1.33 (m, 1H).

Example 172

(1S,2S)—N-[5-[3-(7,7-dimethyl-4-oxo-1,2,6,8-tetrahydrocyclopenta[3,4]pyrrole[3,5-b]pyrazin-3-yl)-5-fluoro-2-(hydroxymethyl)phenyl]-1-methyl-2-oxo-3-pyridyl]-2-fluoro-cyclopropanecarboxamide 172

Following the procedures of Example 120, 172 was prepared. LC-MS m/z: 538 [M+1]+.

Example 173

(1S,3S)—N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide 173

Following the procedures of Example 123, 173 was prepared, separated from the racemic mixture by chiral HPLC as a mix of diastereomers in the first and second peaks. LC-MS m/z: 587.1 [M+1]+. 1H NMR (400 MHz, CDCl3): δ 8.76 (s, 1H), 8.73-8.61 (m, 2H), 8.34 (d, J=2.0 Hz, 1H), 8.02 (s, 1H), 7.57-7.50 (m, 3H), 4.48-4.40 (m, 2H), 3.71 (s, 3H), 2.76-2.50 (m, 5H), 2.38 (s, 3H), 2.00-1.92 (m, 2H), 1.86-1.79 (m, 1H), 1.48-1.41 (m, 1H), 1.43 (s, 9H), 1.17-1.15 (m, 1H).

Example 174

(1S,3R)—N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide 174

Following the procedures of Example 123, 174 was prepared, separated from the racemic mixture by chiral HPLC as a single stereoisomer in the third peak. LC-MS m/z: 587.3 [M+1]+. 1H NMR (400 MHz, CDCl3): δ 8.92 (s, 1H), 8.63-8.60 (m, 2H), 8.35 (s, 1H), 8.04 (s, 1H), 7.58-7.50 (m, 3H), 4.49-4.39 (m, 2H), 3.71 (s, 3H), 3.09-3.05 (m, 1H), 3.00-2.98 (m, 2H), 2.86-2.84 (m, 2H), 2.63 (s, 3H), 2.23-2.14 (m, 2H), 2.00-1.95 (m, 1H), 1.50-1.38 (m, 1H), 1.44 (s, 9H), 0.94-0.88 (m, 1H).

Example 175

(1S,3R)—N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide 175

Following the procedures of Example 123, 175 was prepared, separated from the racemic mixture by chiral HPLC as a mixture of diastereomers in the fourth peak. LC-MS m/z: 587.2 [M+1]+. 1H NMR (400 MHz, CDCl3): δ 8.66 (s, 1H), 8.62 (d, J=5.2 Hz, 1H), 8.60 (s, 1H), 8.35 (d, J=1.6 Hz, 1H), 8.04 (s, 1H), 7.58-7.51 (m, 3H), 4.49-4.40 (m, 2H), 3.72 (s, 3H), 2.84-2.78 (m, 2H), 2.66-2.62 (m, 2H), 2.39 (s, 3H), 1.99-1.93 (m, 3H), 1.82-1.79 (m, 1H), 1.49-1.48 (m, 1H), 1.44 (s, 9H), 1.18-1.16 (m, 1H).

Example 176

(1R,2R)—N-[5-[3-(7,7-dimethyl-4-oxo-1,2,6,8-tetrahydrocyclopenta[3,4]pyrrole[3,5-b]pyrazin-3-yl)-5-fluoro-2-(hydroxymethyl)phenyl]-1-methyl-2-oxo-3-pyridyl]-2-fluoro-cyclopropanecarboxamide 176

Following the procedures of Example 120, 176 was prepared. LC-MS m/z: 538 [M+1]+.

Example 901

Biochemical Btk Assay

A generalized procedure for a standard biochemical Btk, Kinase Assay that can be used to test Formula I compounds is as follows. A master mix minus Btk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 μM Promega PTK Biotinylated peptide substrate 2, and 0.01% BSA. A master mix plus Btk enzyme is prepared containing 1× Cell Signaling kinase buffer, 0.5 μM (micromolar) PTK Biotinylated peptide substrate 2, 0.01% BSA, and 100 ng/well (0.06 mU/well) Btk enzyme. Btk enzyme is prepared as follows: full length human wildtype Btk (accession number NM-000061) with a C-terminal V5 and 6×His tag was subcloned into pFastBac® vector (Invitrogen/Life Technologies) for making baculovirus carrying this epitope-tagged Btk. Generation of baculovirus is done based on Invitrogen's instructions detailed in its published protocol "Bac-to-Bac Baculovirus Expression Systems" (Invitrogen/Life Technologies, Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining. A solution of 200 μM ATP is prepared in water and adjusted to pH 7.4 with 1N NaOH. A quantity of 1.25 μL (microliter) of compounds in 5% DMSO is transferred to a 96-well ½ area Costar polystyrene plate. Compounds are tested singly and with an 11-point dose-responsive curve (starting concentration is 10 μM; 1:2 dilution). A quantity of 18.75 μL of master mix minus enzyme (as a negative control) and master mix plus enzyme is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1× detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated. Alternatively, the Lanthascreen assay can be used to evaluate Btk activity through quantification of its phosphorylated peptide product. The FRET (Fluorescence Resonance Energy Transfer) that occurs between the fluorescein on the peptide product and the terbium on the detection antibody decreases with the addition of inhibitors of Btk that reduce the phosphorylation of the peptide. In a final reaction volume of 25 uL, Btk (h) (0.1 ng/25 ul reaction) is incubated with 50 mM Hepes pH 7.5, 10 mM MgCl2, 2 mM $MnCl_2$, 2 mM DTT, 0.2 mM NaVO4, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at room temperature. Detection is determined on a Perkin Elmer Envision with 340 nM excitation and emission at 495 nm and 520 nm. Exemplary Btk inhibition IC50 values are in Tables 1 and 2.

Example 902

Ramos Cell Btk Assay

Another generalized procedure for a standard cellular Btk, Kinase Assay that can be used to test Formula I compounds is as follows. Ramos cells are incubated at a density of $0.5 \times 10^7$ cells/ml in the presence of test compound for 1 hr at 37° C. Cells are then stimulated by incubating with 10 μg/ml anti-human IgM F(ab)$_2$ for 5 minutes at 37° C. Cells are pelleted, lysed, and a protein assay is performed on the cleared lysate. Equal protein amounts of each sample are subject to SDS-PAGE and western blotting with either anti-phosphoBtk (Tyr223) antibody (Cell Signaling Technology #3531; Epitomics, cat. #2207-1) or phosphoBtk(Tyr551) antibody (BD Transduction Labs #558034) to assess Btk autophosphorylation or an anti-Btk antibody (BD Transduction Labs #611116) to control for total amounts of Btk in each lysate.

Example 903

B-Cell Proliferation Assay

A generalized procedure for a standard cellular B-cell proliferation assay that can be used to test Formula I compounds is as follows. B-cells are purified from spleens of 8-16 week old Balb/c mice using a B-cell isolation kit (Miltenyi Biotech, Cat #130-090-862). Testing compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences # RPNQ 0130). SPA-bead based fluorescence is counted in a microbeta counter (Wallace Triplex 1450, Perkin Elmer).

Example 904

T Cell Proliferation Assay

A generalized procedure for a standard T cell proliferation assay that can be used to test Formula I compounds is as follows. T cells are purified from spleens of 8-16 week old Balb/c mice using a Pan T cell isolation kit (Miltenyi Biotech, Cat #130-090-861). Testing compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD #553057) and anti-CD28 (BD #553294) antibodies. Following 24 hr incubation, 1 µCi $^3$H-thymidine is added and plates incubated an additional 36 hr prior to harvest using the manufacturer's protocol for SPA[$^3$H] thymidine uptake assay system (Amersham Biosciences # RPNQ 0130). SPA-bead based fluorescence was counted in a microbeta counter (Wallace Triplex 1450, Perkin Elmer).

Example 905

CD86 Inhibition Assay

A generalized procedure for a standard assay for the inhibition of B cell activity that can be used to test Formula I compounds is as follows. Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 24 hr at 37° C., 5% $CO_2$. Following the 24 hr incubation, cells are transferred to conical bottom clear 96-well plates and pelleted by centrifugation at 1200×g×5 min. Cells are preblocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur® flow cytometer (BD Biosciences, San Jose, Calif.) and gated on the CD19$^+$/7AAD$^-$ population. The levels of CD86 surface expression on the gated population is measured versus test compound concentration.

Example 906

B-ALL Cell Survival Assay

The following is a procedure for a standard B-ALL (acute lymphoblastic leukemia) cell survival study using an XTT readout to measure the number of viable cells. This assay can be used to test Formula I compounds for their ability to inhibit the survival of B-ALL cells in culture. One human B-cell acute lymphoblastic leukemia line that can be used is SUP-B15, a human Pre-B-cell ALL line that is available from the ATCC.

SUP-B15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% $CO_2$ for up to 3 days. After 3 days cells are split 1:3 into fresh 96-well plates containing the test compound and allowed to grow up to an additional 3 days. After each 24 h period, 50 ul of an XTT solution is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

Example 907

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer® (Becton, Dickinson and Co.) tubes with sodium heparin.

Solutions of Formula I compounds at 10 mM in DMSO are diluted 1:10 in 100% DMSO, then are diluted by three-fold serial dilutions in 100% DMSO for a ten point dose-response curve. The compounds are further diluted 1:10 in PBS and then an aliquot of 5.5 µl of each compound is added in duplicate to a 2 ml 96-well plate; 5.5 µl of 10% DMSO in PBS is added as control and no-stimulus wells. Human whole blood—HWB (100 µl) is added to each well. After mixing the plates are incubated at 37° C., 5% $CO_2$, 100% humidity for 30 minutes. Goat F(ab')2 anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with fluorescent labeled antibodies for 30 minutes, at 37° C., 5% $CO_2$, 100% humidity. Include induced control, unstained and single stains for compensation adjustments and initial voltage settings. Samples are then lysed with PharM Lyse™ (BD Biosciences Pharmingen) according to the manufacturer's instructions. Samples are then transferred to a 96 well plate suitable to be run on the BD Biosciences HTS 96 well system on the LSRII machine. Data acquired and Mean Fluorescence Intensity values were obtained using BD Biosciences DIVA Software. Results are initially analyzed by FACS analysis software (Flow Jo). The inhibitory concentrations (IC50, IC70, IC90, etc.) for test compounds is defined as the concentration which decreases by, for example 50%, the percent positive of CD69 cells that are also CD20 positive stimulated by anti-IgM (average of 8 control wells, after subtraction of the average of 8 wells for the no-stimulus background). The IC70 values are calculated by Prism version 5, using a nonlinear regression curve fit and are shown in Tables 1 and 2.

Example 908

In Vitro Cell Proliferation Assay

Efficacy of Formula I compounds are measured by a cell proliferation assay employing the following protocol (Mendoza et al (2002) Cancer Res. 62:5485-5488). The CellTiter-Glo® Luminescent Cell Viability Assay, including reagents and protocol are commercially available (Promega Corp., Madison, Wis., Technical Bulletin TB288). The assay assesses the ability of compounds to enter cells and inhibit cell proliferation. The assay principle is based on the determination of the number of viable cells present by quantitating the ATP present in a homogenous assay where addition of the Cell-Titer Glo reagent results in cell lysis and generation of a luminescent signal through the luciferase reaction. The luminescent signal is proportional to the amount of ATP present.

A panel of B-cell lymphoma cell lines (BJAB, SUDHL-4, TMD8, OCI-Ly10, OCI-Ly3, WSU-DLCL2) are plated into 384-well plate in normal growth medium, and serially diluted BTK inhibitors or DMSO alone were added to each well. Cell viability is assessed after 96 hour incubation by CellTiter-Glo® (Promega). Data may be presented as Relative cell viability in BTK inhibitor-treated cells relative to DMSO-treated control cells. Data points are the mean of 4 replicates at each dose level. Error bars represent SD from the mean. Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate 0/N at 37° C., 5% CO2.

Day 2—Add Drug to Cells, Compound Dilution, DMSO Plates (serial 1:2 for 9 points), Add 20 µl compounds at 10 mM in the 2nd column of 96 well plate. Perform serial 1:2 across the plate (10 µl+20 µl 100% DMSO) for a total of 9 points using Precision. Media Plates 96-well conical bottom polypropylene plates from Nunc (cat. #249946) (1:50 dilution) Add 147 µl of Media into all wells. Transfer 3 µl of DMSO+compound from each well in the DMSO Plate to each corresponding well on Media Plate using Rapidplate.

Drug Addition to Cells, Cell Plate (1:10 dilution), Add 6 µl of media+compound directly to cells (54 µl of media on the cells already). Incubate 3 days at 37 C, 5% CO2 in an incubator that will not be opened often.

Day 5—Develop Plates, Thaw Cell Titer Glo Buffer at room temperature. Remove Cell Plates from 37° C. and equilibrate to room temperature. for about 30 minutes. Add Cell Titer Glo Buffer to Cell Titer Glo Substrate (bottle to bottle). Add 30 µl Cell Titer Glo Reagent (Promega cat. # G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions are made in DMSO in a 96 well plate. The compounds are further diluted into growth media using a Rapidplate® robot (Zymark Corp., Hopkinton, Mass.). The diluted compounds are then added to quadruplicate wells in 384-well cell plates and incubated at 37° C. and 5% CO2. After 4 days, relative numbers of viable cells are measured by luminescence using Cell-Titer Glo (Promega) according to the manufacturer's instructions and read on a Wallac Multilabel Reader® (PerkinElmer, Foster City). EC50 values are calculated using Prism® 4.0 software (GraphPad, San Diego). Formula I compounds and chemotherapeutic agents are added simultaneously or separated by 4 hours (one before the other) in all assays.

An additional exemplary in vitro cell proliferation assay includes the following steps:

1. An aliquot of 100 µl of cell culture containing about $10^4$ cells in medium is deposited in each well of a 384-well, opaque-walled plate.

2. Control wells are prepared containing medium and without cells.

3. The compound is added to the experimental wells and incubated for 3-5 days.

4. The plates are equilibrated to room temperature for approximately 30 minutes.

5. A volume of CellTiter-Glo Reagent equal to the volume of cell culture medium present in each well is added.

6. The contents are mixed for 2 minutes on an orbital shaker to induce cell lysis.

7. The plate is incubated at room temperature for 10 minutes to stabilize the luminescence signal.

8. Luminescence is recorded and reported in graphs as RLU=relative luminescence units.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

We claim:

1. A compound selected from Formula I:

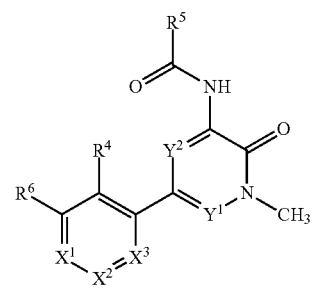

or stereoisomers, tautomers, or pharmaceutically acceptable salts thereof, wherein:

$X^1$ is N;
$X^2$ is $CR^2$;
$X^3$ is $CR^3$;
$R^1$, $R^2$ and $R^3$ are independently selected from H, F, Cl, CN, —NH$_2$, —NHCH$_3$, —N(CH$_3$)$_2$, —OH, —OCH$_3$, —OCH$_2$CH$_3$, —OCH$_2$CH$_2$OH, and C$_1$-C$_3$ alkyl;
$R^4$ is selected from H, F, Cl, CN, —CH$_2$OH, —CH(CH$_3$)OH, —C(CH$_3$)$_2$OH, —CH(CF$_3$)OH, —CH$_2$F, —CHF$_2$, —CH$_2$CHF$_2$, —CF$_3$, —C(O)NH$_2$, —C(O)NHCH$_3$, —C(O)N(CH$_3$)$_2$, —NH$_2$, —NHCH$_3$, —N(CH$_3$)$_2$, —NHC(O)CH$_3$, —OH, —OCH$_3$, —OCH$_2$CH$_3$, —OCH$_2$CH$_2$OH, cyclopropyl, cyclopropylmethyl, 1-hydroxycyclopropyl, imidazolyl, pyrazolyl, 3-hydroxy-oxetan-3-yl, oxetan-3-yl, and azetidin-1-yl;
$R^5$ is $C_3$-$C_{12}$ carbocyclyl, —($C_1$-$C_6$ alkyl)-($C_3$-$C_{12}$ carbocyclyl), $C_2$-$C_{20}$ heterocyclyl, —($C_1$-$C_6$ alkyl)-($C_2$-$C_{20}$ heterocyclyl), $C_1$-$C_6$ alkyl, —NH—($C_1$-$C_6$ alkyl), —($C_1$-$C_6$ alkyl)-($C_1$-$C_{20}$ heteroaryl), $C_1$-$C_{20}$ heteroaryl, $C_6$-$C_{20}$ aryl;
$R^6$ is selected from the structures:
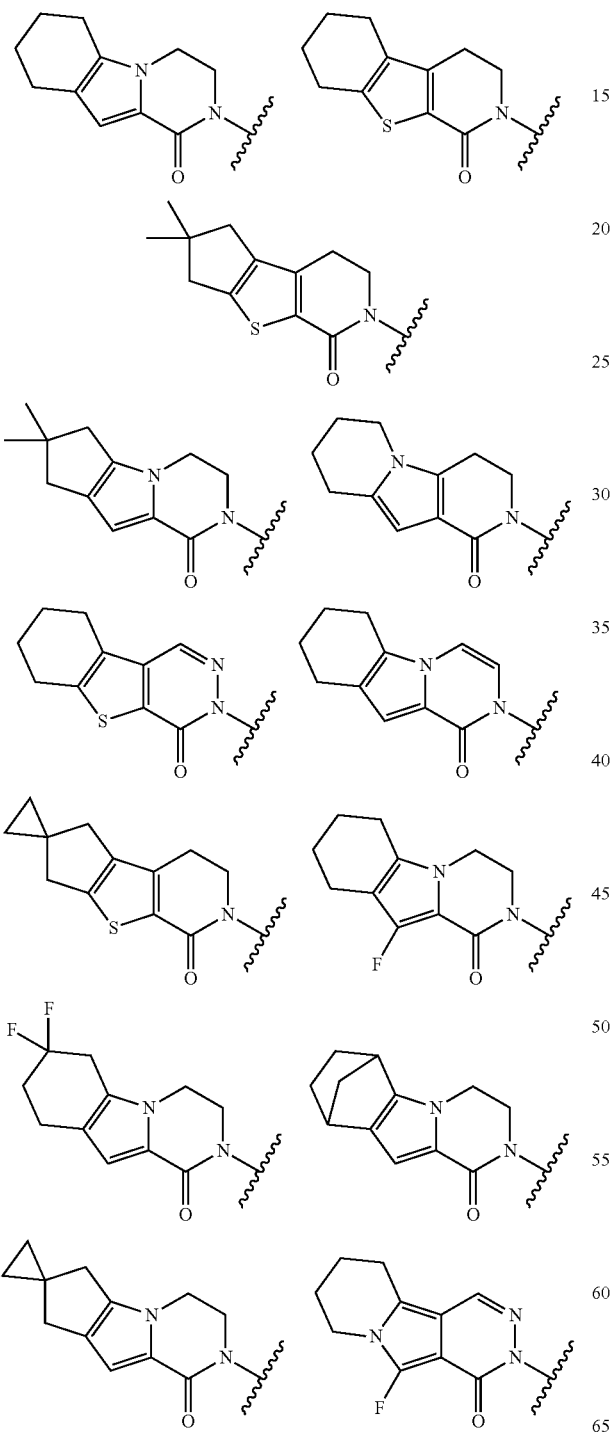
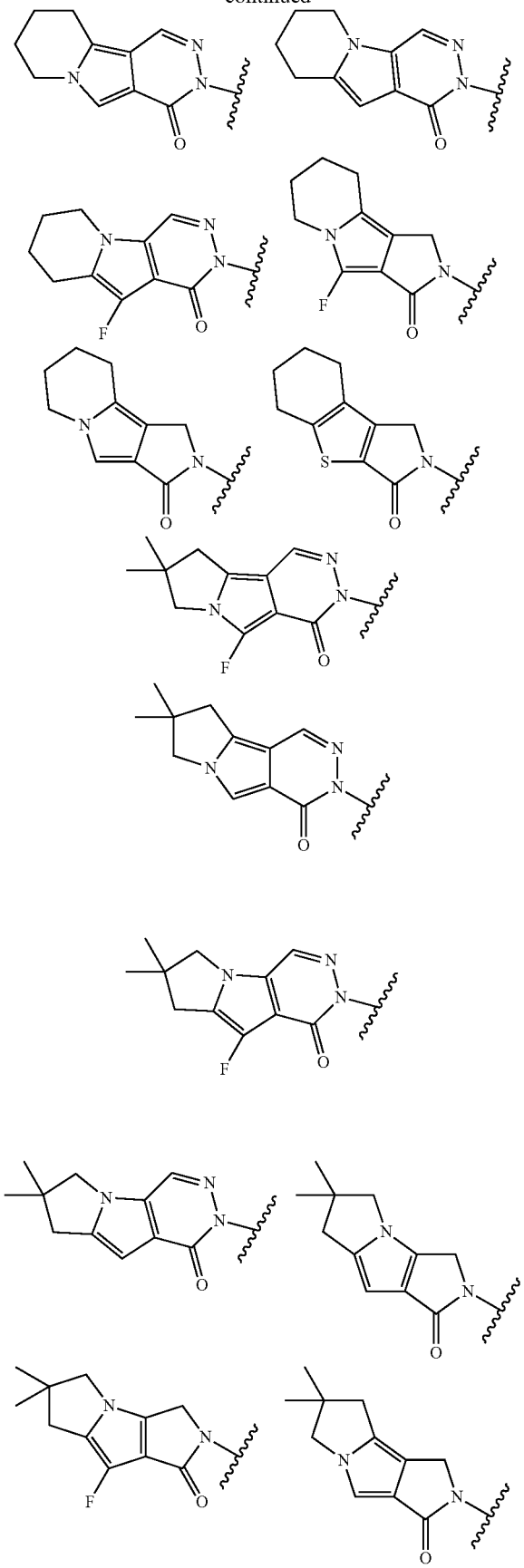

-continued

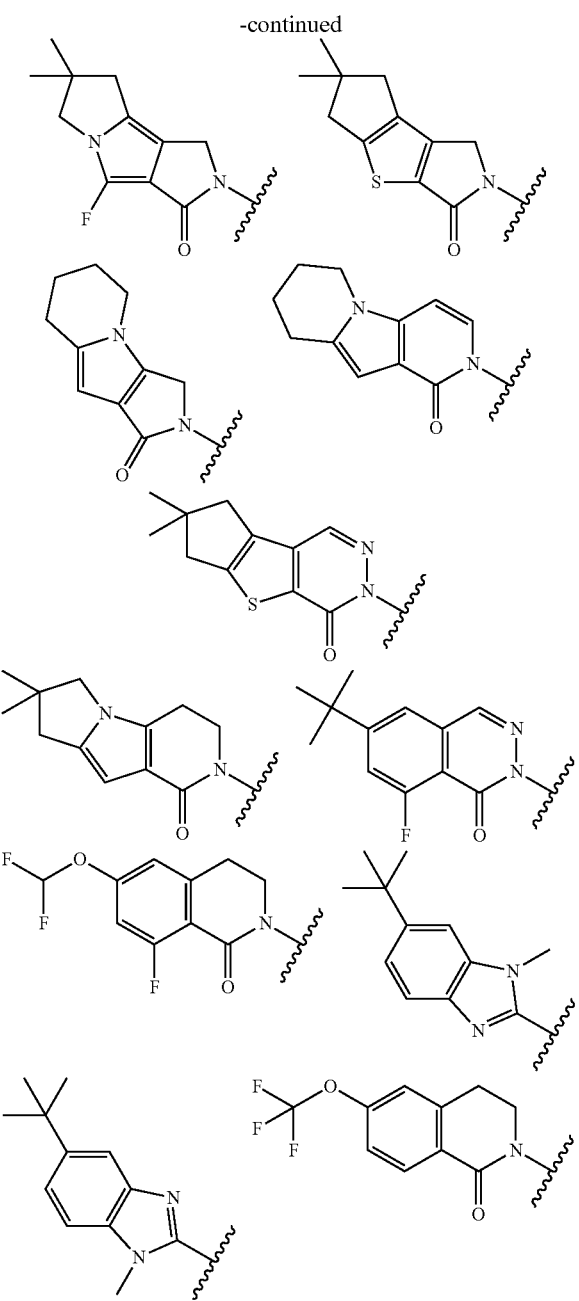

where the wavy line indicates the site of attachment; and Y¹ and Y² are independently selected from CH and N;

where alkyl, carbocyclyl, heterocyclyl, aryl, and heteroaryl are optionally substituted with one or more groups independently selected from F, Cl, Br, I, —CN, —CH₃, —CH₂CH₃, —CH(CH₃)₂, —CH₂CH(CH₃)₂, —CH₂OH, —CH₂OCH₃, —CH₂CH₂OH, —C(CH₃)₂OH, —CH(OH)CH(CH₃)₂, —C(CH₃)₂CH₂OH, —CH₂CH₂SO₂CH₃, —CH₂OP(O)(OH)₂, —CH₂F, —CHF₂, —CF₃, —CH₂CF₃, —CH₂CHF₂, —CH(CH₃) CN, —C(CH₃)₂CN, —CH₂CN, —CO₂H, —COCH₃, —CO₂CH₃, —CO₂C(CH₃)₃, —COCH(OH)CH₃, —CONH₂, —CONHCH₃, —CON(CH₃)₂, —C(CH₃)₂ CONH₂, —NH₂, —NHCH₃, —N(CH₃)₂, —NH-COCH₃, —N(CH₃)COCH₃, —NHS(O)₂CH₃, N(CH₃) C(CH₃)₂CONH₂, —N(CH₃)CH₂CH₂S(O)₂CH₃, —NO₂, =O, —OH, —OCH₃, —OCH₂CH₃, —OCH₂CH₂OCH₃, —OCH₂CH₂OH, —OCH₂CH₂N (CH₃)₂, —OCF₃, —OCHF₂, —OP(O)(OH)₂, —S(O)₂ N(CH₃)₂, —SCH₃, —S(O)₂CH₃, —S(O)₃H, cyclopropyl, oxetanyl, azetidinyl, 1-methylazetidin-3-yl)oxy, N-methyl-N-oxetan-3-yl amino, azetidin-1-ylmethyl, pyrrolidin-1-yl, and morpholino.

2. The compound of claim 1 wherein R⁴ is —CH₂OH.
3. The compound of claim 1 wherein R⁵ is C₃-C₁₂ carbocyclyl.
4. The compound of claim 3 wherein R⁵ is cyclopropyl, optionally substituted with one or more F and —CH₃.
5. The compound of any one of claims 1-2 wherein R⁵ is —(C₁-C₆ alkyl)-(C₃-C₁₂ carbocyclyl).
6. The compound of claim 1 wherein R⁵ is C₂-C₂₀ heterocyclyl.
7. The compound of claim 1 wherein R⁵ is —(C₁-C₆ alkyl)-(C₂-C₂₀ heterocyclyl).
8. The compound of claim 1 wherein R⁵ is C₁-C₆ alkyl.
9. The compound of claim 1 wherein R⁵ is —(C₁-C₆ alkyl)-(C₁-C₂₀ heteroaryl).
10. The compound of claim 1 wherein R⁵ is C₁-C₂₀ heteroaryl.
11. The compound of claim 1 wherein R⁵ is C₆-C₂₀ aryl.
12. The compound of claim 1 wherein R⁶ is

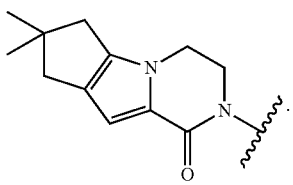

13. The compound of claim 1 wherein R⁶ is

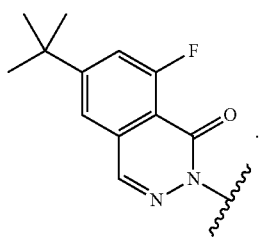

14. The compound of claim 1 wherein Y¹ is CH and Y² is N.
15. The compound of claim 1 wherein Y¹ is N and Y² is CH.
16. The compound of claim 1 wherein Y¹ and Y² are each CH.
17. The compound of claim 1 wherein Y¹ and Y² are each CH, and R⁶ is CH₃.
18. The compound of claim 1 selected from the group consisting of:
   N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]cyclobutanecarboxamide;
   N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]cyclopropanecarboxamide;
   2-cyclopropyl-N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]acetamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]oxetane-3-carboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-2-morpholino-acetamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-2-methyl-cyclopropanecarboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]propanamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-2-(3,5-dimethylpyrazol-1-yl)acetamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]pyridine-3-carboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-*pyri dyl*]-1-methyl-pyrazole-4-carboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-5-methyl-1H-pyrazole-3-carboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-1,5-dimethyl-pyrazole-3-carboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-6-pyrrolidin-1-yl-pyridine-3-carboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-*pyri dyl*]benzamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]oxazole-5-carboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-2,2-difluoro-cyclopropanecarboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-2-fluoro-cyclopropanecarboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-2-fluoro-cyclopropanecarboxamide;

(1R,2R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide;

(1S,2S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-fluoro-cyclopropanecarboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]acetamide;

(1R,2R)—N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide;

(1S,2S)—N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide;

N-[5-[2-(6-tert-butyl-8-fluoro-1-oxo-phthalazin-2-yl)-3-(hydroxymethyl)-4-pyridyl]-1-methyl-2-oxo-3-pyridyl]-2-fluoro-cyclopropanecarboxamide;

N-[5-[2-(6-tert-butyl-8-fluoro-1-oxo-phthalazin-2-yl)-3-(hydroxymethyl)-4-pyridyl]-1-methyl-2-oxo-3-pyridyl]cyclopropanecarboxamide;

N-[5-[2-(6-tert-butyl-8-fluoro-1-oxo-phthalazin-2-yl)-3-(hydroxymethyl)-4-pyridyl]-1-methyl-2-oxo-3-pyridyl]propanamide; and N-[5-[2-(6-tert-butyl-8-fluoro-1-oxo-phthalazin-2-yl)-3-(hydroxymethyl)-4-pyridyl]-1-methyl-2-oxo-3-pyridyl]acetamide.

19. The compound of claim 1 selected from:

(1R,2S)—N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide;

N-[5-[2-(7,7-dimethyl-4-oxo-1,2,6,8-tetrahydrocyclopenta[3,4]thieno[1,3-c]pyridin-3-yl)-3-(hydroxyethyl)-4-pyridyl]-1-methyl-2-oxo-3-pyridyl]cyclopropanecarboxamide;

(1S,2R)—N-(5-(2-(6-tert-butyl-8-fluoro-1-oxophthalazin-2(1H)-yl)-3-(hydroxymethyl)pyridin-4-yl)-1-methyl-2-oxo-1,2-dihydropyridin-3-yl)-2-fluorocyclopropanecarboxamide;

N-[5-[3-(hydroxymethyl)-2-(1-oxo-3,4,6,7,8,9-hexahydropyrido[3,4-b]indolizin-2-yl)-4-pyridyl]-1-methyl-2-oxo-3-pyridyl]cyclopropanecarboxamide;

N-[5-[2-(7,7-dimethyl-4-oxo-1,2,6,8-tetrahydrocyclopenta[3,4-b]pyrrolo[3,5-b]pyrazin-3-yl)-3-(hydroxyethyl)-4-pyridyl]-1-methyl-2-oxo-3-pyridyl]-1-fluoro-cyclopropanecarboxamide;

N-[5-[2-(7,7-dimethyl-4-oxo-1,2,6,8-tetrahydrocyclopenta[3,4]pyrrolo[3,5-b]pyrazin-3-yl)-3-(hydroxyethyl)-4-pyridyl]-1-methyl-2-oxo-3-pyridyl]-1-hydroxy-cyclopropanecarboxamide;

N-[5-[3-(hydroxymethyl)-2-(4-oxo-6,7,8,9-tetrahydrobenzothiopheno[2,3-d]pyridazin-3-yl)-4-pyridyl]-1-methyl-2-oxo-3-pyridyl]cyclopropanecarboxamide;

N-[5-[2-(7,7-dimethyl-4-oxo-1,2,6,8-tetrahydropyrido[3,4-b]pyrrolizin-3-yl)-3-(hydroxymethyl)-4-pyridyl]-1-methyl-2-oxo-3-pyridyl]cyclopropanecarboxamide;

(1R,2R)—N-[5-[2-(7,7-dimethyl-4-oxo-1,2,6,8-tetrahydrocyclopenta[3,4]pyrrolo[3,5-b]pyrazin-3-yl)-hydroxymethyl)-4-pyridyl]-1-methyl-2-oxo-3-pyridyl]-2-methyl-cyclopropanecarboxamide;

(R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.2]pentane-2-carboxamide;

(S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.2]pentane-2-carboxamide;

(1R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-ethoxy-cyclopropanecarboxamide;

N-[5-[2-[6-(difluoromethoxy)-8-fluoro-1-oxo-3,4-dihydroisoquinolin-2-yl]-3-(hydroxymethyl)-4-pyridyl]1-methyl-2-oxo-3-pyridyl]cyclopropanecarboxamide;

(1S)—N-[5-[2-(7,7-dimethyl-4-oxo-1, 2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-ethoxy-cyclopropanecarboxamide;

(R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2.3]hexane-2-carboxamide;

(S)—N-[5-[2-(7,7-dimethyl-1-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]spiro[2,3]hexane-2-carboxamide;

(2R)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]tetrahydrofuran-2-carboxamide;

(2S)—N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]tetrahydrofuran-2-carboxamide;

(1S,2S)—N-[6-[2-(6-tert-butyl-8-fluoro-1-oxo-phthalazin-2-yl)-3-(hydroxymethyl)-4-pyridyl]-2-methyl-3-oxo-pyridazin-4-yl]-2-fluoro-cyclopropanecarboxamide;

(1S,2S)—N-[5-[2-(6-(difluoromethoxy)-8-fluoro-1-oxo-3,4-dihydroisoquinolin-2-yl]-3-(hydroxymethyl)-4-pyridyl-1-methyl-2-oxo-3-pyridyl]-2-fluoro-cyclopropanecarboxamide;

(1S,2S)—N-[6-[2-(6-tert-butyl-8-fluoro-1-oxo-phthalazin-2-yl)-3-(hydroxymethyl)-4-pyridyl]-4-methyl-3-oxo-pyrazin-2-yl]-2-fluoro-cyclopropanecarboxamide;

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methylpropanamide;

N-[5-[2-(6-tert-butyl-8-fluoro-1-oxo-phthalazin-2-yl)-3-(hydroxymethyl)-4-pyridyl]-1-methyl-2-oxo-3-pyridyl]-2-methoxy-acetamide;

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-2-methoxy-acetamide;

N-[5-[3-(hydroxymethyl)-2-[1-oxo-6-(trifluoromethoxy)-3,4-dihydroisoquinolin-2-yl]-4-pyridyl]-1-methyl-2-oxo-3-pyridyl]cyclopropanecarboxamide;

1-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]-3-ethylurea;

N-[5-[2-(6-tert-butyl-1-methyl-benzimidazol-2-yl)-3-(hydroxymethyl)-4-pyridyl]-1-methyl-2-oxo-3-pyridyl]cyclopropanecarboxamide;

(R)—N4[5-[2-(6-tert-butyl-8-fluoro-1-oxo-phthalazin-2-yl)-3-(hydroxymethyl)-4-pyridyl]-1-methyl-2-oxo-3-pyridyl]spiro[2.2]pentane-2-carboxamide;

(S)—N-[5-[2-(6-tert-butyl-8-fluoro-1-oxo-phthalazin-2-yl)-3-(hydroxymethyl)-4-pyridyl]-1-methyl-2-oxo-3-pyridyl]spiro[2.2]pentane-2-carboxamide;

N-[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]butanamide;

N-[5-[2-(5-tert-butyl-1-methyl-benzimidazol-2-yl)-3-(hydroxymethyl)-4-pyridyl]-1-methyl-2-oxo-3-pyridyl]cyclopropanecarboxamide;

(R)—N-[5-[2-(6-tert-butyl-4-fluoro-1-oxo-phthalazin-2-yl)-3-(hydroxymethyl)-4-pyridyl]-1-methyl-2-oxo-3-pyridyl]-6-methyl-6-azaspiro[2.5]octane-2-carboxamide;

(S)—N-[5-[2-(6-tert-butyl-8-fluoro-1-oxo-phthalazin-2-yl)-3-(hydroxymethyl)-4-pyridyl]-1-methyl-2-oxo-3-pyridyl]-6-methyl-6-azaspiro[2.5]octane-2-carboxamide;

(1R,3S)—N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide;

N2-[5-[2-(6-tert-butyl-8-fluoro-1-oxo-phthalazin-2-yl)-3-(hydroxymethyl)-4-pyridyl]-1-methyl-2-oxo-3-pyridyl]-N1,N1-dimethyl-cyclopropane-1,2-dicarboxamide;

N2-[5-[2-(6-tert-butyl-8-fluoro-1-oxo-phthalazin-2-yl)-3-(hydroxymethyl)-4-pyridyl]-1-methyl-2-oxo-3-pyridyl]-N1,N1-dimethyl-cyclopropane-1,2-dicarboxamide;

(1S,3S)—N-[5-[2-(6-tert-butyl-8-fluoro-1-oxo-phthalazin-2-yl)-3-hydroxymethyl)-4-pyridyl]-1-methyl-2-oxo-3-pyridyl]-5-methyl-5-azaspiro[2.4]heptane-2-carboxamide;

(1S,3R)—N4[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide;

(1R,3R)—N-[5-[2-(6-tert-butyl-8-fluoro-1-oxo-phthalazin-2-yl)-3-(hydroxymethyl)-4-pyridyl]-1-methyl-2-oxo-3-pyridyl]-5-methyl-5-azaspiro[2.4]heptane-2-carboxamide; and.

20. A pharmaceutical composition comprising a compound of claim 1 and a pharmaceutically acceptable carrier, glidant, diluent, or excipient.

21. The pharmaceutical composition according to claim 20, further comprising a therapeutic agent.

\* \* \* \* \*